US010473640B2

(12) United States Patent
Singh et al.

(10) Patent No.: US 10,473,640 B2
(45) Date of Patent: Nov. 12, 2019

(54) DRUG SELECTION FOR GASTRIC CANCER THERAPY USING ANTIBODY-BASED ARRAYS

(75) Inventors: Sharat Singh, Rancho Santa Fe, CA (US); Phillip Kim, Irvine, CA (US); Xinjun Liu, San Diego, CA (US); Belen Ybarrondo, San Diego, CA (US)

(73) Assignee: Société des Produits Nestlé S.A., Vevey (CH)

( * ) Notice: Subject to any disclaimer, the term of this patent is extended or adjusted under 35 U.S.C. 154(b) by 0 days.

(21) Appl. No.: 13/014,674

(22) Filed: Jan. 26, 2011

(65) Prior Publication Data

US 2011/0281748 A1 Nov. 17, 2011
US 2013/0237436 A9 Sep. 12, 2013

Related U.S. Application Data

(63) Continuation of application No. PCT/US2010/042182, filed on Jul. 15, 2010, and a continuation-in-part of application No. 12/046,381, filed on Mar. 11, 2008, now Pat. No. 8,658,388, which is a continuation of application No. PCT/US2007/079002, filed on Sep. 20, 2007.

(60) Provisional application No. 60/913,087, filed on Apr. 20, 2007, provisional application No. 61/007,527, filed on Sep. 21, 2006, provisional application No. 61/225,866, filed on Jul. 15, 2009, provisional application No. 61/265,218, filed on Nov. 30, 2009, provisional application No. 61/325,000, filed on Apr. 16, 2010.

(51) Int. Cl.
G01N 33/50 (2006.01)

(52) U.S. Cl.
CPC ..... *G01N 33/5011* (2013.01); *G01N 33/5041* (2013.01)

(58) Field of Classification Search
None
See application file for complete search history.

(56) References Cited

U.S. PATENT DOCUMENTS

| | | | |
|---|---|---|---|
| 4,233,402 A | 11/1980 | Maggio et al. | |
| 4,690,890 A | 9/1987 | Loor et al. | |
| 4,975,532 A * | 12/1990 | Rowley et al. | 536/51 |
| 5,089,419 A | 2/1992 | Kuniyuki | |
| 5,120,660 A | 6/1992 | Kuniyuki | |
| 5,192,660 A | 3/1993 | Reed-Gitomer | |
| 5,445,944 A | 8/1995 | Ullman | |
| 5,516,931 A | 5/1996 | Giese et al. | |
| 5,527,684 A | 6/1996 | Mabile et al. | |
| 5,876,944 A | 3/1999 | Kuo | |
| 6,201,109 B1 | 3/2001 | Avnur et al. | |
| 6,335,173 B1 | 1/2002 | Kaplan | |
| 6,406,913 B1 | 6/2002 | Ullman et al. | |
| 6,511,809 B2 * | 1/2003 | Baez et al. | 435/6.11 |
| 6,627,400 B1 | 9/2003 | Singh et al. | |
| 6,649,351 B2 | 11/2003 | Matray et al. | |
| 6,659,351 B1 | 12/2003 | Bailleu et al. | |
| 6,770,439 B2 | 8/2004 | Singh et al. | |
| 6,818,399 B2 | 11/2004 | Singh et al. | |
| 6,949,347 B2 | 9/2005 | Singh et al. | |
| 6,972,198 B2 | 12/2005 | Craig et al. | |
| 7,101,682 B2 | 9/2006 | Ullman et al. | |
| 7,279,286 B2 | 10/2007 | Kannt et al. | |
| 7,402,399 B2 | 7/2008 | Mukherjeei et al. | |
| 7,537,938 B2 | 5/2009 | Kirakossian et al. | |
| 7,695,924 B2 | 4/2010 | Perez et al. | |
| 7,695,926 B2 | 4/2010 | Perez et al. | |
| 8,163,499 B2 | 4/2012 | Singh et al. | |
| 8,609,349 B2 | 12/2013 | Singh et al. | |
| 8,658,388 B2 | 2/2014 | Harvey et al. | |
| 9,250,243 B2 | 2/2016 | Singh et al. | |
| 9,274,116 B2 | 3/2016 | Singh et al. | |
| 9,285,369 B2 | 3/2016 | Harvey et al. | |
| 9,575,066 B2 | 2/2017 | Harvey et al. | |
| 9,664,683 B2 | 5/2017 | Singh et al. | |
| 9,719,995 B2 | 8/2017 | Kim et al. | |
| 2002/0142361 A1 | 10/2002 | Emmert-Buck | |
| 2002/0168641 A1 | 11/2002 | Mortensen et al. | |
| 2003/0059811 A1 | 3/2003 | Djaballah et al. | |
| 2003/0087311 A1 | 5/2003 | Wolf | |
| 2003/0153013 A1 | 8/2003 | Huang | |
| 2003/0153014 A1 | 8/2003 | Shen et al. | |
| 2003/0190689 A1 | 10/2003 | Crosby et al. | |
| 2004/0077090 A1 | 4/2004 | Short | |
| 2004/0106161 A1 | 6/2004 | Bossenmaier et al. | |
| 2004/0157271 A1 | 8/2004 | Kirakossian et al. | |

(Continued)

FOREIGN PATENT DOCUMENTS

| | | |
|---|---|---|
| CA | 2 588 992 A1 | 6/2006 |
| EP | 0 310 132 A2 | 4/1989 |

(Continued)

OTHER PUBLICATIONS

Daly et al. Evaluating concentration estimation errors in ELISA microarray experiments. BMC Bioinformatics, 6:17, 2005, printed as pp. 1/11 to 11/11.*
Kuhlmann et al. Glucose oxidase as label in hitological immunoassays with enzyme-amplification in a two-step technique: coimmobilized horseradish peroxidase as secondary system enzyme for chromogen oxidation. Histochemistry, vol. 85, pp. 13-17, 1986.*
Wiese et al. Simultaneous multianylyte ELISA performed on a microarray platform. Clinical Chemistry, vol. 47, No. 8, pp. 1451-1457, 2004.*
Woodbury et al. Elevated HGF levels in sera from breast cancer patients detected using a protein microarray ELISA. Journal of Proteome Research, vol. 1, pp. 233-237, 2002.*

(Continued)

*Primary Examiner* — Nelson B Moseley, II
(74) *Attorney, Agent, or Firm* — Kilpatrick Townsend & Stockton LLP

(57) ABSTRACT

The present invention provides methods for selecting a suitable anticancer therapy, and for identifying and predicting response for the treatment of a gastric cancer.

18 Claims, 27 Drawing Sheets

(56) References Cited

U.S. PATENT DOCUMENTS

| | | |
|---|---|---|
| 2004/0175696 A1 | 9/2004 | Ullman et al. |
| 2004/0235002 A1 | 11/2004 | Holmes et al. |
| 2004/0265923 A1 | 12/2004 | Gilmore et al. |
| 2004/0265938 A1* | 12/2004 | Remacle et al. ............. 435/7.92 |
| 2005/0069962 A1 | 3/2005 | Archer et al. |
| 2005/0153342 A1 | 7/2005 | Chen |
| 2006/0013819 A1 | 1/2006 | Kelsey |
| 2006/0024723 A1 | 2/2006 | Hussa et al. |
| 2006/0024846 A1 | 2/2006 | Singh et al. |
| 2006/0127945 A1 | 6/2006 | Preaudat et al. |
| 2007/0111944 A1 | 5/2007 | Scrofani et al. |
| 2007/0269902 A1 | 11/2007 | Beechem et al. |
| 2008/0096235 A1 | 4/2008 | Kimberly et al. |
| 2008/0176229 A1 | 7/2008 | Agus et al. |
| 2008/0187948 A1 | 8/2008 | Chan-Hui et al. |
| 2008/0261829 A1 | 10/2008 | Harvey et al. |
| 2009/0035792 A1 | 2/2009 | Singh et al. |
| 2009/0124511 A1 | 5/2009 | Archer et al. |
| 2010/0021457 A1 | 1/2010 | Pfleger et al. |
| 2010/0167945 A1 | 7/2010 | Singh et al. |
| 2010/0311185 A1 | 12/2010 | Schelp et al. |
| 2011/0275097 A9 | 11/2011 | Singh et al. |
| 2012/0231965 A1 | 9/2012 | Kim et al. |
| 2012/0270745 A1 | 10/2012 | Singh et al. |
| 2013/0045880 A1 | 2/2013 | Singh et al. |
| 2013/0216523 A1 | 8/2013 | Wallweber et al. |
| 2013/0315933 A1 | 11/2013 | Renner et al. |
| 2013/0324430 A1 | 12/2013 | Kim et al. |
| 2014/0187445 A1 | 7/2014 | Harvey et al. |
| 2014/0349865 A1 | 11/2014 | Singh et al. |
| 2015/0017659 A1 | 1/2015 | Singh et al. |
| 2015/0051107 A1 | 2/2015 | Harvey et al. |
| 2016/0123984 A1 | 5/2016 | Singh et al. |
| 2017/0184592 A1 | 6/2017 | Harvey et al. |
| 2018/0080934 A1 | 3/2018 | Kim et al. |

FOREIGN PATENT DOCUMENTS

| | | |
|---|---|---|
| EP | 1 145 004 B1 | 4/2004 |
| EP | 1 673 635 B1 | 4/2009 |
| EP | 2 065 475 A1 | 6/2009 |
| EP | 1751309 B1 | 7/2015 |
| JP | 60-228962 | 11/1985 |
| JP | 62-501892 | 7/1987 |
| JP | 01-163661 | 6/1989 |
| JP | H06-109734 A | 4/1994 |
| JP | 07-216000 A2 | 8/1995 |
| JP | H10-501070 A | 1/1998 |
| JP | 2002-214237 A | 7/2002 |
| JP | 2002-530629 T | 9/2002 |
| JP | 2005-500045 A | 1/2005 |
| JP | 2006-521821 | 9/2006 |
| JP | 2007-510910 A | 4/2007 |
| JP | 2008-503476 | 2/2008 |
| JP | 2008-292424 A | 12/2008 |
| JP | 2010-504532 | 2/2010 |
| RU | 2149404 C1 | 5/2000 |
| RU | 2165081 C | 4/2001 |
| WO | 86/04822 | 8/1986 |
| WO | 96/07103 A1 | 3/1996 |
| WO | 00/29609 | 5/2000 |
| WO | WO 01/27611 A2 | 4/2001 |
| WO | WO 02/090964 A1 | 11/2002 |
| WO | WO 03/006104 A2 | 1/2003 |
| WO | WO 03/087761 A2 | 10/2003 |
| WO | WO 2004/071572 A2 | 8/2004 |
| WO | 2004/092353 | 10/2004 |
| WO | 2005/037071 A2 | 4/2005 |
| WO | WO 2005/044794 A2 | 5/2005 |
| WO | WO 05/095965 A1 | 10/2005 |
| WO | 2006/007398 A1 | 1/2006 |
| WO | 2006/031815 A1 | 3/2006 |
| WO | WO 2006/044748 A2 | 4/2006 |
| WO | WO 2006/045991 A1 | 5/2006 |
| WO | WO 2006/054991 A | 5/2006 |
| WO | WO 2006/055739 A2 | 5/2006 |
| WO | WO 2006/105642 A1 | 10/2006 |
| WO | WO 2006/119980 A1 | 11/2006 |
| WO | 2007/130677 A2 | 11/2007 |
| WO | WO 2008/019375 A2 | 2/2008 |
| WO | WO 2008/036802 A2 | 3/2008 |
| WO | 2008/064884 A1 | 6/2008 |
| WO | WO 2009/012140 A2 | 1/2009 |
| WO | WO 2009108637 A1 * | 9/2009 |
| WO | 2011/008990 A1 | 1/2011 |

OTHER PUBLICATIONS

Litt et al. Chapter 10. "Tyramide Signal Amplification: Applications in Detecting Infectious Agents." in Rapid Detection of Infectious Agents, Ed. Specter et al. Plenum Press, New York 1998, pp. 159-173.*

Stern. Phosphoproteomics for oncology discovery and treatment. Expert Opinion on Therapeutic Targets, vol. 9, No. 4, pp. 851-860, Aug. 2005.*

Becker et al. Role of receptor tyrosine kinases in gastric cancer: New targets for a selective therapy. World Journal of Gasteroenterology, vol. 12, No. 21, pp. 3297-3305, Jun. 7, 2006.*

Kopf et al. (International Journal of Biochemistry and Cell Biology, 39:1305-1317, 2007).*

Angenendt, P. et al. "3D Protein microarrays: performing multiplex immunoassays on a single Chip," Anal. Chem., 2003, 75:4368-4372.

Arpino, G. et al., "Infiltrating lobular carcinoma of the breast: tumor characteristics and clinical outcome," Breast Cancer Research, 2003, 6:R149-156.

Bartling, B. et al., "Comparative application of antibody and gene array for expression profiling in human squamous cell lung carcinoma," Lung Cancer, 2005, 49(2):145-154.

Blume-Jensen, P. and Hunter, T., "Oncogenic kinase signalling," Nature, 2001, 411:355-365.

Dorland's Medical Dictionary for Healthcare Consumers (non-small cell carcinoma, Merck Sharp & Dohme Corp.) 2007, 1 page.

Gembitsky, D. et al., "A prototype antibody microarray platform to monitor changes in protein tyrosine phosphorylation," Molecular & Cellular Proteomics, 2004, 3(11):1102-1118.

Haab, B., "Antibody arrays in cancer research, " Molecular & Cellular Proteomics, 2005, 4(4):377-383.

Haab, B., "Applications of antibody array platforms," Current Opinion in Biotechnology, 2006, 17:415-421.

Hudelist, G. et al. "Use of high-throughput protein array for profiling of differentially expressed proteins in normal and malignant breast tissue," Breast Cancer Research and Treatment, 2004, 86:281-291.

Kopf, E. et al. "Antibody arrays—An emerging tool in cancer proteomics," The International Journal of Biochemistry & Cell Biology, 2007, 39:1305-1317.

Langry, K. et al., "Chemiluminescence assay for the detection of biological warfare agents," U.S. Dept. of Energy Report No. UCRL-ID-136797, Nov. 5, 1999, 30 pages.

Lu, Z. et al., "Construction of an antibody microarray based on agarose-coated slides," Electrophoresis, 2007, 28:406-413.

Mouridsen, H. et al., "Phase III study of letrozole versus tamoxifen as first line therapy of advanced breast cancer in postmenopausal women: analysis of survival and update of efficiency from the international letrozole breast cancer group," Journal of Clinical Oncology, 2003, 21:2101-2109.

Nielsen, U. et al. "Profiling receptor tyrosine kinase activation by using Ab microarrays," PNAS, 2003, 100(16):9330-9335.

Nielsen, U. et al. "Multiplexed sandwich assays in microarray format," Journal of Immunological Methods, 2004, 290:107-120.

Pearce, S. et al., "Modulation of estrogen receptor α function and stability by tamoxifen and a critical amino acid (asp-538) in helix 12," Journal of Biological Chemistry, 2003, 278:7630-7638.

Restriction Requirement dated Jun. 25, 2010 in U.S. Appl. No. 12/046,381, filed Mar. 11, 2008; 12 pages.

(56) References Cited

OTHER PUBLICATIONS

Sanchez-Carbayo, M., "Antibody arrays: technical considerations and clinical applications in cancer," Clinical Chemistry, 2006, 52:1651-1659.
Scaltriti, M. et al., "Expression of p95HER2, a truncated form of the HER2 receptor and response to anti-HER2 therapies in breast cancer," JNCI, 2007, 99(8):628-638.
Yonemura, Y. et al., "Role of vascular endothelial growth factor C expression in the development of lymph node metastasis in gastric cancer," Clinical Cancer Research, 1999, 5:1823-1829.
Engelman, J. et al., "ErbB-3 mediates phosphoinositide 3-kinase activity in gefitinib-sensitive non-small cell lung cancer cell lines," PNAS, 2005, 102(10):3788-93.
Samuilov, V.D., Immunofermentnyi analiz [Immunoenzyme analysis], Sorosovskii obrazovatelnyi zhurnal, No. 12, 1999, pp. 9-15.
Bachleitner-Hofmann, T. et al., "HER kinase activation confers resistance to MET tyrosine kinase inhibition in MET oncogene-addicted gastric cancer cells," Molecular Cancer Therapeutics, 7(11):3499-3508, 2008.
Engelman, J. et al., "Met amplification leads to gefitinib resistance in lung cancer by activating ERBB3 signaling," Science, 316(5827):1039-1043, 2007.
Huang, F. et al., "The mechanisms of differential sensitivity to an insulin-like growth factor-1 receptor inhibitor (BMS-536924) and rationale for combining with EGFR/HER2 inhibitors," Cancer Research, 69(1):161-170, 2009.
Kelkar, S. et al., "Cytoplasmic Dynein Mediates Adenovirus Binding to Microtubules," J. Virol., 2004, 78(18):10122-10132.
Zhou, B. et al., "Targeting ADAM-mediated ligand cleavage to inhibit HER3 and EGFR pathways in non-small cell lung cancer," Cancer Cell, 2006, 10:39-50.
Ahn, S. et al., "Molecular markers for individualized therapy in colorectal cancer: Progress towards a pharmacogenomics array," Curr Pharma and Personalized Medicine, 7:70-80, 2009.
Di Fiore et al., "Clinical relevance of KRAS mutation detection in metastatic colorectal cancer treated by Cetuximab plus chemotherapy," British Journal of Cancer 96:1166-69, 2007.
Glucose Oxidase (MeSH http://www.ncbi.nlm.nih.gov/mesh/?term=glucose+oxidase, 1964), "MeSH".
Humblet, Y., "Cetuximab: an $IgG_1$ monoclonal antibody for the treatment of epidermal growth factor receptor-expressing tumours," Expert Opin. Pharmacother., 5(7):1621-1633, 2004.
Kim, P. et al., "Highly sensitive proximity mediated immunoassay reveals HER2 status conversion in the circulating tumor cells of metastatic breast cancer patients," Proteome Science, 9:75, 2011, 15 pgs.
Langer, C.J., "Emerging role of epidermal growth factor receptor inhibition in therapy for advanced malignancy: focus on NSCLC," Int. J. Radiation Oncology Biol. Phys., 58(3):991-1002, 2004.
Sathyanarayanan, S. et al., "229 Anti-IGF1R therapy with dalotuzumab is efficacious in a sub-set of KRAS mutant cetuximab refractory CRC models," Eur. J. Cancer, Supplement, 8(7):75, 2010.
Siena, S. et al., "Biomarkers predicting clinical outcome of epidermal growth factor receptor-targeted therapy in metastatic colorectal cancer," J. Natl. Cancer Inst., 101(19):1308-1324, 2009.
Ubersax et al., "Mechanisms of specificity in protein phosphorylation," Nature, 8:530-541, 2007.
Yan, J. et al., "Role of antibody chip in analysis of inflammatory cytokine expression in severe sepsis," Chin. J. Emerg. Med., 15(9):830-833, 2006.
Yasui, W. et al., "Expression of epidermal growth factor receptor in human gastric and colonic carcinomas," Cancer Res, Jan. 1, 1988, 48(1), 137-141.
Cao, Y. et al., "Heterodimers of placenta growth factor/vascular endothelial growth factor," J. Bio. Chem., 271:3154-62, 1996.
De Roock, W. et al., "Association of KRAS p. G13D mutation with outcome in patients with chemotherapy-refractory metastatic colorectal cancer treated with Cetuximab," JAMA, 304(16):1812-1820, 2010.
Lemmon, M. et al., "Cell signaling by receptor tyrosine kinases," Cell, 141:1117-1134, 2010.

* cited by examiner c-Met Chip

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| A | | \multicolumn{3}{c}{c-Met} | | ErbB1 | | | ErbB2 | | | p95ErbB2 | | | ErbB3 | | | IGF-1R | | |
| B | | | | | | | | | | | | | | | | | | | | |
| C | | | | | | | | | | | | | | | | | | | | |
| D | | | | | | | | | | | | | | | | | | | | |
| E | | RON | | | | c-Kit | | | PI3K | | | SHC | | | VEGFR1 | | | VEGFR2 | | |
| F | | | | | | | | | | | | | | | | | | | | |
| G | | | | | | | | | | | | | | | | | | | | |
| H | | | | | | | | | | | | | | | | | | | | |
| I | | VEGFR3 | | | | | | | | | | | | | | | | | | |
| J | | | | | | | | | | | | | | | | | | | | |
| K | | | | | | | | | | | | | | | | | | | | |
| L | | | | | | | | | | | | | | | | | | | | |
| M | | | | | | | | | | | | | | | | | | | | |
| N | | | | | | | | | | | | | | | | | | | | |
| O | | | | | | | | | | | | | | | | | | | | |
| P | | | | | | | | | | | | | | | | | | | | |
| Q | | | | | | | | | | | | CK Cont | | | Assay Cont | | | Printing Cont | | |
| R | | | | | | | | | | | | | | | | | | | | |
| S | | | | | | | | | | | | | | | | | | | | |
| T | | | | | | | | | | | | | | | | | | | | |

*FIG. 6*

Gastric Cancer Chip

|   | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|----|----|----|----|----|----|----|----|----|----|----|
| A | | \multicolumn{3}{c}{c-Met} | | | | | | | | | | | | | | | | |

*FIG. 7*

|  | CTC | HER2+ |
|---|---|---|
| positive | 39 | 12 |
| % | 48% | 14.6% |
| range | 1~6000* | 1(75) ~ 3(8) |
| median | 10 |  |
| total | 82 |  |

* Estimated

DRUG SELECTION FOR GASTRIC CANCER THERAPY USING ANTIBODY-BASED ARRAYS

CROSS-REFERENCE TO RELATED APPLICATIONS

This application is a continuation application of PCT/US2010/042182, filed Jul. 15, 2010, which application claims priority to U.S. Provisional Application No. 61/225,866, filed Jul. 15, 2009, U.S. Provisional Application No. 61/265,218, filed Nov. 30, 2009, and U.S. Provisional Application No. 61/325,000, filed Apr. 16, 2010, the disclosures of which are hereby incorporated by reference in their entirety for all purposes. This application is also a continuation-in-part of U.S. patent application Ser. No. 12/046,381, filed Mar. 11, 2008, now U.S. Pat. No. 8,658,388 which application is a continuation of International Patent Application No. PCT/US07/079002, filed Sep. 20, 2007, which application claims priority to U.S. Provisional Patent Application No. 60/913,087, filed Apr. 20, 2007, and U.S. Provisional Patent Application No. 61/007,527, filed Sep. 21, 2006, the disclosures of which are hereby incorporated by reference in their entirety for all purposes.

BACKGROUND OF THE INVENTION

A wide variety of human malignancies exhibit sustained c-Met stimulation, over expression, or mutation, including carcinomas of the breast, liver, lung, ovary, kidney, stomach (gastric) and thyroid. Notably, activating mutations in c-Met have been positively identified in patients with a particular hereditary form of papillary renal cancer, directly implicating c-Met in human tumorigenesis. Aberrant signaling of the c-Met signaling pathway due to dysregulation of the c-Met receptor or overexpression of its ligand, hepatocyte growth factor (HGF), has been associated with an aggressive phenotype. Extensive evidence that c-Met signaling is involved in the progression and spread of several cancers and an enhanced understanding of its role in disease have generated considerable interest in c-Met and HGF as major targets in cancer drug development.

This interest has led to the development of a variety of c-Met pathway antagonists with potential clinical applications. The three main approaches of pathway-selective anticancer drug development have included antagonism of ligand/receptor interaction, inhibition of the tyrosine kinase catalytic activity, and blockade of the receptor/effector interaction.

c-Met is the cell surface receptor for hepatocyte growth factor (HGF), also known as scatter factor. HGF is a multidomain glycoprotein that is highly related to members of the plasminogen serine protease family. It is secreted as a single-chain, inactive polypeptide by mesenchymal cells and is cleaved to its active heterodimer by a number of proteases.

HGF binding induces c-Met receptor homodimerization and phosphorylation of two tyrosine residues (Y1234 and Y1235) within the catalytic site, regulating kinase activity. The carboxy-terminal tail includes tyrosines Y1349 and Y1356, which, when phosphorylated, serve as docking sites for intracellular adaptor proteins, leading to downstream signaling. The c-Met receptor is expressed in the epithelial cells of many organs during embryogenesis and in adulthood, including the liver, pancreas, prostate, kidney, muscle, and bone marrow.

One c-Met mediated cancer of interest is gastric cancer. Gastric cancer is the leading cause of cancer death worldwide with the incidence of 18.9/100,000 per year. The incidence of gastric cancer was estimated to be 934,000 cases, with 56% of the new cases occurring in East Asia. Gastric cancer accounts for 20.8% of all cancers in Korea according to the Central Tumor Registry data for 2002. Although gastrectomy is the only curative treatment in gastric cancer patients, a high recurrence rate ranging from 40~60% following curative surgery still accounts for poor overall survival.

Preliminary clinical results of several c-Met antagonists are now under clinical investigation. These agents, including monoclonal antibodies, disruptors of ligand/receptor interactions, and small-molecule tyrosine kinase inhibitors, have been encouraging. Several multi-targeted therapies have also been under investigation in the clinic and have demonstrated promise, particularly with regard to tyrosine kinase inhibition. In view of the role c-Met plays in a variety of cancers, there is need for the proper selection and strategies of therapies for an individual. This is especially true for c-Met mediated gastric cancers. The present invention satisfies these and other needs.

BRIEF SUMMARY OF THE INVENTION

The present invention provides compositions and methods for detecting the status (e.g., expression and/or activation levels) of components of signal transduction pathways in tumor cells (e.g., gastric tumor cells). Information on the expression and/or activation states of components of signal transduction pathways (e.g., HER2 and/or c-Met signal transduction pathway components) derived from practice of the present invention can be used for gastric cancer diagnosis, prognosis, and in the design of gastric cancer treatments.

In one aspect, the present invention provides a method for selecting a suitable anticancer drug for the treatment of a gastric cancer, the method comprising:

(a) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in a cellular extract produced from an isolated cancer cell; and (b) selecting a suitable anticancer drug for the treatment of the gastric cancer based upon the expression level and/or activation level of the one or more analytes determined in step (a).

In one particular embodiment, the present invention provides a method for selecting a suitable anticancer drug for the treatment of a gastric cancer, the method comprising:

(a) isolating a cancer cell after administration of an anticancer drug, or prior to incubation with an anticancer drug;

(b) lysing the isolated cell to produce a cellular extract;

(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract; and (d) comparing the expression level and/or activation level of the one or more analytes determined in step (c) to a reference expression and/or activation profile of the one or more analytes that is generated in the absence of the anticancer drug to determine whether the anticancer drug is suitable or unsuitable for the treatment of the gastric cancer.

In another particular embodiment, the present invention provides a method for selecting a suitable anticancer drug for the treatment of a gastric cancer, the method comprising:
(a) isolating a cancer cell after administration of an anticancer drug, or prior to incubation with an anticancer drug;
(b) lysing the isolated cell to produce a cellular extract;
(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract;
(d) comparing the expression level and/or activation level of the one or more analytes determined in step (c) to a reference expression and/or activation profile of the one or more analytes that is generated in the absence of the anticancer drug; and
(e) indicating that the anticancer drug is suitable for the treatment of the gastric cancer when the expression level and/or activation level determined for the one or more analytes is changed (e.g., substantially decreased) compared to the reference expression and/or activation profile.

In some embodiments, the methods of the present invention may be useful to aid or assist in the selection of a suitable anticancer drug for the treatment of a gastric tumor. In other embodiments, the methods of the present invention may be useful for improving the selection of a suitable anticancer drug for the treatment of a gastric tumor.

In another aspect, the present invention provides a method for identifying the response of a gastric cancer to treatment with an anticancer drug, the method comprising:
(a) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in a cellular extract produced from an isolated cancer cell; and
(b) identifying the response of the gastric cancer to treatment with an anticancer drug based upon the expression level and/or activation level of the one or more analytes determined in step (a).

In one particular embodiment, the present invention provides a method for identifying the response of a gastric cancer to treatment with an anticancer drug, the method comprising:
(a) isolating a cancer cell after administration of an anticancer drug, or prior to incubation with an anticancer drug;
(b) lysing the isolated cell to produce a cellular extract;
(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract; and
(d) comparing the expression level and/or activation level of the one or more analytes determined in step (c) to a reference expression and/or activation profile of the one or more analytes that is generated in the absence of the anticancer drug to identify whether the gastric cancer is responsive or non-responsive to treatment with the anticancer drug.

In another particular embodiment, the present invention provides a method for identifying the response of a gastric cancer to treatment with an anticancer drug, the method comprising:
(a) isolating a cancer cell after administration of an anticancer drug, or prior to incubation with an anticancer drug;
(b) lysing the isolated cell to produce a cellular extract;
(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract;
(d) comparing the expression level and/or activation level of the one or more analytes determined in step (c) to a reference expression and/or activation profile of the one or more analytes that is generated in the absence of the anticancer drug; and
(e) indicating that the gastric cancer is responsive to treatment with the anticancer drug when the expression level and/or activation level determined for the one or more analytes is changed (e.g., substantially decreased) compared to the reference expression and/or activation profile.

In some embodiments, the methods of the present invention may be useful to aid or assist in the identification of a gastric tumor's response to treatment with an anticancer drug. In other embodiments, the methods of the present invention may be useful for improving the identification of a gastric tumor's response to treatment with an anticancer drug.

In yet another aspect, the present invention provides a method for predicting the response of a subject having a gastric cancer to treatment with an anticancer drug, the method comprising:
(a) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in a cellular extract produced from an isolated cancer cell; and
(b) predicting the response of the subject having the gastric cancer to treatment with an anticancer drug based upon the expression level and/or activation level of the one or more analytes determined in step (a).

In one particular embodiment, the present invention provides a method for predicting the response of a subject having a gastric cancer to treatment with an anticancer drug, the method comprising:
(a) isolating a cancer cell after administration of an anticancer drug, or prior to incubation with an anticancer drug;
(b) lysing the isolated cell to produce a cellular extract;
(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract; and
(d) comparing the expression level and/or activation level of the one or more analytes determined in step (c) to a reference expression and/or activation profile of the one or more analytes that is generated in the absence of the anticancer drug to predict the likelihood that the subject having the gastric cancer will respond to treatment with the anticancer drug.

In another particular embodiment, the present invention provides a method for predicting the response of a subject having a gastric cancer to treatment with an anticancer drug, the method comprising:

(a) isolating a cancer cell after administration of an anticancer drug, or prior to incubation with an anticancer drug;
(b) lysing the isolated cell to produce a cellular extract;
(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract;
(d) comparing the expression level and/or activation level of the one or more analytes determined in step (c) to a reference expression and/or activation profile of the one or more analytes that is generated in the absence of the anticancer drug to predict the likelihood that the subject will respond to treatment with the anticancer drug; and
(e) indicating that the subject having the gastric cancer will likely respond to treatment with the anticancer drug when the expression level and/or activation level determined for the one or more analytes is changed (e.g., substantially decreased) compared to the reference expression and/or activation profile.

In some embodiments, the methods of the present invention may be useful to aid or assist in the prediction of a gastric cancer subject's likelihood of responding to treatment with an anticancer drug. In other embodiments, the methods of the present invention may be useful for improving the prediction of a gastric cancer subject's likelihood of responding to treatment with an anticancer drug.

Other objects, features, and advantages of the present invention will be apparent to one of skill in the art from the following detailed description and figures.

BRIEF DESCRIPTION OF THE DRAWINGS

FIG. 6 shows a schematic example of an addressable array comprising dilutions of antibodies to components of receptor tyrosine kinase pathways, such as those in the c-Met and EGFR/MAPK/ERK pathways. As a non-limiting example, antibodies may be plated in triplicate in four different dilutions on the addressable array.

FIG. 7 shows a schematic example of an addressable array comprising dilutions of antibodies to components of signal transduction pathways activated in gastric cancer. As a non-limiting example, antibodies may be plated in triplicate in four different dilutions on the addressable array.

DETAILED DESCRIPTION OF THE INVENTION

I. Introduction

Figure 1:
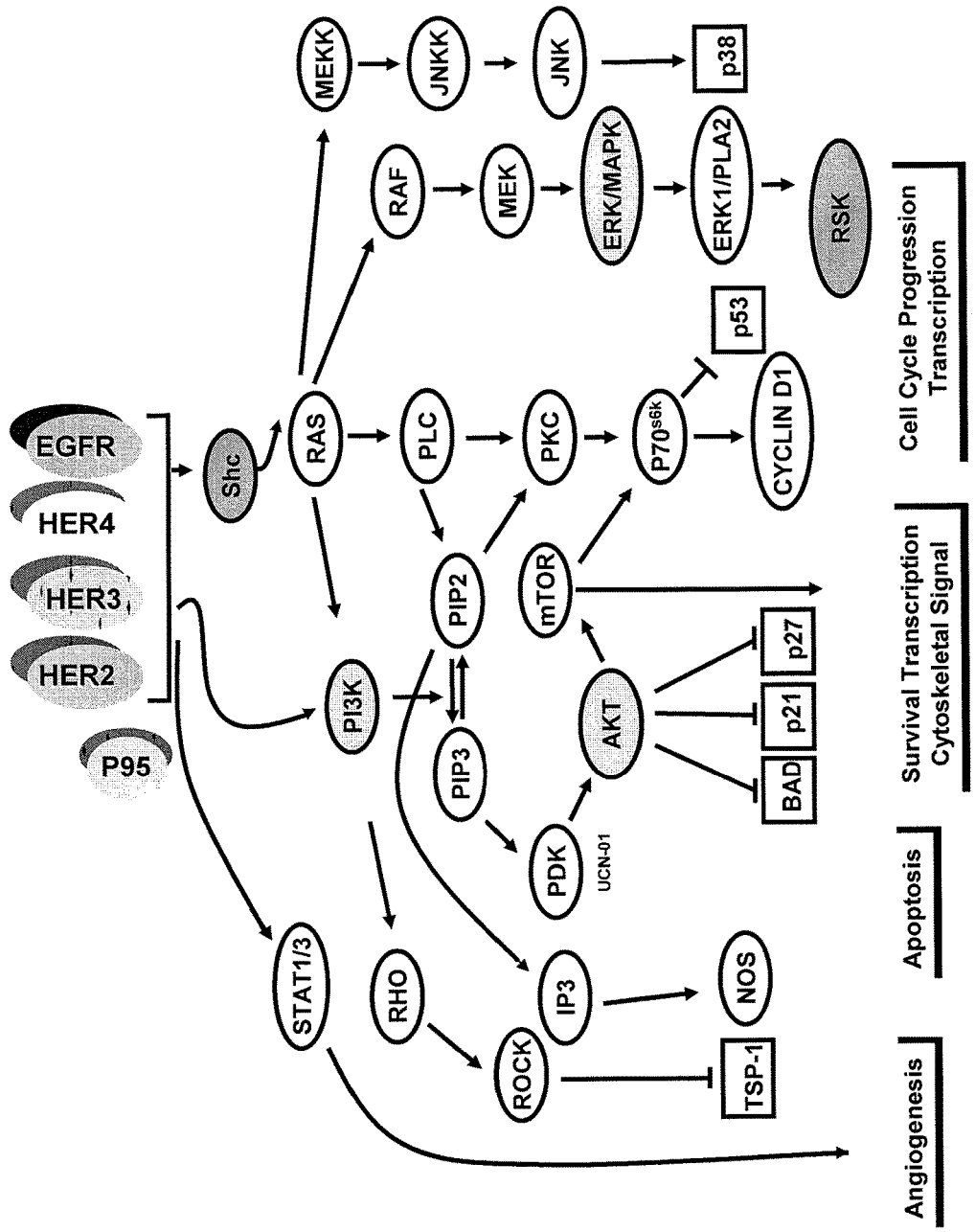
FIG. 1 shows an example of a signal transduction pathway involved in cell proliferation that may be used in the practice of the invention. Depicted are components of the EGFR/MAPK/ERK pathway that is used by cells to convert a mitogenic signal into cell proliferation.

As described above, the activation of signal transduction pathways that are involved in cell proliferation and the deactivation of pathways that are involved in cell death are non-limiting examples of molecular features that characterize many different types of cancer. In many cases, the activity of particular signal transduction pathways, and components thereof, can serve as molecular signatures for a given type of cancer. Such activated components can further provide useful targets for therapeutic intervention. Accordingly, knowledge of the activity level of a particular signal transduction system within a cancer cell prior to, during, and after treatment provides a physician with highly relevant information that can be used to select an appropriate course of treatment to adopt. Furthermore, the continued monitoring of signal transduction pathways that are active in cancer cells as treatment progresses can provide the physician with additional information on the efficacy of treatment, prompting the physician to either continue a particular course of treatment or to switch to another line of treatment, when, for example, cancer cells have become resistant to treatment through further aberrations that activate either the same or another signal transduction pathway.

Accordingly, the present invention provides methods and compositions for detecting the expression and activation states of a plurality of deregulated signal transduction molecules in tumor tissue or extratumoral cells such as rare circulating cells of a solid tumor in a specific, multiplex, high-throughput assay. The present invention also provides methods and compositions for the selection of appropriate therapy (single drugs or combinations of drugs) to down-regulate or shut down a deregulated signaling pathway. Thus, the invention can be used to facilitate the design of personalized therapies for cancer patients.

The ability to detect and identify tumor cells in the circulation through the determination of the activity of signal transduction pathways at the level of single cells is an important advantage of the present invention. Tumor cells are often found in the blood of patients with various early stages of cancer as "micrometastases" (disseminated tumor cells) and are also found in metastatic cancers. The number of tumor cells in blood will depend on the stage and type of tumor. While biopsies are typically obtained on primary tumors, most metastatic tumors are not biopsied, making molecular analysis of such tumor samples very difficult. During tumor metastasis, the most aggressive tumor cells leave the primary tumor and travel through the blood and lymphatic system to reach a distant location. Thus, circulating tumor cells from blood represent the most aggressive and homogenous population of tumor cells. However, the number of metastatic tumor cells in blood is frequently very low, varying from one to several thousand cells per milliliter of blood. The ability to isolate and assay signal transduction pathways in such rare cells and to apply this information toward more effective cancer treatments is one object of the present invention.

In some embodiments, the multiplex, high-throughput immunoassays of the present invention can detect the activation state of one or more signal transduction molecules in circulating cells of a solid tumor at the single cell level. In fact, signal transduction molecules such as EGFR and HER2 can be detected with a sensitivity of about 100 zeptomoles and a linear dynamic range of from about 100 zeptomoles to about 100 femtomoles. As such, single-cell detection of the activation state of multiple signal transducers in rare circulating cells facilitates cancer prognosis and diagnosis as well as the design of personalized, targeted therapies.

Rare circulating cells include circulating cells of a solid tumor that have either metastasized or micrometastasized from a solid tumor. Circulating tumor cells, cancer stem cells, and cells that are migrating to a tumor (e.g., due to chemoattraction) such as circulating endothelial progenitor cells, circulating endothelial cells, circulating pro-angiogenic myeloid cells, and circulating dendritic cells are some examples of circulating cells associated with a solid tumor.

Signal transduction molecules of interest are typically extracted shortly after the circulating cells are isolated to preserve their in situ activation state, preferably within about 24, 6, or 1 hr, and more preferably within about 30, 15, or 5 minutes. The isolated cells may also be incubated with one or more growth factors, usually at nanomolar to micromolar concentrations, for about 1-30 minutes to resuscitate or stimulate activation of the signal transduction molecules (see, e.g., Irish et al., *Cell*, 118:217-228 (2004)).

As explained in greater detail herein, to evaluate potential anticancer therapies for an individual patient, the isolated cells can be incubated with one or more anticancer drugs at varying doses. Growth factor stimulation can then be performed for a few minutes (e.g., about 1-5 minutes) or for several hours (e.g., about 1-6 hours). The differential activation of signaling pathways with and without anticancer drugs can aid in the selection of a suitable cancer therapy at the proper dose for each individual patent. Circulating cells can also be isolated from a patient sample during anticancer drug treatment and stimulated with one or more growth factors to determine whether a change in therapy should be implemented. As such, the methods of the present invention advantageously assist the clinician in providing the right anticancer drug at the right dose at the right time for every patient.

In contrast to currently available gastric cancer testing options, the methods of the present invention enable the monitoring of gastric cancer patients through all stages of the disease by providing a "real-time biopsy" of solid gastric tumors using samples such as circulating tumor cells (CTCs) from blood and/or fine needle aspirates (FNAs). As a non-limiting example, the gastric cancer assays described herein can be used in the initial diagnosis of gastric cancer in a patient at an early stage of the disease. Selection of a suitable cancer therapy is guided by profiling the expression and/or activation states of specific signaling pathways with and without anticancer drugs using the assays described herein. Advantageously, the methods of the present invention can also be used to monitor the progression or regression of the disease because therapeutic intervention may be based on samples taken at any stage of the disease and analyzed using the assays described herein. As such, selection of suitable cancer therapies for the early and metastatic stages of gastric cancer is guided by real-time diagnosis and an analysis of the expression and/or activation status of specific signaling pathway molecules.

The methods of the present invention are beneficially tailored to address key issues in cancer management and provide a higher standard of care for gastric cancer patients because they (1) provide increased sensitivity (e.g., single cell detection can be achieved for detecting total and phosphorylated signal transduction molecules such as EGFR and HER2), (2) provide increased specificity (e.g., three-antibody proximity assays enhance specificity for detecting total and phosphorylated signal transduction molecules), (3) enable pathway profiling (e.g., expression and/or activation status of specific signal transduction molecules can be detected in CTCs or FNA from patients), and (4) eliminate any issues with obtaining patient samples (e.g., assays can be performed on a few tumor cells). Although any sample may be used in the assays described herein, CTCs are particularly useful because they represent the most aggressive tumor cells, every tumor is known to shed CTCs, they can be the only source of residual tumors or hard-to-access metastatic tumors, and they are found in blood. As such, the methods of the present invention enable the serial sampling of gastric tumor tissues, resulting in valuable information on changes occurring in tumor cells as a function of time and therapy and providing clinicians with a means to monitor rapidly evolving cancer pathway signatures.

In sum, the compositions and methods of the present invention advantageously provide accurate prediction, selection, and monitoring of cancer patients (e.g., gastric cancer patients) most likely to benefit from targeted therapy by performing pathway profiling on easily accessible tumor cells using multiplexed, antibody-based proximity assays.

II. Definitions

As used herein, the following terms have the meanings ascribed to them unless specified otherwise.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, digestive and gastrointestinal cancers such as gastric cancer (e.g., stomach cancer), colorectal cancer, gastrointestinal stromal tumors (GIST), gastrointestinal carcinoid tumors, colon cancer, rectal cancer, anal cancer, bile duct cancer, small intestine cancer, and esophageal cancer; breast cancer; lung cancer (e.g., non-small cell lung cancer); gallbladder cancer; liver cancer; pancreatic cancer; appendix cancer; prostate cancer, ovarian cancer; renal cancer (e.g., renal cell carcinoma); cancer of the central nervous system; skin cancer; lymphomas; gliomas; choriocarcinomas; head and neck cancers; osteogenic sarcomas; and blood cancers. As used herein, a "tumor" comprises one or more cancerous cells.

The term "analyte" includes any molecule of interest, typically a macromolecule such as a polypeptide, whose presence, amount (expression level), activation state, and/or identity is determined. In certain instances, the analyte is a signal transduction molecule such as, e.g., a component of a HER2 (ErbB2) or c-Met signaling pathway.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER1/ErbB1, HER2/Neu/ErbB2, HER3/ErbB3, HER4/ErbB4), VEGFR1/FLT1, VEGFR2/FLK1/KDR, VEGFR3/FLT4, FLT3/FLK2, PDGFR (e.g., PDGFRA, PDGFRB), c-KIT/SCFR, INSR (insulin receptor), IGF-IR, IGF-IIR, IRR (insulin receptor-related receptor), CSF-1R, FGFR 1-4, HGFR 1-2, CCK4, TRK A-C, c-MET, RON, EPHA 1-8, EPHB 1-6, AXL, MER, TYRO3, TIE 1-2, TEK, RYK, DDR 1-2, RET, c-ROS, V-cadherin, LTK (leukocyte tyrosine kinase), ALK (anaplastic lymphoma kinase), ROR1-2, MUSK, AATYK 1-3, and RTK 106; truncated forms of receptor tyrosine kinases such as truncated HER2 receptors with missing amino-terminal extracellular domains (e.g., p95ErbB2 (p95m), p110, p95c, p95n, etc.); receptor tyrosine kinase dimers (e.g., p95HER2/HER3, p95HER2/HER2, HER2/HER2, HER2/HER3, HER1/HER2, HER2/HER3, HER2/HER4, etc.); non-receptor tyrosine kinases such as BCR-ABL, Src, Frk, Btk, Csk, Abl, Zap70, Fes/Fps, Fak, Jak, Ack, and LIMK; tyrosine kinase signaling cascade components such as AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, phosphatase and tensin homolog (PTEN), SGK3, 4E-BP1, P70S6K (e.g., p70 S6 kinase splice variant alpha I), protein tyrosine phosphatases (e.g., PTP1B, PTPN13, BDP1, etc.), RAF, PLA2, MEKK, JNKK, JNK, p38, Shc (p66), Ras (e.g., K-Ras, N-Ras, H-Ras), Rho, Rac1, Cdc42, PLC, PKC, p53, cyclin D1, STAT1, STAT3, phosphatidylinositol 4,5-bisphosphate (PIP2), phosphatidylinositol 3,4,5-trisphosphate (PIP3), mTOR, BAD, p21, p27, ROCK, IP3, TSP-1, NOS, GSK-3β, RSK 1-3, JNK, c-Jun, Rb, CREB, Ki67, and paxillin; nuclear hormone receptors such as estrogen receptor (ER), progesterone receptor (PR), androgen receptor, glucocorticoid receptor, mineralocorticoid receptor, vitamin A receptor, vitamin D receptor, retinoid receptor, thyroid hormone receptor, and orphan receptors; nuclear receptor coactivators and repressors such as amplified in breast cancer-1 (AIB1) and nuclear receptor corepressor 1 (NCOR), respectively; and combinations thereof.

The term "component of a HER2 signaling pathway" includes any one or more of an upstream ligand of HER2, binding partner of HER2, and/or downstream effector molecule that is modulated through HER2. Examples of HER2 signaling pathway components include, but are not limited to, heregulin, HER1/ErbB1, HER2/ErbB2, HER3/ErbB3, HER4/ErbB4, AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, PTEN, SGK3, 4E-BP1, P70S6K (e.g., splice variant alpha I), protein tyrosine phosphatases (e.g., PTP1B, PTPN13, BDP1, etc.), HER2 dimers (e.g., p95HER2/HER3, p95HER2/HER2, HER2/HER2, HER2/HER3, HER1/HER2, HER2/HER3, HER2/HER4, etc.), GSK-313, PIP2, PIP3, p27, and combinations thereof.

The term "component of a c-Met signaling pathway" includes any one or more of an upstream ligand of c-Met, binding partner of c-Met, and/or downstream effector molecule that is modulated through c-Met. Examples of c-Met signaling pathway components include, but are not limited to, hepatocyte growth factor/scatter factor (HGF/SF), Plexin B1, CD44v6, AKT (e.g., AKT1, AKT2, AKT3), MEK (MAP2K1), ERK2 (MAPK1), ERK1 (MAPK3), STAT (e.g., STAT1, STAT3), PI3K (e.g., PIK3CA (p110), PIK3R1 (p85)), GRB2, Shc (p66), Ras (e.g., K-Ras, N-Ras, H-Ras), GAB1, SHP2, SRC, GRB2, CRKL, PLCγ, PKC (e.g., PKCα, PKCβ, PKCδ), paxillin, FAK, adducin, RB, RB1, PYK2, and combinations thereof.

The term "activation state" refers to whether a particular signal transduction molecule such as a HER2 or c-Met signaling pathway component is activated. Similarly, the term "activation level" refers to what extent a particular signal transduction molecule such as a HER2 or c-Met signaling pathway component is activated. The activation state typically corresponds to the phosphorylation, ubiquitination, and/or complexation status of one or more signal transduction molecules. Non-limiting examples of activation states (listed in parentheses) include: HER1/EGFR (EGFRvIII, phosphorylated (p-) EGFR, EGFR:Shc, ubiquitinated (u-) EGFR, p-EGFRvIII); ErbB2 (p-ErbB2, p95HER2 (truncated ErbB2), p-p95HER2, ErbB2:Shc, ErbB2:PI3K, ErbB2:EGFR, ErbB2:ErbB3, ErbB2:ErbB4); ErbB3 (p-ErbB3, ErbB3:PI3K, p-ErbB3:PI3K, ErbB3:Shc); ErbB4 (p-ErbB4, ErbB4:Shc); c-MET (p-c-MET, c-Met: HGF complex); AKT1 (p-AKT1); AKT2 (p-AKT2); AKT3 (p-AKT3); PTEN (p-PTEN); P70S6K (p-P70S6K); MEK (p-MEK); ERK1 (p-ERK1); ERK2 (p-ERK2); PDK1 (p-PDK1); PDK2 (p-PDK2); SGK3 (p-SGK3); 4E-BP1 (p-4E-BP1); PIK3R1 (p-PIK3R1); c-KIT (p-c-KIT); ER (p-ER); IGF-1R (p-IGF-1R, IGF-1R:IRS, IRS:PI3K, p-IRS, IGF-1R:PI3K); INSR (p-INSR); FLT3 (p-FLT3); HGFR1 (p-HGFR1); HGFR2 (p-HGFR2); RET (p-RET); PDGFRA (p-PDGFRA); PDGFRB (p-PDGFRB); VEGFR1 (p-VEGFR1, VEGFR1:PLCγ, VEGFR1:Src); VEGFR2 (p-VEGFR2, VEGFR2:PLCγ, VEGFR2:Src, VEGFR2: heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); TIE1 (p-TIE1); TIE2 (p-TIE2); EPHA (p-EPHA); EPHB (p-EPHB); GSK-3β (p-GSK-3β); NFKB (p-NFKB), IKB (p-IKB, p-P65: IKB); BAD (p-BAD, BAD:14-3-3); mTOR (p-mTOR); Rsk-1 (p-Rsk-1); Jnk (p-Jnk); P38 (p-P38); STAT1 (p-STAT1); STAT3 (p-STAT3); FAK (p-FAK); RB (p-RB); Ki67; p53 (p-p53); CREB (p-CREB); c-Jun (p-c-Jun); c-Src (p-c-Src); paxillin (p-paxillin); GRB2 (p-GRB2), Shc (p-Shc), Ras (p-Ras), GAB1 (p-GAB1), SHP2 (p-SHP2), GRB2 (p-GRB2), CRKL (p-CRKL), PLCγ (p-PLCγ), PKC (e.g., p-PKCα, p-PKCβ, p-PKCδ), adducin (p-adducin), RB1 (p-RB1), and PYK2 (p-PYK2).

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, etc.

The term "superior dynamic range" as used herein refers to the ability of an assay to detect a specific analyte in as few as one cell or in as many as thousands of cells. For example, the immunoassays described herein possess superior dynamic range because they advantageously detect a particular signal transduction molecule of interest in about 1-10,000 cells (e.g., about 1, 5, 10, 25, 50, 75, 100, 250, 500, 750, 1000, 2500, 5000, 7500, or 10,000 cells) using a dilution series of capture antibody concentrations.

As used herein, the term "circulating cells" comprises extratumoral cells that have either metastasized or micrometastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.). Patient samples containing circulating cells can be obtained from any accessible biological fluid (e.g., whole blood, serum, plasma, sputum, bronchial lavage fluid, urine, nipple aspirate, lymph, saliva, fine needle aspirate, etc.). In certain instances, the whole blood sample is separated into a plasma or serum fraction and a cellular fraction (i.e., cell pellet). The cellular fraction typically contains red blood cells, white blood cells, and/or circulating cells of a solid tumor such as circulating tumor cells (CTCs), circulating endothelial cells (CECs), circulating endothelial progenitor cells (CEPCs), cancer stem cells (CSCs), disseminated tumor cells of the lymph node, and combinations thereof. The plasma or serum fraction usually contains, inter alia, nucleic acids (e.g., DNA, RNA) and proteins that are released by circulating cells of a solid tumor.

Circulating cells are typically isolated from a patient sample using one or more separation methods including, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), the Cell-Tracks® System by Immunicon (Huntingdon Valley, Pa.), microfluidic separation (see, e.g., Mohamed et al., *IEEE Trans. Nanobiosci.*, 3:251-256 (2004); Lin et al., Abstract No. 5147, 97th AACR Annual Meeting, Washington, D.C. (2006)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J. Oncol.*, 21:521-530 (2002)).

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), a tissue sample (e.g., tumor tissue) such as a surgical resection of a tumor, and cellular extracts thereof. In some embodiments, the sample is whole blood or a fractional component thereof such as plasma, serum, or a cell pellet. In preferred embodiments, the sample is obtained by isolating circulating cells of a solid tumor from whole blood or a cellular fraction thereof using any technique known in the art. In other embodiments, the sample is a formalin fixed paraffin embedded (FFPE) tumor tissue sample, e.g., from a solid tumor of the stomach or other portion of the gastrointestinal tract.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V. One skilled in the art will appreciate that biopsy techniques can be performed to identify cancerous and/or precancerous cells in a given tissue sample.

The term "subject" or "patient" or "individual" typically includes humans, but can also include other animals such as, e.g., other primates, rodents, canines, felines, equines, ovines, porcines, and the like.

An "array". or "microarray" comprises a distinct set and/or dilution series of capture antibodies immobilized or restrained on a solid support such as, for example, glass (e.g., a glass slide), plastic, chips, pins, filters, beads (e.g., magnetic beads, polystyrene beads, etc.), paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). In certain instances, the capture antibodies comprise capture tags which interact with capture agents bound to the solid support. The arrays used in the assays described herein typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample such as a cellular extract. In particular embodiments, the capture antibody is restrained on a solid support in an array. Suitable capture antibodies for immobilizing any of a variety of signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/streptavidin labels, nucleic acid (e.g., oligonucleotide) labels, chemically reactive labels, fluorescent labels, enzyme labels, radioactive labels, and combinations thereof. Suitable detection antibodies for detecting the activation state and/or total amount of any of a variety of signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phospho-specific antibodies against various phosphorylated forms of signal transduction molecules such as EGFR, c-KIT, c-Src, FLK-1, PDGFRA, PDGFRB, AKT, MAPK, PTEN, Raf, and MEK are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more signal transduction molecules. In some embodiments, the phosphorylation of members of the EGFR family of receptor tyrosine kinases and/or the formation of heterodimeric complexes between EGFR family members is detected using activation state-dependent antibodies. In particular embodiments, activation state-dependent antibodies are useful for detecting one or more sites of phosphorylation in one or more of the following signal transduction molecules (phosphorylation sites correspond to the position of the amino acid in the human protein sequence): EGFR/HER1/ErbB1 (e.g., tyrosine (Y) 1068); ErbB2/HER2 (e.g., Y1248); ErbB3/HER3 (e.g., Y1289); ErbB4/HER4 (e.g., Y1284); c-Met (e.g., Y1003, Y1230, Y1234, Y1235, and/or Y1349); SGK3 (e.g., threonine (T) 256 and/or serine (S) 422); 4E-BP1 (e.g., T70); ERK1 (e.g., T185, Y187, T202, and/or Y204); ERK2 (e.g., T185, Y187, T202, and/or Y204); MEK (e.g., S217 and/or S221); PIK3R1 (e.g., Y688); PDK1 (e.g., S241); P70S6K (e.g., T229, T389, and/or S421); PTEN (e.g., S380); AKT1 (e.g., S473 and/or T308); AKT2 (e.g., S474 and/or T309); AKT3 (e.g., S472 and/or T305); GSK-313 (e.g., S9); NFKB (e.g., S536); IKB (e.g., S32); BAD (e.g., S112 and/or S136); mTOR (e.g., S2448); Rsk-1 (e.g., T357 and/or S363); Jnk (e.g., T183 and/or Y185); P38 (e.g., T180 and/or Y182); STAT3 (e.g., Y705 and/or S727); FAK (e.g., Y397, Y576, 5722, Y861, and/or S910); RB (e.g., S249, T252, 5612, and/or S780); RB1 (e.g., S780); adducin (e.g., S662 and/or S724); PYK2 (e.g., Y402 and/or Y881); PKCα (e.g., S657); PKCα/β (e.g., T368 and/or T641); PKCδ (e.g., T505); p53 (e.g., S392 and/or S20); CREB (e.g., S133); c-Jun (e.g., S63); c-Src (e.g., Y416); and paxillin (e.g., Y31 and/or Y118).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more signal transduction molecules.

The term "nucleic acid" or "polynucleotide" includes deoxyribonucleotides or ribonucleotides and polymers thereof in either single- or double-stranded form such as, for example, DNA and RNA. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof and complementary sequences as well as the sequence explicitly indicated.

The term "oligonucleotide" includes a single-stranded oligomer or polymer of RNA, DNA, RNA/DNA hybrid, and/or a mimetic thereof. In certain instances, oligonucleotides are composed of naturally-occurring (i.e., unmodified) nucleobases, sugars, and internucleoside (backbone) linkages. In certain other instances, oligonucleotides comprise modified nucleobases, sugars, and/or internucleoside linkages.

As used herein, the term "mismatch motif" or "mismatch region" refers to a portion of an oligonucleotide that does not have 100% complementarity to its complementary sequence. An oligonucleotide may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "stringent hybridization conditions" refers to conditions under which an oligonucleotide will hybridize to its complementary sequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region) when compared and aligned for maximum correspondence over a comparison window or designated region as measured using a sequence comparison algorithm or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

The term "incubating" is used synonymously with "contacting" and "exposing" and does not imply any specific time or temperature requirements unless otherwise indicated.

"Receptor tyrosine kinases" or "RTKs" include a family of fifty-six (56) proteins characterized by a transmembrane domain and a tyrosine kinase motif. RTKs function in cell signaling and transmit signals regulating growth, differentiation, adhesion, migration, and apoptosis. The mutational activation and/or overexpression of receptor tyrosine kinases transforms cells and often plays a crucial role in the development of cancers. RTKs have become targets of various molecularly targeted agents such as trastuzumab, cetuximab, gefitinib, erlotinib, sunitinib, imatinib, nilotinib, and the like. One well-characterized signal transduction pathway is the MAP kinase pathway, which is responsible for transducing the signal from epidermal growth factor (EGF) to the promotion of cell proliferation in cells (see, FIG. 1).

III. Description of the Embodiments

The present invention provides compositions and methods for detecting the status (e.g., expression and/or activation levels) of components of signal transduction pathways in tumor cells derived from tumor tissue or circulating cells of a solid tumor with an assay such as a specific, multiplex, high-throughput proximity assay as described herein. The present invention also provides compositions and methods for selecting appropriate therapies to downregulate or shut down one or more deregulated signal transduction pathways. Thus, certain embodiments of the invention may be used to facilitate the design of personalized therapies based on the particular molecular signature provided by the collection of total and activated signal transduction proteins in a given patient's tumor (e.g., a gastric tumor).

In particular aspects, the present invention provides molecular markers (biomarkers) that enable the determination or prediction of whether a particular cancer can respond or is likely to respond favorably to an anticancer drug such as, for example, a HER2-modulating compound (e.g., a HER2 inhibitor) and/or a c-Met-modulating compound (e.g., a c-Met inhibitor). In specific embodiments, measuring the level of expression and/or activation of one or more components of the HER2 and/or c-Met signaling pathways (e.g., HER1, HER2, p95HER2, HER3, c-Met, IGF1R, cKit, PI3K, Shc, Akt, p70S6K, VEGFR, and/or PDGFR) is particularly useful for selecting a suitable anticancer drug and/or identifying or predicting a response thereto in cells such as gastric cancer cells (e.g., isolated circulating tumor cells, fine needle aspirate (FNA) cells, and the like).

In one aspect, the present invention provides a method for selecting a suitable anticancer drug for the treatment of a gastric cancer, the method comprising:

(a) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in a cellular extract produced from an isolated cancer cell; and (b) selecting a suitable anticancer drug for the treatment of the gastric cancer based upon the expression level and/or activation level of the one or more analytes determined in step (a).

In some embodiments, the expression level and/or activation level of the one or more analytes is expressed as a relative fluorescence unit (RFU) value that corresponds to the signal intensity for a particular analyte of interest that is determined using, e.g., a proximity assay such as the Collaborative Proximity Immunoassay (COPIA) described herein. In other embodiments, the expression level and/or activation level of the one or more analytes is expressed as "−", "±", "+", "++", "+++", or "++++" that corresponds to increasing signal intensity for a particular analyte of interest that is determined using, e.g., a proximity assay such as COPIA. In some instances, an undetectable or minimally detectable level of expression or activation of a particular analyte of interest that is determined using, e.g., a proximity assay such as COPIA, may be expressed as "−" or "±". In other instances, a low level of expression or activation of a particular analyte of interest that is determined using, e.g., a proximity assay such as COPIA, may be expressed as "+". In yet other instances, a moderate level of expression or activation of a particular analyte of interest that is determined using, e.g., a proximity assay such as COPIA, may be expressed as "++". In still yet other instances, a high level of expression or activation of a particular analyte of interest that is determined using, e.g., a proximity assay such as COPIA, may be expressed as "+++". In further instances, a very high level of expression or activation of a particular analyte of interest that is determined using, e.g., a proximity assay such as COPIA, may be expressed as "++++".

In yet other embodiments, the expression level and/or activation level of the one or more analytes is quantitated by calibrating or normalizing the RFU value that is determined using, e.g., a proximity assay such as COPIA, against a standard curve generated for the particular analyte of interest. In certain instances, a computed units (CU) value can be calculated based upon the standard curve. In other instances, the CU value can be expressed as "−", "±", "+", "++", "+++", or "++++" in accordance with the description above for signal intensity. Example 13 provides a non-limiting example of data analysis for the quantitation of signal transduction pathway proteins (e.g., one or more HER2 and/or c-MET signaling pathway components) in gastric cancer cells.

In certain embodiments, the expression or activation level of a particular analyte of interest, when expressed as "−", "±", "+", "++", "+++", or "++++", may correspond to a level of expression or activation that is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher or lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher or lower) than a reference expression level or activation level, e.g., when compared to a negative control such as an IgG control, when compared to a standard curve generated for the analyte of interest, when compared to a positive control such as a pan-CK control, when compared to an expression or activation level determined in the presence of an anticancer drug, and/or when compared to an expression or activation level determined in the absence of an anticancer drug. In some instances, the correlation is analyte-specific. As a non-limiting example, a "+" level of expression or activation determined using, e.g., a proximity assay such as COPIA, may correspond to a 2-fold increase in expression or activation for one analyte and a 5-fold increase for another analyte when compared to a reference expression or activation level.

In some embodiments, the cancer cell is isolated from a subject having the gastric cancer after administration of an anticancer drug to the subject. In other embodiments, the isolated cancer cell is contacted with an anticancer drug. In either of these embodiments, the suitable anticancer drug may be selected by comparing the expression level and/or activation level of the one or more analytes to a reference expression and/or activation profile of the one or more analytes generated in the absence of the anticancer drug.

In certain embodiments, step (b) comprises applying the expression level and/or activation level of the one or more analytes determined in step (a) to select a suitable anticancer drug for the treatment of the gastric cancer.

In one particular embodiment, the present invention provides a method for selecting a suitable anticancer drug for the treatment of a gastric cancer, the method comprising:
(a) isolating a cancer cell after administration of an anticancer drug, or prior to incubation with an anticancer drug;
(b) lysing the isolated cell to produce a cellular extract;
(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract; and
(d) comparing the expression level and/or activation level of the one or more analytes determined in step (c) to a reference expression and/or activation profile of the one or more analytes that is generated in the absence of the anticancer drug to determine whether the anticancer drug is suitable or unsuitable for the treatment of the gastric cancer.

In another particular embodiment, the present invention provides a method for selecting a suitable anticancer drug for the treatment of a gastric cancer, the method comprising:
(a) contacting a cancer cell obtained from a sample of the gastric cancer with an anticancer drug;
(b) lysing the isolated cell to produce a cellular extract;
(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract;
(d) comparing the expression level and/or activation level of the one or more analytes determined in step (c) to a reference expression and/or activation profile of the one or more analytes that is generated in the absence of the anticancer drug; and
(e) indicating that the anticancer drug is suitable for the treatment of the gastric cancer (e.g., the gastric tumor has an increased likelihood of response to the anticancer drug) when the expression level and/or activation level determined in step (c) for the one or more analytes is changed (e.g., substantially decreased) compared to the reference expression and/or activation profile.

In certain instances, the gastric cancer is an adenocarcinoma. In certain other instances, the gastric cancer has metastazied to the esophagus, the small intestine, lymph nodes, organs, bones, or combinations thereof.

In some embodiments, the expression (e.g., total) level and/or activation (e.g., phosphorylation) level of the one or more analytes is considered to be "changed" in the presence of an anticancer drug when it is at least about 5%, 10%, 15%, 20%, 25%, 30%, 35%, 40%, 45%, 50%, 55%, 60%, 65%, 70%, 75%, 80%, 85%, 90%, or 95% more or less activated than in the absence of the anticancer drug. In other embodiments, the expression (e.g., total) level and/or activation (e.g., phosphorylation) level of the one or more analytes is considered to be "substantially decreased" in the presence of an anticancer drug when it is at least about 50%, 55%, 60%, 65%, 70%, 75%, 80%, 85%, 90%, or 95% less activated than in the absence of the anticancer drug. In further embodiments, the expression (e.g., total) level and/or activation (e.g., phosphorylation) level of the one or more analytes is considered to be "substantially decreased" in the presence of an anticancer drug (1) when there is a change from high or strong expression and/or activation of the analyte without the anticancer drug to medium, weak, low, or very weak expression and/or activation of the analyte with the anticancer drug, or (2) when there is a change from medium expression and/or activation of the analyte without the anticancer drug to weak, low, or very weak expression and/or activation of the analyte with the anticancer drug.

To preserve the in situ activation states, signal transduction proteins are typically extracted shortly after the cells are isolated, preferably within 96, 72, 48, 24, 6, or 1 hr, more preferably within 30, 15, or 5 minutes. The isolated cells may also be incubated with growth factors usually at nanomolar to micromolar concentrations for about 1-30 minutes to resuscitate or stimulate signal transducer activation (see, e.g., Irish et al., *Cell*, 118:217-228 (2004)). Stimulatory growth factors include epidermal growth factor (EGF), heregulin (HRG), TGF-α, P1GF, angiopoietin (Ang), NRG1, PGF, TNF-α, VEGF, PDGF, IGF, FGF, HGF, cytokines, and the like. To evaluate potential anticancer therapies for an individual patient, the isolated cells can be incubated with one or more anticancer drugs of varying doses prior to, during, and/or after growth factor stimulation. Growth factor stimulation can be performed for a few minutes or hours (e.g., about 1-5 minutes to about 1-6 hours). After isolation, treatment with the anticancer drug, and/or growth factor stimulation, the cells are lysed to extract the signal transduction proteins using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the lysate can be stored at −80° C. until use.

In some embodiments, the anticancer drug comprises an agent that interferes with the function of activated signal transduction pathway components in cancer cells. Non-limiting examples of such agents include those listed below in Table 1.

TABLE 1

| EGFR (ErbB1) (A) | HER-2 (ErbB2) (C) | HER-3 (ErbB3) (E) | HER-4 (ErbB4) target |
|---|---|---|---|
| Cetuximab<br>Panitumumab<br>Matuzumab<br>Nimotuzumab<br>ErbB1 vaccine | Trastuzumab<br>(Herceptin ®)<br>Pertuzumab (2C4)<br>BMS-599626*<br><br>*Heterodimerization<br>HER-1/2; Phase 1 | Antibody (U3) | |

| EGFR (ErbB1) (B) | HER-2 (ErbB2) (D) | ErbB1/2 (F) | ErbB1/2/4 (G) |
|---|---|---|---|
| Erlotinib<br>Gefitinib<br>EKB 569*<br>CL-387-785**<br>*(Wyeth, Irreversible, II CRC)<br>**(Wyeth, Irreversible, Preclinical) | CP-724714 (Pfizer) | Lapatinib (Tykerb ®)<br>HKI-272*<br>HKI-357 (Preclinical)<br>BIBW 2992**<br>*Wyeth, Irreversible, I/II NSCLC, Breast<br>**Boehringer Ingelheim, Irreversible, I/II Prostate, Ovarian, Breast | Canertinib*<br>ARRY-334543<br>JNJ-26483327<br>JNJ-26483327<br>*Pfizer, Irreversible, II NSCLC, Breast |

| Raf (H) | SRC (H) | Mek: (I) | NFkB-IkB (I) |
|---|---|---|---|
| Sorafenib<br>PLX4032 (Plexxikon) | AZ | PD-325901 (II: NSCLC)<br>AZD6244 - Array/Az<br>XL518 Exelisis/DNA | |

| mTor (J) | PI3K (J) | VEGFR2 and VEGFR1 (K) | VEGFR1/2/3: |
|---|---|---|---|
| Rad 001: Everolimus*<br>Temsirolimus<br>AP-23573*<br>*Everolimus (Novartis, combination with Gefetinib/Erlotinib; I/II: NSCLC, Glioblastoma)<br>Temsirolimus (Wyeth, combination with Gefetinib/Erlotinib; I/II: NSCLC, Glioblastoma)<br>*AP-23573 (Ariad, I/II: Endometrial) | PX-866*<br><br>*P110alpha specific inhibition; ProIX Pharma; Preclinical NSCLC | Avastin (DNA)<br>HuMV833*<br>VEGF-Trap**<br>*(PDL) anti-VEGFa<br>**Regeneron/Aventis (Receptor mimic)<br>(Phase 2) | AZD 2171 (NSCLC, CRC)<br>AMG-706 (+PDGFR) |

| VEGFR2 target (L) | | | EPH A-D |
|---|---|---|---|
| DC101*<br>IMC-IC11<br>IMC1121B Fully humanized<br>CDP-791*<br>Pazopanib****<br>*Imclone (Phase 2/3?)<br>**Chimeric IgG1 against VEGFR2 | CDP-791 (UCB)<br>CP-547632*<br>AG13736<br>E-7080 (Eisai)<br>CHIR-258*<br>OSI-930 (+cKit, PDGFR)<br>*OSI, PFIZER: (+ErbB1 + PDGFR) (NSCLC, Ovarian Phase 2) | Bay-579352 (+PDGFR)<br>ABT-869*<br>BMS-540215(+FGFR1)<br>KRN-951<br>BBIW | *(+CSF1R, Erk, Flt-3, PDGFR) |

TABLE 1-continued

| | | | |
|---|---|---|---|
| *Celltech, pegalated di-Fab antibody against R2<br>GSK, Multiple myeloma, ovarian, RCC Phase 3 enrollment completed, sarcoma II) | Pfizer: VEGFR1,2 and PDGFRbeta) (RCC II)<br>***(VEGFR1,2 FGFR3, PDGFR) | | |

| VEGFR 2/ErbB1/2 (ErbB1)/cMet/ FGFR (M) | VEGFR2/3/Raf/ PDGFR/cKit/ Flt-3 (N) | TIE 1/2 | VEGFR2/1/3, Flt-3, cFMS, PDGFR/cKit (O) |
|---|---|---|---|
| ZD6474*<br>XL647<br>AEE 788* | Sorafenib* | | PTK787 (Not cFMS, FLT-3)<br>Sunitinib<br>XL-999<br>SU-6668 (Pfizer)<br>GSK<br>AZ (AZD2171)<br>BMS<br>Novartis (AEE-788)<br>Amgen<br>Others |
| *(vandetanib) (Phase III: thyroid, NSCLC)<br>(Exelixis; Also EPHB2): (Patient resistant to Erlotinib; Asian patients) (Phase 2)<br>*(Novartis, Phase1/2) | *(RCC, HCC, NSCLC(III), Melanoma(III)) | | |

| PDGFR target (P) | Abl target: (Q) | FTL 3 | RET |
|---|---|---|---|
| Tandutinib<br>Nilotinib | Imatinib<br>Dasatinib<br>Nilotinib<br>AT-9283<br>AZD-0530<br>Bosutinib | | |

| Kit target (R) | HGFR1/2 | FGFR1-4 | IGF-1R Target (S) |
|---|---|---|---|
| AMG-706<br>XL-880<br>XL-999 | | Chiron | Merck<br>Pfizer<br>Novartis |

| HSP90 inhibitors: | Anti-Mitotic Drugs: | Other targets: |
|---|---|---|
| IPI-504*<br>17-AAG** | Docetaxel*<br>Paclitaxel<br>Vinblastine, Vincristine, Vinorelbine* | HDAC inhibitors<br>BCL2<br>Chemotherapeutics (breakdown)<br>Proteosome inhibitors |
| *(Infinity Pharma, Mutant ErbB1, I/II multiple myeloma, GIST)<br>**(Kosan, I/II solid tumors) | *(Microtubule stabilizer; Adjuvant and advanced Breast cancer; NSCLC, Androgen independent Prostate cancer)<br>(Microtubule stabilizer; Adjuvant and advanced Breast cancer; NSCLC, Ovarian cancer, AIDS related Kaposi sarcoma)<br>*(Microtubule De-stabilizers) | |

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the isolated cells are treated with one or more anti-signaling agents, anti-proliferative agents, and/or hormonal therapeutic agents in combination with at least one chemotherapeutic agent.

Examples of anti-signaling agents suitable for use in the present invention include, without limitation, monoclonal antibodies such as trastuzumab (Herceptin®), pertuzumab (2C4), alemtuzumab (Campath®), bevacizumab (Avastin®), cetuximab (Erbitux®), gemtuzumab (Mylotarg®), panitumumab (Vectibix™), rituximab (Rituxan®), and tositumomab (BEXXAR®); tyrosine kinase inhibitors such as gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ ZK222584), sorafenib (BAY 43-9006; Nexavar®), imatinib mesylate (Gleevec®), leflunomide (SU101), vandetanib (ZACTIMA™; ZD6474), pelitinib, CP-654577, CP-724714, HKI-272, PKI-166, AEE788, BMS-599626, HKI-357, BIBW 2992, ARRY-334543, JNJ-26483327, and JNJ-26483327; and combinations thereof.

Exemplary anti-proliferative agents include mTOR inhibitors such as sirolimus (rapamycin), temsirolimus (CCI-779), everolimus (RAD001), BEZ235, and XL765; AKT inhibitors such as 1L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl) methyl)-4-piperidinyl)-2H-benzimidazol-2-one, 10-(4'-(N-diethylamino)butyl)-2-chlorophenoxazine, 3-formylchromone thiosemicarbazone (Cu(II)Cl$_2$ complex), API-2, a 15-mer peptide derived from amino acids 10-24 of the proto-oncogene TCL1 (Hiromura et al., *J. Biol. Chem.,* 279:53407-53418 (2004), KP372-1, and the compounds described in Kozikowski et al., *J. Am. Chem. Soc.,* 125: 1144-1145 (2003) and Kau et al., *Cancer Cell,* 4:463-476 (2003); PI3K inhibitors such as PX-866, wortmannin, LY 294002, quercetin, tetrodotoxin citrate, thioperamide maleate, GDC-0941 (957054-30-7), IC87114, PI-103, PIK93, BEZ235 (NVP-BEZ235), TGX-115, ZSTK474, (−)-deguelin, NU 7026, myricetin, tandutinib, GDC-0941 bismesylate, GSK690693, KU-55933, MK-2206, OSU-03012, perifosine, triciribine, XL-147, PIK75, TGX-221, NU 7441, PI 828, XL-765, and WHI-P 154; MEK inhibitors such as PD98059, ARRY-162, RDEA119, U0126, GDC-0973, PD184161, AZD6244, AZD8330, PD0325901, and ARRY-142886; and combinations thereof.

Non-limiting examples of pan-HER inhibitors include PF-00299804, neratinib (HKI-272), AC480 (BMS-599626), BMS-690154, PF-02341066, HM781-36B, CI-1033, BIBW-2992, and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Examples of hormonal therapeutic agents include, without limitation, aromatase inhibitors (e.g., aminoglutethimide, anastrozole (Arimidex®), letrozole (Femara®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Non-limiting examples of cancer vaccines useful in the present invention include ANYARA from Active Biotech, DCVax-LB from Northwest Biotherapeutics, EP-2101 from IDM Pharma, GV1001 from Pharmexa, 10-2055 from Idera Pharmaceuticals, INGN 225 from Introgen Therapeutics and Stimuvax from Biomira/Merck.

Examples of radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

Non-limiting examples of compounds that modulate HER2 activity are described herein and include monoclonal antibodies, tyrosine kinase inhibitors, and combinations thereof. In preferred embodiments, the HER2-modulating compound inhibits HER2 activity and/or blocks HER2 signaling, e.g., is a HER2 inhibitor. Examples of HER2 inhibitors include, but are not limited to, monoclonal antibodies such as trastuzumab (Herceptin®) and pertuzumab (2C4); small molecule tyrosine kinase inhibitors such as gefitinib (Iressa®), erlotinib (Tarceva), pelitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327; and combinations thereof. In other embodiments, the HER2-modulating compound activates the HER2 pathway, e.g., is a HER2 activator.

Non-limiting examples of compounds that modulate c-Met activity are described herein and include monoclonal antibodies, small molecule inhibitors, and combinations thereof. In preferred embodiments, the c-Met-modulating compound inhibits c-Met activity and/or blocks c-Met signaling, e.g., is a c-Met inhibitor. Examples of c-Met inhibitors include, but are not limited to, monoclonal antibodies such as AMG102 and MetMAb; small molecule inhibitors of c-Met such as ARQ197, JNJ-38877605, PF-04217903, SGX523, GSK 1363089/XL880, XL184, MGCD265, and MK-2461; and combinations thereof. In other embodiments, the c-Met-modulating compound activates the c-Met pathway, e.g., is a c-Met activator.

In certain embodiments, the reference expression or activation level of the one or more analytes (e.g., one or more HER2 and/or c-Met signaling pathway components) determined in step (c) is obtained from a normal cell such as a non-cancerous cell from a healthy individual not having a cancer such as gastric cancer. In certain other embodiments, the reference expression or activation level of the one or more analytes (e.g., one or more HER2 and/or c-Met signaling pathway components) determined in step (c) is obtained from a tumor cell such as a gastric cancer cell from a sample from a patient with a cancer such as gastric cancer.

In some embodiments, the reference expression or activation level of the one or more analytes (e.g., one or more HER2 and/or c-Met signaling pathway components) determined in step (c) is obtained from a cell (e.g., a tumor cell such as a gastric cancer cell obtained from a patient sample) that is not treated with the anticancer drug. In particular embodiments, the cell that is not treated with the anticancer drug is obtained from the same sample that the isolated cell (e.g., a test cell to be interrogated) used to produce the cellular extract is obtained. In certain instances, the presence of a lower level of expression or activation of the one or more analytes (e.g., one or more HER2 and/or c-Met signaling pathway components) compared to the reference expression or activation level indicates that the anticancer drug is suitable for the treatment of the gastric cancer (e.g., the gastric tumor has an increased likelihood of response to the anticancer drug). In certain other instances, the presence of an identical, similar, or higher level of expression or activation of the one or more analytes (e.g., one or more HER2 and/or c-Met signaling pathway components) compared to the reference expression or activation level indicates that the anticancer drug is unsuitable for the treatment of the gastric cancer (e.g., the gastric tumor has a decreased likelihood of response to the anticancer drug).

In alternative embodiments, the reference expression or activation level of the one or more analytes (e.g., one or more HER2 and/or c-Met signaling pathway components) determined in step (c) is obtained from a cell sensitive to the anticancer drug that is treated with the anticancer drug. In such embodiments, the presence of an identical, similar, or lower level of expression or activation of the one or more analytes (e.g., one or more HER2 and/or c-Met signaling pathway components) compared to the reference expression or activation level indicates that the anticancer drug is suitable for the treatment of the gastric cancer (e.g., the gastric tumor has an increased likelihood of response to the anticancer drug). In certain other alternative embodiments, the reference expression or activation level of the one or more analytes (e.g., one or more HER2 and/or c-Met signaling pathway components) determined in step (c) is obtained from a cell resistant to the anticancer drug that is treated with the anticancer drug. In such embodiments, the presence of an identical, similar, or higher level of expression or activation of the one or more analytes (e.g., one or more HER2 and/or c-Met signaling pathway components) compared to the reference expression or activation level indicates that the anticancer drug is unsuitable for the treatment of the gastric cancer (e.g., the gastric tumor has a decreased likelihood of response to the anticancer drug).

In certain embodiments, a higher level of expression or activation of the one or more analytes (e.g., one or more HER2 and/or c-Met signaling pathway components) determined in step (c) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher) than the reference expression or activation level of the corresponding analyte in a cell (e.g., a gastric cancer cell obtained from a patient sample) not treated with the anticancer drug, in an anticancer drug-sensitive cell treated with the anticancer drug, or in an anticancer drug-resistant cell treated with the anticancer drug.

In other embodiments, a lower level of expression or activation of the one or more analytes (e.g., one or more HER2 and/or c-Met signaling pathway components) determined in step (c) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold lower) than the reference expression or activation level of the corresponding analyte in a cell (e.g., a gastric cancer cell obtained from a patient sample) not treated with the anticancer drug, in an anticancer drug-sensitive cell treated with the anticancer drug, or in an anticancer drug-resistant cell treated with the anticancer drug.

Non-limiting examples of signal transduction molecules and pathways that may be interrogated using the present invention include those shown in Table 2.

TABLE 2

| | | | | | | | |
|---|---|---|---|---|---|---|---|
| Pathway 1 | ErbB1 | ErbB1 Phospho | ErbB1 Shc | ErbB1 ubiquitin | ErbB1-PI3K | PTEN | |
| Pathway 2 | ErbB1 | ErbB1VIII | ErbB1VIII Phospho | ErbB1VIII Shc | ErbB1VIII ubiquitin | ErbB1VIII PI3K | PTEN |
| Pathway 3 | ErbB2 | ErbB2 Phospho | HER-2 Shc | ErbB2: PI3K Complex | ErbB2 ubiquitin | PTEN | |
| Pathway 4 | ErbB2 | P95Truncated ErbB2 | ErbB2Phospho | P95Truncated ERBB2 Phospho | HER-2 Shc | ERBB2: PI3K Complex | ErbB2 ubiquitin | P95ErbB2: PI3K |
| Pathway 5 | ErbB3 | ErbB3 Phospho | ErbB3: PI3K Complex | ErbB3 PI3K Phospho | ErbB3: Shc | | |
| Pathway 6 | ErbB4 | ErbB4 Phospho | ErbB4: Shc | | | | |
| Pathway 7 | IGF-1R | IGF-1RPhospho | IGF-1R: IRS | IRS: PI3K | Phospho IRS | IGF-1R: PI3K | |
| Pathway 8 | INSR | INSRPhospho | | | | | |
| Pathway 9 | KIT | KIT Phospho | | | | | |
| Pathway 10 | FLT3 | FLT3Phospho | | | | | |
| Pathway 11 | HGFR 1 | HGFR 1 Phospho | | | | | |
| Pathway 12 | HGFR 2 | HGFR 2 Phospho | | | | | |
| Pathway 13 | RET | RET Phospho | | | | | |
| Pathway 14 | PDGFR alpha | PDGFR alpha Phospho | | | | | |
| Pathway 15 | PDGFR beta | PDGFR beta Phospho | | | | | |
| Pathway 16 | VEGFR 1 | VEGFR 1 Phospho | VEGFR 1: PLCγcomplex | VEGFR 1: Src | | | |
| Pathway 17 | VEGFR 2 | VEGFR 2 Phospho | VEGFR 2: PLCγ complex | VEGFR 2: Src | VEGFR-2/ heparin sulphate complex | VEGFR-2, VE-cadherin complex | |
| Pathway 18 | VEGFR 3 | VEGFR 3 Phospho | | | | | |
| Pathway 19 | FGFR 1 | FGFR 1 Phospho | | | | | |
| Pathway 20 | FGFR 2 | FGFR 2 Phospho | | | | | |
| Pathway 21 | FGFR 3 | FGFR 3 Phospho | | | | | |
| Pathway 22 | FGFR 4 | FGFR 4 Phospho | | | | | |
| Pathway 23 | TIE 1 | TIE 1 Phospho | | | | | |
| Pathway 24 | TIE 2 | TIE 2 Phospho | | | | | |
| Pathway 25 | EPHA | EPHA Phospho | | | | | |

TABLE 2-continued

| | | | | | | | | |
|---|---|---|---|---|---|---|---|---|
| Pathway 26 | EPHB | EPHB Phospho | | | | | | |
| Pathway 27 | NFkB-IkB complex | phospho-IκB (S32) Total IkB | Total NFκB Phospho NFκB(S536) | Total P65 IkBa Phospho P65 IkBa | | | | |
| Pathway 28 | ER | Phospho ER | ER-AIB1 | Other ER complexes | | | | |
| Pathway 29 | PR | Phospho Pr | | PR complexes | | | | |
| Pathway 30 | Hedgehog Pathway | | | | | | | |
| Pathway 31 | Wnt pathway | | | | | | | |
| Pathway 32 | Notch Pathway | | | | | | | |
| Pathway 33 | Total Mek Phospho Mek (S217/S221) | Total Erk Phospho Erk (T202/Y204) | Total Rsk-1 Phospho Rsk-1 (T357/S363) | Total Stat3 Phospho Stat-3 (Y705) (S727) Total Stat 1 Phospho Stat1 (Y 701) | Phospho Bad (S112) Bad (total) | Total Fak Phospho Fak (Y576) | Total cSrc Phospho cSrc(Y416) | Total Ras Phospho Ras |
| Pathway 34 | Akt (Total) Phospho Akt (T473) | Phospho Akt (T308) | Phospho Bad (S112) Bad (total) | Phospho Bad (S136) | Bad: 14-3-3 complex | Total mTor Phospho mTor (S2448) | Total p70S6K Phospho p70S6K (T229) (T389) | GSK3beta Total (Phospho Ser 9) |
| Pathway 35 | Total Jnk Phospho Jnk (T183/Y185) | Total P38 Phospho P38 (T180/Y182) | Total Rb Phospho Rb (S249/T252) Phospho Rb (S780) | Total p53 Phospho p53 (S392) Phospho p53 (S20) | phospho-CREB(S133) Total CREB | Total c-Jun phospho-c-Jun; (S63) | Total Paxillin Phospho Paxillin (Y118) | |
| Pathway 36 | Ki67 | Cleaved Caspase 3, 8, 9 others | TOPO2 | | | | | |
| Pathway 37 | TGFbeta | | | | | | | |

Non-limiting examples of analytes such as signal transduction molecules that can be interrogated for expression (e.g., total amount) levels and/or activation (e.g., phosphorylation) levels in a cellular extract include receptor tyrosine kinases, non-receptor tyrosine kinases, tyrosine kinase signaling cascade components, nuclear hormone receptors, nuclear receptor coactivators, nuclear receptor repressors, and combinations thereof.

In one embodiment, the methods of the present invention comprise determining the expression (e.g., total amount) level and/or activation (e.g., phosphorylation) level of one of the following analytes in a cellular extract: (1) HER1/EGFR/ErbB1; (2) HER2/ErbB2; (3) p95HER2; (4) HER3/ErbB3; (5) c-Met; (6) IGF1R; (7) cKit; (8) PI3K (e.g., PIK3CA and/or PIK3R1); (9) Shc; (10) Akt; (11) p70S6K; (12) VEGFR (e.g., VEGFR1, VEGFR2, and/or VEGFR3); and (13) PDGFR (e.g., PDGFRA and/or PDGFRB).

In another embodiment, the present invention comprises determining the expression (e.g., total) level and/or activation (e.g., phosphorylation) level of one of the following pairs of two analytes in a cellular extract, wherein "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B): 1, 2; 1, 3; 1, 4; 1, 5; 1, 6; 1, 7; 1, 8; 1, 9; 1, 10; 1, 11; 1, 12; 1, 13; 2, 3; 2, 4; 2, 5; 2, 6; 2, 7; 2, 8; 2, 9; 2, 10; 2, 11; 2, 12; 2, 13; 3, 4; 3, 5; 3, 6; 3, 7; 3, 8; 3, 9; 3, 10; 3, 11; 3, 12; 3, 13; 4, 5; 4, 6; 4, 7; 4, 8; 4, 9; 4, 10; 4, 11; 4, 12; 4, 13; 5, 6; 5, 7; 5, 8; 5, 9; 5, 10; 5, 11; 5, 12; 5, 13; 6, 7; 6, 8; 6, 9; 6, 10; 6, 11; 6, 12; 6, 13; 7, 8; 7, 9; 7, 10; 7, 11; 7, 12; 7, 13; 8, 9; 8, 10; 8, 11; 8, 12; 8, 13; 9, 10; 9, 11; 9, 12; 9, 13; 10, 11; 10, 12; 10, 13; 11, 12; 11, 13; and 12, 13.

In yet another embodiment, the present invention comprises determining the expression (e.g., total) level and/or activation (e.g., phosphorylation) level of one of the following sets of three analytes in a cellular extract, wherein "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B): 1, 2, 3; 1, 2, 4; 1, 2, 5; 1, 2, 6; 1, 2, 7; 1, 2, 8; 1, 2, 9; 1, 2, 10; 1, 2, 11; 1, 2, 12; 1, 2, 13; 1, 3, 4; 1, 3, 5; 1, 3, 6; 1, 3, 7; 1, 3, 8; 1, 3, 9; 1, 3, 10; 1, 3, 11; 1, 3, 12; 1, 3, 13; 1, 4, 5; 1, 4, 6; 1, 4, 7; 1, 4, 8; 1, 4, 9; 1, 4, 10; 1, 4, 11; 1, 4, 12; 1, 4, 13; 1, 5, 6; 1, 5, 7; 1, 5, 8; 1, 5, 9; 1, 5, 10; 1, 5, 11; 1, 5, 12; 1, 5, 13; 1, 6, 7; 1, 6, 8; 1, 6, 9; 1, 6, 10; 1, 6, 11; 1, 6, 12; 1, 6, 13; 1, 7, 8; 1, 7, 9; 1, 7, 10; 1, 7, 11; 1, 7, 12; 1, 7, 13; 1, 8, 9; 1, 8, 10; 1, 8, 11; 1, 8, 12; 1, 8, 13; 1, 9, 10; 1, 9, 11; 1, 9, 12; 1, 9, 13; 1, 10, 11; 1, 10, 12; 1, 10, 13; 1, 11, 12; 1, 11, 13; 1, 12, 13; 2, 3, 4; 2, 3, 5; 2, 3, 6; 2, 3, 7; 2, 3, 8; 2, 3, 9; 2, 3, 10; 2, 3, 11; 2, 3, 12; 2, 3, 13; 2, 4, 5; 2, 4, 6; 2, 4, 7; 2, 4, 8; 2, 4, 9; 2, 4, 10; 2, 4, 11; 2, 4, 12; 2, 4, 13; 2, 5, 6; 2, 5, 7; 2, 5, 8; 2, 5, 9; 2, 5, 10; 2, 5, 11; 2, 5, 12; 2, 5, 13; 2, 6, 7; 2, 6, 8; 2, 6, 9; 2, 6, 10; 2, 6, 11; 2, 6, 12; 2, 6, 13; 2, 7, 8; 2, 7, 9; 2, 7, 10; 2, 7, 11; 2, 7, 12; 2, 7, 13; 2, 8, 9; 2, 8, 10; 2, 8, 11; 2, 8, 12; 2, 8, 13; 2, 9, 10; 2, 9, 11; 2, 9, 12; 2, 9, 13; 2, 10, 11; 2, 10, 12; 2, 10, 13; 2, 11, 12; 2, 11, 13; 2, 12, 13; 3, 4, 5; 3, 4, 6; 3, 4, 7; 3, 4, 8; 3, 4, 9; 3, 4, 10; 3, 4, 11; 3, 4, 12; 3, 4, 13; 3, 5, 6; 3, 5, 7; 3, 5, 8; 3, 5, 9; 3, 5, 10; 3, 5, 11; 3, 5, 12; 3, 5, 13; 3, 6, 7; 3, 6, 8; 3, 6, 9; 3, 6, 10; 3, 6, 11; 3, 6, 12; 3, 6, 13; 3, 7, 8; 3, 7, 9; 3, 7, 10; 3, 7, 11; 3, 7, 12; 3, 7, 13; 3, 8, 9; 3, 8, 10; 3, 8, 11; 3, 8, 12; 3, 8, 13; 3, 9, 10; 3, 9, 11; 3, 9, 12; 3, 9, 13; 3, 10, 11; 3, 10, 12; 3, 10, 13; 3, 11, 12; 3, 11, 13; 3, 12, 13; 4, 5, 6; 4, 5, 7; 4, 5, 8; 4, 5, 9; 4, 5, 10; 4, 5, 11; 4, 5, 12; 4, 5, 13; 4, 6, 7; 4, 6, 8; 4, 6, 9; 4, 6, 10; 4, 6, 11; 4, 6, 12; 4, 6, 13; 4, 7, 8; 4, 7, 9; 4, 7, 10; 4, 7, 11; 4, 7, 12; 4, 7, 13; 4, 8, 9; 4, 8, 10; 4, 8, 11; 4, 8, 12; 4, 8, 13; 4, 9, 10; 4, 9, 11; 4, 9, 12; 4, 9, 13; 4, 10, 11; 4, 10, 12; 4, 10, 13; 4, 11, 12; 4, 11, 13; 4, 12, 13; 5, 6, 7; 5, 6, 8; 5, 6, 9; 5, 6, 10; 5, 6, 11; 5, 6, 12; 5, 6, 13; 5, 7, 8; 5, 7, 9; 5, 7, 10; 5, 7, 11; 5, 7, 12; 5, 7, 13; 5, 8, 9; 5, 8, 10; 5, 8, 11; 5, 8, 12; 5, 8, 13; 5, 9, 10; 5, 9, 11; 5, 9, 12; 5, 9, 13; 5, 10, 11; 5, 10, 12; 5, 10, 13; 5, 11, 12; 5, 11, 13; 5, 12, 13; 6, 7, 8; 6, 7, 9; 6, 7, 10; 6, 7, 11; 6, 7, 12; 6, 7, 13; 6, 8, 9; 6, 8, 10; 6, 8, 11; 6, 8, 12; 6, 8, 13;

6, 9, 10; 6, 9, 11; 6, 9, 12; 6, 9, 13; 6, 10, 11; 6, 10, 12; 6, 10, 13; 6, 11, 12; 6, 11, 13; 6, 12, 13; 7, 8, 9; 7, 8, 10; 7, 8, 11; 7, 8, 12; 7, 8, 13; 7, 9, 10; 7, 9, 11; 7, 9, 12; 7, 9, 13; 7, 10, 11; 7, 10, 12; 7, 10, 13; 7, 11, 12; 7, 11, 13; 7, 12, 13; 8, 9, 10; 8, 9, 11; 8, 9, 12; 8, 9, 13; 8, 10, 11; 8, 10, 12; 8, 10, 13; 8, 11, 12; 8, 11, 13; 8, 12, 13; 9, 10, 11; 9, 10, 12; 9, 10, 13; 9, 11, 12; 9, 11, 13; 9, 12, 13; 10, 11, 12; 10, 11, 13; 10, 12, 13; and 11, 12, 13.

In still yet another embodiment, the present invention comprises determining the expression (e.g., total) level and/or activation (e.g., phosphorylation) level of one of the following sets of four analytes in a cellular extract, wherein "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B): 1, 2, 3, 4; 1, 2, 3, 5; 1, 2, 3, 6; 1, 2, 3, 7; 1, 2, 3, 8; 1, 2, 3, 9; 1, 2, 3, 10; 1, 2, 3, 11; 1, 2, 3, 12; 1, 2, 3, 13; 1, 3, 4, 5; 1, 3, 4, 6; 1, 3, 4, 7; 1, 3, 4, 8; 1, 3, 4, 9; 1, 3, 4, 10; 1, 3, 4, 11; 1, 3, 4, 12; 1, 3, 4, 13; 1, 4, 5, 6; 1, 4, 5, 7; 1, 4, 5, 8; 1, 4, 5, 9; 1, 4, 5, 10; 1, 4, 5, 11; 1, 4, 5, 12; 1, 4, 5, 13; 1, 5, 6, 7; 1, 5, 6, 8; 1, 5, 6, 9; 1, 5, 6, 10; 1, 5, 6, 11; 1, 5, 6, 12; 1, 5, 6, 13; 1, 6, 7, 8; 1, 6, 7, 9; 1, 6, 7, 10; 1, 6, 7, 11; 1, 6, 7, 12; 1, 6, 7, 13; 1, 7, 8, 9; 1, 7, 8, 10; 1, 7, 8, 11; 1, 7, 8, 12; 1, 7, 8, 13; 1, 8, 9, 10; 1, 8, 9, 11; 1, 8, 9, 12; 1, 8, 9, 13; 1, 9, 10, 11; 1, 9, 10, 12; 1, 9, 10, 13; 1, 10, 11, 12; 1, 10, 11, 13; 1, 11, 12, 13; 2, 3, 4, 5; 2, 3, 4, 6; 2, 3, 4, 7; 2, 3, 4, 8; 2, 3, 4, 9; 2, 3, 4, 10; 2, 3, 4, 11; 2, 3, 4, 12; 2, 3, 4, 13; 2, 4, 5, 6; 2, 4, 5, 7; 2, 4, 5, 8; 2, 4, 5, 9; 2, 4, 5, 10; 2, 4, 5, 11; 2, 4, 5, 12; 2, 4, 5, 13; 2, 5, 6, 7; 2, 5, 6, 8; 2, 5, 6, 9; 2, 5, 6, 10; 2, 5, 6, 11; 2, 5, 6, 12; 2, 5, 6, 13; 2, 6, 7, 8; 2, 6, 7, 9; 2, 6, 7, 10; 2, 6, 7, 11; 2, 6, 7, 12; 2, 6, 7, 13; 2, 7, 8, 9; 2, 7, 8, 10; 2, 7, 8, 11; 2, 7, 8, 12; 2, 7, 8, 13; 2, 8, 9, 10; 2, 8, 9, 11; 2, 8, 9, 12; 2, 8, 9, 13; 2, 9, 10, 11; 2, 9, 10, 12; 2, 9, 10, 13; 2, 10, 11, 12; 2, 10, 11, 13; 2, 11, 12, 13; 3, 4, 5, 6; 3, 4, 5, 7; 3, 4, 5, 8; 3, 4, 5, 9; 3, 4, 5, 10; 3, 4, 5, 11; 3, 4, 5, 12; 3, 4, 5, 13; 3, 5, 6, 7; 3, 5, 6, 8; 3, 5, 6, 9; 3, 5, 6, 10; 3, 5, 6, 11; 3, 5, 6, 12; 3, 5, 6, 13; 3, 6, 7, 8; 3, 6, 7, 9; 3, 6, 7, 10; 3, 6, 7, 11; 3, 6, 7, 12; 3, 6, 7, 13; 3, 7, 8, 9; 3, 7, 8, 10; 3, 7, 8, 11; 3, 7, 8, 12; 3, 7, 8, 13; 3, 8, 9, 10; 3, 8, 9, 11; 3, 8, 9, 12; 3, 8, 9, 13; 3, 9, 10, 11; 3, 9, 10, 12; 3, 9, 10, 13; 3, 10, 11, 12; 3, 10, 11, 13; 3, 11, 12, 13; 4, 5, 6, 7; 4, 5, 6, 8; 4, 5, 6, 9; 4, 5, 6, 10; 4, 5, 6, 11; 4, 5, 6, 12; 4, 5, 6, 13; 4, 6, 7, 8; 4, 6, 7, 9; 4, 6, 7, 10; 4, 6, 7, 11; 4, 6, 7, 12; 4, 6, 7, 13; 4, 7, 8, 9; 4, 7, 8, 10; 4, 7, 8, 11; 4, 7, 8, 12; 4, 7, 8, 13; 4, 8, 9, 10; 4, 8, 9, 11; 4, 8, 9, 12; 4, 8, 9, 13; 4, 9, 10, 11; 4, 9, 10, 12; 4, 9, 10, 13; 4, 10, 11, 12; 4, 10, 11, 13; 4, 11, 12, 13; 5, 6, 7, 8; 5, 6, 7, 9; 5, 6, 7, 10; 5, 6, 7, 11; 5, 6, 7, 12; 5, 6, 7, 13; 5, 7, 8, 9; 5, 7, 8, 10; 5, 7, 8, 11; 5, 7, 8, 12; 5, 7, 8, 13; 5, 8, 9, 10; 5, 8, 9, 11; 5, 8, 9, 12; 5, 8, 9, 13; 5, 9, 10, 11; 5, 9, 10, 12; 5, 9, 10, 13; 5, 10, 11, 12; 5, 10, 11, 13; 5, 11, 12, 13; 6, 7, 8, 9; 6, 7, 8, 10; 6, 7, 8, 11; 6, 7, 8, 12; 6, 7, 8, 13; 6, 8, 9, 10; 6, 8, 9, 11; 6, 8, 9, 12; 6, 8, 9, 13; 6, 9, 10, 11; 6, 9, 10, 12; 6, 9, 10, 13; 6, 10, 11, 12; 6, 10, 11, 13; 6, 11, 12, 13; 7, 8, 9, 10; 7, 8, 9, 11; 7, 8, 9, 12; 7, 8, 9, 13; 7, 9, 10, 11; 7, 9, 10, 12; 7, 9, 10, 13; 7, 10, 11, 12; 7, 10, 11, 13; 7, 11, 12, 13; 8, 9, 10, 11; 8, 9, 10, 12; 8, 9, 10, 13; 8, 10, 11, 12; 8, 10, 11, 13; 8, 11, 12, 13; 9, 10, 11, 12; 9, 10, 11, 13; 9, 11, 12, 13; and 10, 11, 12, 13.

In another embodiment, the present invention comprises determining the expression (e.g., total) level and/or activation (e.g., phosphorylation) level of any possible combination of five of the following analytes: "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B). As non-limiting examples, the combination of five analytes may comprise one of the following: 1, 2, 3, 4, 5; 2, 3, 4, 5, 6; 3, 4, 5, 6, 7; 4, 5, 6, 7, 8; 5, 6, 7, 8, 9; 6, 7, 8, 9, 10; 7, 8, 9, 10, 11; 8, 9, 10, 11, 12; or 9, 10, 11, 12, 13.

In yet another embodiment, the present invention comprises determining the expression (e.g., total) level and/or activation (e.g., phosphorylation) level of any possible combination of six of the following analytes: "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B). As non-limiting examples, the combination of six analytes may comprise one of the following: 1, 2, 3, 4, 5, 6; 2, 3, 4, 5, 6, 7; 3, 4, 5, 6, 7, 8; 4, 5, 6, 7, 8, 9; 5, 6, 7, 8, 9, 10; 6, 7, 8, 9, 10, 11; 7, 8, 9, 10, 11, 12; or 8, 9, 10, 11, 12, 13.

In still yet another embodiment, the present invention comprises determining the expression (e.g., total) level and/or activation (e.g., phosphorylation) level of any possible combination of seven of the following analytes: "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B). As non-limiting examples, the combination of seven analytes may comprise one of the following: 1, 2, 3, 4, 5, 6, 7; 2, 3, 4, 5, 6, 7, 8; 3, 4, 5, 6, 7, 8, 9; 4, 5, 6, 7, 8, 9, 10; 5, 6, 7, 8, 9, 10, 11; 6, 7, 8, 9, 10, 11, 12; or 7, 8, 9, 10, 11, 12, 13.

In another embodiment, the present invention comprises determining the expression (e.g., total) level and/or activation (e.g., phosphorylation) level of any possible combination of eight of the following analytes: "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B). As non-limiting examples, the combination of eight analytes may comprise one of the following: 1, 2, 3, 4, 5, 6, 7, 8; 2, 3, 4, 5, 6, 7, 8, 9; 3, 4, 5, 6, 7, 8, 9, 10; 4, 5, 6, 7, 8, 9, 10, 11; 5, 6, 7, 8, 9, 10, 11, 12; or 6, 7, 8, 9, 10, 11, 12, 13.

In yet another embodiment, the present invention comprises determining the expression (e.g., total) level and/or activation (e.g., phosphorylation) level of any possible combination of nine of the following analytes: "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B). As non-limiting examples, the combination of nine analytes may comprise one of the following: 1, 2, 3, 4, 5, 6, 7, 8, 9; 2, 3, 4, 5, 6, 7, 8, 9, 10; 3, 4, 5, 6, 7, 8, 9, 10, 11; 4, 5, 6, 7, 8, 9, 10, 11, 12; or 5, 6, 7, 8, 9, 10, 11, 12, 13.

In still yet another embodiment, the present invention comprises determining the expression (e.g., total) level and/or activation (e.g., phosphorylation) level of any possible combination of ten of the following analytes: "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B). As non-limiting examples, the combination of ten analytes may comprise one of the following: 1, 2, 3, 4, 5, 6, 7, 8, 9, 10; 2, 3, 4, 5, 6, 7, 8, 9, 10, 11; 3, 4, 5, 6, 7, 8, 9, 10, 11, 12; or 4, 5, 6, 7, 8, 9, 10, 11, 12, 13.

In another embodiment, the present invention comprises determining the expression (e.g., total) level and/or activation (e.g., phosphorylation) level of any possible combination of eleven of the following analytes: "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B). As non-limiting examples, the combination of eleven analytes may comprise one of the following: 1, 2, 3, 4, 5, 6, 7, 8, 9, 10, 11; 2, 3, 4, 5, 6, 7, 8, 9, 10, 11, 12; or 3, 4, 5, 6, 7, 8, 9, 10, 11, 12, 13.

In yet another embodiment, the present invention comprises determining the expression (e.g., total) level and/or activation (e.g., phosphorylation) level of any possible combination of twelve of the following analytes: "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B). As non-limiting examples, the combination of twelve analytes may comprise one of the following:
1, 2, 3, 4, 5, 6, 7, 8, 9, 10, 11, 12; or 2, 3, 4, 5, 6, 7, 8, 9, 10, 11, 12, 13.

In still yet another embodiment, the present invention comprises determining the expression (e.g., total) level and/or activation (e.g., phosphorylation) level of all thirteen of the following analytes: "1"=HER1, "2"=HER2, "3"=p95HER2, "4"=HER3, "5"=c-Met, "6"=IGF1R, "7"=cKit, "8"=PI3K (e.g., PIK3CA and/or PIK3R1), "9"=Shc, "10"=Akt, "11"=p70S6K, "12"=VEGFR (e.g., VEGFR1, 2, and/or 3), and "13"=PDGFR (e.g., PDGFRA and/or B).

In one particular embodiment, the present invention comprises determining the expression (e.g., total) level and/or activation (e.g., phosphorylation) level of HER1, HER2, p95HER2, and HER3. In another particular embodiment, the present invention comprises determining the expression (e.g., total) level and/or activation (e.g., phosphorylation) level of HER1, HER2, HER3, c-Met, IGF1R, cKit, PI3K (e.g., PIK3CA and/or PIK3R1), and Shc. In yet another particular embodiment, the present invention comprises determining the expression (e.g., total) level and/or activation (e.g., phosphorylation) level of HER1, HER2, p95HER2, HER3, c-Met, IGF1R, cKit, PI3K (e.g., PIK3CA and/or PIK3R1), Shc, Akt, p70S6K, VEGFR (e.g., VEGFR1, 2, and/or 3), and PDGFR (e.g., PDGFRA and/or B).

In certain embodiments, the present invention further comprises determining the expression (e.g., total) level and/or activation (e.g., phosphorylation) level of one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) additional analytes in the cellular extract. In some embodiments, the one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) additional analytes comprises one or more signal transduction molecules selected from the group consisting of receptor tyrosine kinases, non-receptor tyrosine kinases, tyrosine kinase signaling cascade components, nuclear hormone receptors, nuclear receptor coactivators, nuclear receptor repressors, and combinations thereof.

In particular embodiments, the present invention further comprises determining the expression (e.g., total) level and/or activation (e.g., phosphorylation) level of one or any combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more of the following additional analytes in a cellular extract: HER4, MEK, PTEN, SGK3, 4E-BP1, ERK2 (MAPK1), ERK1 (MAPK3), PDK1, PDK2, GSK-3β, Raf, SRC, NFkB-IkB, mTOR, EPH-A, EPH-B, EPH-C, EPH-D, FLT-3, TIE-1, TIE-2, c-FMS, Abl, FTL 3, RET, FGFR1, FGFR2, FGFR3, FGFR4, ER, PR, NCOR, AIB1, RON, PIP2, PIP3, p27, protein tyrosine phosphatases (e.g., PTP1B, PTPN13, BDP1, etc.), receptor dimers, other HER2 signaling pathway components, other c-Met signaling pathway components, and combinations thereof.

In some embodiments, the cell (e.g., the test cell from which a cellular extract is produced) is a tumor cell such as a gastric cancer cell. In certain instances, the tumor cell is a circulating tumor cell or a fine needle aspirate (FNA) cell obtained from a tumor. In other embodiments, the cell (e.g., the test cell from which a cellular extract is produced) is isolated from a sample that is obtained, e.g., from a gastric cancer patient. Non-limiting examples of samples include bodily fluid samples such as, for example, a whole blood, serum, plasma, ductal lavage fluid, nipple aspirate, lymph, bone marrow aspirate, urine, saliva, and/or fine needle aspirate (FNA) sample. In particular embodiments, the sample comprises a whole blood, serum, plasma, and/or tumor tissue sample such as gastric tumor tissue.

In certain instances, the methods of the present invention may further comprise a step of providing the result of the comparison obtained in step (d) to a user (e.g., a clinician such as an oncologist or a general practitioner) in a readable format. In some instances, the method may further comprise sending or reporting the result of the comparison obtained in step (d) to a clinician, e.g., an oncologist or a general practitioner. In other instances, the method may further comprise recording or storing the result of the comparison obtained in step (d) in a computer database or other suitable machine or device for storing information, e.g., at a laboratory.

In some embodiments, determining the expression level of the one or more analytes (e.g., one or more HER2 and/or c-Met signaling pathway components) in step (c) comprises detecting the total amount of the one or more analytes in the cellular extract with one or more antibodies specific for the corresponding analyte. In particular embodiments, the antibodies bind to the analyte irrespective of the activation state of the analyte to be detected, i.e., the antibodies detect both the non-activated and activated forms of the analyte.

Total expression level and/or status can be determined using any of a variety of techniques. In certain embodiments, the expression level and/or status of one or more analytes such as signal transduction molecules in a sample is detected with an immunoassay such as a single detection assay or a proximity dual detection assay (e.g., a COllaborative Proximity ImmunoAssay (COPIA)) as described herein.

In certain embodiments, determining the expression (e.g., total) levels of the one or more analytes (e.g., one or more HER2 and/or c-MET signaling pathway components) in step (c) comprises:
(i) incubating (e.g., contacting) the cellular extract with one or a plurality of dilution series of capture antibodies (e.g., capture antibodies specific for one or more HER2 and/or c-MET signaling pathway components) to form a plurality of captured analytes, wherein the capture antibodies are restrained on a solid support (e.g., to transform the analytes present in the cellular extract into complexes of captured analytes comprising the analytes and capture antibodies);

(ii) incubating (e.g., contacting) the plurality of captured analytes with detection antibodies comprising one or a plurality of first and second activation state-independent antibodies specific for the corresponding analytes (e.g., first and second activation state-independent antibodies specific for the one or more HER2 and/or c-MET signaling pathway components) to form a plurality of detectable captured analytes (e.g., to transform the complexes of captured analytes into complexes of detectable captured analytes comprising the captured analytes and detection antibodies), wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(iii) incubating (e.g., contacting) the plurality of detectable captured analytes with a second member of the signal amplification pair to generate an amplified signal; and (iv) detecting the amplified signal generated from the first and second members of the signal amplification pair.

In certain other embodiments, determining the expression (e.g., total) levels of the one or more analytes in step (c) that are truncated receptors (e.g., p95HER2) comprises:

(i) incubating (e.g., contacting) the cellular extract with a plurality of beads specific for an extracellular domain (ECD) binding region of a full-length receptor (e.g., full-length HER2);

(ii) removing the plurality of beads from the cellular extract, thereby removing the full-length receptor (e.g., full-length HER2) to form a cellular extract devoid of the full-length receptor (e.g., full-length HER2) (e.g., to transform the cellular extract into a cellular extract devoid of a specific full-length receptor or family of full-length receptors);

(iii) incubating (e.g., contacting) the cellular extract devoid of the full-length receptor (e.g., full-length HER2) with one or a plurality of capture antibodies specific for an intracellular domain (ICD) binding region of the full-length receptor (e.g., full-length HER2) to form a plurality of captured truncated receptors, wherein the capture antibodies are restrained on a solid support (e.g., to transform the truncated receptors present in a full-length receptor-depleted cellular extract into complexes of truncated receptors and capture antibodies);

(iv) incubating the plurality of captured truncated receptors with detection antibodies comprising one or a plurality of first and second activation state-independent antibodies specific for an ICD binding region of the full-length receptor (e.g., full-length HER2) to form a plurality of detectable captured truncated receptors (e.g., to transform the complexes of captured truncated receptors into complexes of detectable captured truncated receptors comprising the captured truncated receptors and detection antibodies), wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(v) incubating (e.g., contacting) the plurality of detectable captured truncated receptors with a second member of the signal amplification pair to generate an amplified signal; and (vi) detecting the amplified signal generated from the first and second members of the signal amplification pair.

The first activation state-independent antibodies may be directly labeled with the facilitating moiety or indirectly labeled with the facilitating moiety, e.g., via hybridization between an oligonucleotide conjugated to the first activation state-independent antibodies and a complementary oligonucleotide conjugated to the facilitating moiety. Similarly, the second activation state-independent antibodies may be directly labeled with the first member of the signal amplification pair or indirectly labeled with the first member of the signal amplification pair, e.g., via binding between a first member of a binding pair conjugated to the second activation state-independent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the first activation state-independent antibodies can be conjugated to a sulfhydryl-activated dextran molecule as described in, e.g., Examples 16-17 of PCT Publication No. WO2009/108637, the disclosure of which is herein incorporated by reference in its entirety for all purposes. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, for example, a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the second activation state-independent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

The truncated receptor is typically a fragment of the full-length receptor and shares an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated receptor with a shortened ECD or a truncated receptor comprising a membrane-associated or cytosolic ICD fragment.

In certain preferred embodiments, the truncated receptor is p95HER2 and the corresponding full-length receptor is HER2. However, one skilled in the art will appreciate that the methods described herein for detecting truncated proteins can be applied to a number of different proteins including, but not limited to, the EGFR VIII mutant (implicated in glioblastoma, colorectal cancer, etc.), other truncated receptor tyrosine kinases, caspases, and the like. Example 12 of PCT Publication No. WO2009/108637, the disclosure of which is herein incorporated by reference in its entirety for all purposes, provides an exemplary embodiment of the assay methods of the present invention for detecting truncated receptors such as p95HER2 in cells using a multiplex, high-throughput, proximity dual detection microarray ELISA having superior dynamic range.

In some embodiments, the plurality of beads specific for an ECD binding region comprises a streptavidin-biotin pair, wherein the streptavidin is attached to the bead and the biotin is attached to an antibody. In certain instances, the antibody is specific for the ECD binding region of the full-length receptor (e.g., full-length HER2).

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto an array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.).

In further embodiments, determining the activation levels of the one or more analytes (e.g., one or more HER2 and/or c-Met signaling pathway components) in step (c) comprises detecting a phosphorylation level of the one or more analytes in the cellular extract with antibodies specific for the phosphorylated form of each of the analytes to be detected.

Phosphorylation levels and/or status can be determined using any of a variety of techniques. For example, it is well known in the art that phosphorylated proteins can be detected via immunoassays using antibodies that specifically recognize the phosphorylated form of the protein (see, e.g., Lin et al., *Br. J. Cancer*, 93:1372-1381 (2005)). Immunoassays generally include immunoblotting (e.g., Western blotting), RIA, and ELISA. More specific types of immunoassays include antigen capture/antigen competition, antibody capture/antigen competition, two-antibody sandwiches, antibody capture/antibody excess, and antibody capture/antigen excess. Methods of making antibodies are described herein and in Harlow and Lane, Antibodies: A Laboratory Manual, 1988, Cold Spring Harbor Laboratory Press, Cold Spring Harbor, N.Y., USA. Phospho-specifc antibodies can be made de novo or obtained from commercial or noncommercial sources. Phosphorylation levels and/or status can also be determined by metabolically labeling cells with radioactive phosphate in the form of $[\gamma-{}^{32}P]ATP$ or $[\gamma-{}^{33}P]ATP$. Phosphorylated proteins become radioactive and hence traceable and quantifiable through scintillation counting, radiography, and the like (see, e.g., Wang et al., *J. Biol. Chem.*, 253:7605-7608 (1978)). For example, metabolically labeled proteins can be extracted from cells, separated by gel electrophoresis, transferred to a membrane, probed with an antibody specific for a particular HER2 signaling pathway component and subjected to autoradiography to detect $^{32}P$ or $^{33}P$. Alternatively, the gel can be subjected to autoradiography prior to membrane transference and antibody probing.

In particular embodiments, the activation (e.g., phosphorylation) level and/or status of the one or more analytes (e.g., one or more HER2 and/or c-Met signaling pathway components) in step (c) is detected with an immunoassay such as a single detection assay or a proximity dual detection assay (e.g., a COllaborative Proximity ImmunoAssay (COPIA)) as described herein.

In certain embodiments, determining the activation (e.g., phosphorylation) level of the one or more analytes (e.g., one or more components of the HER2 and/or c-Met signaling pathways) in step (c) comprises:

(i) incubating (e.g., contacting) the cellular extract with a dilution series of capture antibodies (e.g., capture antibodies specific for one or more HER2 and/or c-Met signaling pathway components) to form a plurality of captured analytes, wherein the capture antibodies are restrained on a solid support (e.g., to transform the analytes present in the cellular extract into complexes of captured analytes comprising the analytes and capture antibodies);

(ii) incubating (e.g., contacting) the plurality of captured analytes with detection antibodies comprising activation state-independent antibodies specific for the corresponding analytes (e.g., activation state-independent antibodies specific for the one or more HER2 and/or c-Met signaling pathway components) and activation state-dependent antibodies specific for the corresponding analytes (e.g., activation state-dependent antibodies specific for the one or more HER2 and/or c-Met signaling pathway components) to form a plurality of detectable captured analytes (e.g., to transform the complexes of captured analytes into complexes of detectable captured analytes comprising the captured analytes and detection antibodies), wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(iii) incubating (e.g., contacting) the plurality of detectable captured analytes with a second member of the signal amplification pair to generate an amplified signal; and (iv) detecting the amplified signal generated from the first and second members of the signal amplification pair.

In certain other embodiments, determining the activation (e.g., phosphorylation) level of the one or more analytes in step (c) that are truncated receptors (e.g., p95HER2) comprises:

(i) incubating (e.g., contacting) the cellular extract with a plurality of beads specific for an extracellular domain (ECD) binding region of a full-length receptor (e.g., full-length HER2);

(ii) removing the plurality of beads from the cellular extract, thereby removing the full-length receptor (e.g., full-length HER2) to form a cellular extract devoid of the full-length receptor (e.g., full-length HER2) (e.g., to transform the cellular extract into a cellular extract devoid of a specific full-length receptor or family of full-length receptors);

(iii) incubating (e.g., contacting) the cellular extract devoid of the full-length receptor (e.g., full-length HER2) with a plurality of capture antibodies specific for an intracellular domain (ICD) binding region of the full-length receptor (e.g., full-length HER2) to form a plurality of captured truncated receptors, wherein the capture antibodies are restrained on a solid support (e.g., to transform the truncated receptors present in a full-length receptor-depleted cellular extract into complexes of truncated receptors and capture antibodies);

(iv) incubating (e.g., contacting) the plurality of captured truncated receptors with detection antibodies comprising activation state-independent antibodies and activation state-dependent antibodies specific for an ICD binding region of the full-length receptor (e.g., full-length HER2) to form a plurality of detectable captured truncated receptors (e.g., to transform the complexes of captured truncated receptors into complexes of detectable captured truncated receptors comprising the captured truncated receptors and detection antibodies), wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(v) incubating (e.g., contacting) the plurality of detectable captured truncated receptors with a second member of the signal amplification pair to generate an amplified signal; and (vi) detecting the amplified signal generated from the first and second members of the signal amplification pair.

The activation state-independent antibodies may be directly labeled with the facilitating moiety or indirectly labeled with the facilitating moiety, e.g., via hybridization between an oligonucleotide conjugated to the activation state-independent antibodies and a complementary oligonucleotide conjugated to the facilitating moiety. Similarly, the activation state-dependent antibodies may be directly labeled with the first member of the signal amplification pair or indirectly labeled with the first member of the signal amplification pair, e.g., via binding between a first member of a binding pair conjugated to the activation state-dependent antibodies and a second member of the binding pair conjugated to the first member of the signal amplification pair. In certain instances, the first member of the binding pair is biotin and the second member of the binding pair is an avidin such as streptavidin or neutravidin.

In some embodiments, the facilitating moiety may be, for example, glucose oxidase. In certain instances, the glucose oxidase and the activation state-independent antibodies can be conjugated to a sulfhydryl-activated dextran molecule as described in, e.g., Examples 16-17 of PCT Publication No. WO2009/108637, the disclosure of which is herein incorporated by reference in its entirety for all purposes. The sulfhydryl-activated dextran molecule typically has a molecular weight of about 500 kDa (e.g., about 250, 300, 350, 400, 450, 500, 550, 600, 650, 700, or 750 kDa). In other embodiments, the oxidizing agent may be, for example, hydrogen peroxide ($H_2O_2$). In yet other embodiments, the first member of the signal amplification pair may be, for example, a peroxidase such as horseradish peroxidase (HRP). In further embodiments, the second member of the signal amplification pair may be, for example, a tyramide reagent (e.g., biotin-tyramide). Preferably, the amplified signal is generated by peroxidase oxidization of biotin-tyramide to produce an activated tyramide (e.g., to transform the biotin-tyramide into an activated tyramide). The activated tyramide may be directly detected or indirectly detected, e.g., upon the addition of a signal-detecting reagent. Non-limiting examples of signal-detecting reagents include streptavidin-labeled fluorophores and combinations of streptavidin-labeled peroxidases and chromogenic reagents such as, e.g., 3,3',5,5'-tetramethylbenzidine (TMB).

In certain instances, the horseradish peroxidase and the activation state-dependent antibodies can be conjugated to a sulfhydryl-activated dextran molecule. The sulfhydryl-activated dextran molecule typically has a molecular weight of about 70 kDa (e.g., about 40, 45, 50, 55, 60, 65, 70, 75, 80, 85, 90, 95, or 100 kDa).

The truncated receptor is typically a fragment of the full-length receptor and shares an intracellular domain (ICD) binding region with the full-length receptor. In certain embodiments, the full-length receptor comprises an extracellular domain (ECD) binding region, a transmembrane domain, and an intracellular domain (ICD) binding region. Without being bound to any particular theory, the truncated receptor may arise through the proteolytic processing of the ECD of the full-length receptor or by alternative initiation of translation from methionine residues that are located before, within, or after the transmembrane domain, e.g., to create a truncated receptor with a shortened ECD or a truncated receptor comprising a membrane-associated or cytosolic ICD fragment.

In certain preferred embodiments, the truncated receptor is p95HER2 and the corresponding full-length receptor is HER2. However, one skilled in the art will appreciate that the methods described herein for detecting truncated proteins can be applied to a number of different proteins including, but not limited to, the EGFR VIII mutant (implicated in glioblastoma, colorectal cancer, etc.), other truncated receptor tyrosine kinases, caspases, and the like. Example 12 of PCT Publication No. WO2009/108637, the disclosure of which is herein incorporated by reference in its entirety for all purposes, provides an exemplary embodiment of the assay methods of the present invention for detecting truncated receptors such as p95HER2 in cells using a multiplex, high-throughput, proximity dual detection microarray ELISA having superior dynamic range.

In some embodiments, the plurality of beads specific for an ECD binding region comprises a streptavidin-biotin pair, wherein the streptavidin is attached to the bead and the biotin is attached to an antibody. In certain instances, the antibody is specific for the ECD binding region of the full-length receptor (e.g., full-length HER2).

In some embodiments, each dilution series of capture antibodies comprises a series of descending capture antibody concentrations. In certain instances, the capture antibodies are serially diluted at least 2-fold (e.g., 2, 5, 10, 20, 50, 100, 500, or 1000-fold) to produce a dilution series comprising a set number (e.g., 2, 3, 4, 5, 6, 7, 8, 9, 10, 15, 20, 25, or more) of descending capture antibody concentrations which are spotted onto an array. Preferably, at least 2, 3, 4, 5, or 6 replicates of each capture antibody dilution are spotted onto the array.

In other embodiments, the solid support comprises glass (e.g., a glass slide), plastic, chips, pins, filters, beads, paper, membrane (e.g., nylon, nitrocellulose, polyvinylidene fluoride (PVDF), etc.), fiber bundles, or any other suitable substrate. In a preferred embodiment, the capture antibodies are restrained (e.g., via covalent or noncovalent interactions) on glass slides coated with a nitrocellulose polymer such as, for example, FAST® Slides, which are commercially available from Whatman Inc. (Florham Park, N.J.).

In another aspect, the present invention provides a method for identifying the response of a gastric cancer to treatment with an anticancer drug, the method comprising:

(a) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in a cellular extract produced from an isolated cancer cell; and (b) identifying the response of the gastric cancer to treatment with an anticancer drug based upon the expression level and/or activation level of the one or more analytes determined in step (a).

In some embodiments, the expression level and/or activation level of the one or more analytes is expressed as a relative fluorescence unit (RFU) value that corresponds to the signal intensity for a particular analyte of interest that is determined using, e.g., a proximity assay such as the Collaborative Proximity Immunoassay (COPIA) described herein. In other embodiments, the expression level and/or activation level of the one or more analytes is expressed as "−", "±", "+", "++", "+++", or "++++" that corresponds to increasing signal intensity for a particular analyte of interest that is determined using, e.g., a proximity assay such as COPIA. In some instances, an undetectable or minimally detectable level of expression or activation of a particular analyte of interest that is determined using, e.g., a proximity assay such as COPIA, may be expressed as "−" or "±". In other instances, a low level of expression or activation of a particular analyte of interest that is determined using, e.g., a proximity assay such as COPIA, may be expressed as "+". In yet other instances, a moderate level of expression or activation of a particular analyte of interest that is determined using, e.g., a proximity assay such as COPIA, may be expressed as "++". In still yet other instances, a high level of expression or activation of a particular analyte of interest that is determined using, e.g., a proximity assay such as COPIA, may be expressed as "+++". In further instances, a very high level of expression or activation of a particular analyte of interest that is determined using, e.g., a proximity assay such as COPIA, may be expressed as "++++".

In yet other embodiments, the expression level and/or activation level of the one or more analytes is quantitated by calibrating or normalizing the RFU value that is determined using, e.g., a proximity assay such as COPIA, against a standard curve generated for the particular analyte of interest. In certain instances, a computed units (CU) value can be calculated based upon the standard curve. In other instances, the CU value can be expressed as "−", "±", "+", "++", "+++", or "++++" in accordance with the description above for signal intensity. Example 13 provides a non-limiting example of data analysis for the quantitation of signal transduction pathway proteins (e.g., one or more HER2 and/or c-MET signaling pathway components) in gastric cancer cells.

In certain embodiments, the expression or activation level of a particular analyte of interest, when expressed as "−", "±", "+", "++", "+++", or "++++", may correspond to a level of expression or activation that is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher or lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher or lower) than a reference expression level or activation level, e.g., when compared to a negative control such as an IgG control, when compared to a standard curve generated for the analyte of interest, when compared to a positive control such as a pan-CK control, when compared to an expression or activation level determined in the presence of an anticancer drug, and/or when compared to an expression or activation level determined in the absence of an anticancer drug. In some instances, the correlation is analyte-specific. As a non-limiting example, a "+" level of expression or activation determined using, e.g., a proximity assay such as COPIA, may correspond to a 2-fold increase in expression or activation for one analyte and a 5-fold increase for another analyte when compared to a reference expression or activation level.

In some embodiments, the cancer cell is isolated from a subject having the gastric cancer after administration of an anticancer drug to the subject. In other embodiments, the isolated cancer cell is contacted with an anticancer drug. In either of these embodiments, the response of the gastric cancer to treatment with the anticancer drug may be identified by comparing the expression level and/or activation level of the one or more analytes to a reference expression and/or activation profile of the one or more analytes generated in the absence of the anticancer drug.

In certain embodiments, step (b) comprises applying the expression level and/or activation level of the one or more analytes determined in step (a) to identify the response of the gastric cancer to treatment with an anticancer drug.

In one particular embodiment, the present invention provides a method for identifying the response of a gastric cancer to treatment with an anticancer drug, the method comprising:

(a) isolating a cancer cell after administration of an anticancer drug, or prior to incubation with an anticancer drug;

(b) lysing the isolated cell to produce a cellular extract;

(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract; and (d) comparing the expression level and/or activation level of the one or more analytes determined in step (c) to a reference expression and/or activation profile of the one or more analytes that is generated in the absence of the anticancer drug to identify whether the gastric cancer is responsive or non-responsive to treatment with the anticancer drug.

In another particular embodiment, the present invention provides a method for identifying the response of a gastric cancer to treatment with an anticancer drug, the method comprising:

(a) isolating a cancer cell after administration of an anticancer drug, or prior to incubation with an anticancer drug;

(b) lysing the isolated cell to produce a cellular extract;

(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract;

(d) comparing the expression level and/or activation level of the one or more analytes determined in step (c) to a reference expression and/or activation profile of the one or more analytes that is generated in the absence of the anticancer drug; and (e) indicating that the gastric cancer is responsive to treatment with the anticancer drug (e.g., the gastric tumor has an increased likelihood or probability of response to treatment with the anticancer drug) when the expression level and/or activation level determined for the one or more analytes is changed (e.g., substantially decreased) compared to the reference expression and/or activation profile.

In certain instances, the gastric cancer is an adenocarcinoma. In certain other instances, the gastric cancer has metastazied to the esophagus, the small intestine, lymph nodes, organs, bones, or combinations thereof.

In some embodiments, the expression (e.g., total) level and/or activation (e.g., phosphorylation) level of the one or more analytes is considered to be "changed" in the presence of an anticancer drug when it is at least about 5%, 10%, 15%, 20%, 25%, 30%, 35%, 40%, 45%, 50%, 55%, 60%, 65%, 70%, 75%, 80%, 85%, 90%, or 95% more or less activated than in the absence of the anticancer drug. In other embodiments, the expression (e.g., total) level and/or activation (e.g., phosphorylation) level of the one or more analytes is considered to be "substantially decreased" in the presence of an anticancer drug when it is at least about 50%, 55%, 60%, 65%, 70%, 75%, 80%, 85%, 90%, or 95% less activated than in the absence of the anticancer drug. In further embodiments, the expression (e.g., total) level and/or activation (e.g., phosphorylation) level of the one or more analytes is considered to be "substantially decreased" in the presence of an anticancer drug (1) when there is a change from high or strong expression and/or activation of the analyte without the anticancer drug to medium, weak, low, or very weak expression and/or activation of the analyte with the anticancer drug, or (2) when there is a change from medium expression and/or activation of the analyte without the anticancer drug to weak, low, or very weak expression and/or activation of the analyte with the anticancer drug.

To preserve the in situ activation states, signal transduction proteins are typically extracted shortly after the cells are isolated, preferably within 96, 72, 48, 24, 6, or 1 hr, more preferably within 30, 15, or 5 minutes. The isolated cells may also be incubated with growth factors usually at nanomolar to micromolar concentrations for about 1-30 minutes to resuscitate or stimulate signal transducer activation (see, e.g., Irish et al., Cell, 118:217-228 (2004)). Stimulatory growth factors include epidermal growth factor (EGF), heregulin (HRG), TGF-α, P1GF, angiopoietin (Ang), NRG1, PGF, TNF-α, VEGF, PDGF, IGF, FGF, HGF, cytokines, and the like. To evaluate potential anticancer therapies for an individual patient, the isolated cells can be incubated with one or more anticancer drugs of varying doses prior to, during, and/or after growth factor stimulation. Growth factor stimulation can be performed for a few minutes or hours (e.g., about 1-5 minutes to about 1-6 hours). After isolation, treatment with the anticancer drug, and/or growth factor stimulation, the cells are lysed to extract the signal transduction proteins using any technique known in the art.

Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the lysate can be stored at −80° C. until use.

In some embodiments, the anticancer drug comprises an agent that interferes with the function of activated signal transduction pathway components in cancer cells. Non-limiting examples of such agents include those listed above in Table 1.

In other embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells such as those anticancer agents described above. In further embodiments, the isolated cells are treated with one or more anti-signaling agents, anti-proliferative agents, and/or hormonal therapeutic agents in combination with at least one chemotherapeutic agent such as those anticancer agents described above.

In certain embodiments, the reference expression or activation level of the one or more analytes (e.g., one or more HER2 and/or c-Met signaling pathway components) determined in step (c) is obtained from a normal cell such as a non-cancerous cell from a healthy individual not having a cancer such as gastric cancer. In certain other embodiments, the reference expression or activation level of the one or more analytes (e.g., one or more HER2 and/or c-Met signaling pathway components) determined in step (c) is obtained from a tumor cell such as a gastric cancer cell from a sample from a patient with a cancer such as gastric cancer.

In some embodiments, the reference expression or activation level of the one or more analytes (e.g., one or more HER2 and/or c-Met signaling pathway components) determined in step (c) is obtained from a cell (e.g., a tumor cell such as a gastric cancer cell obtained from a patient sample) that is not treated with the anticancer drug. In particular embodiments, the cell that is not treated with the anticancer drug is obtained from the same sample that the isolated cell (e.g., a test cell to be interrogated) used to produce the cellular extract is obtained. In certain instances, the presence of a lower level of expression or activation of the one or more analytes (e.g., one or more HER2 and/or c-Met signaling pathway components) compared to the reference expression or activation level indicates that the gastric cancer is responsive to treatment with the anticancer drug (e.g., the gastric tumor has an increased likelihood or probability of response to treatment with the anticancer drug). In certain other instances, the presence of an identical, similar, or higher level of expression or activation of the one or more analytes (e.g., one or more HER2 and/or c-Met signaling pathway components) compared to the reference expression or activation level indicates that the gastric cancer is not responsive to treatment with the anticancer drug (e.g., the gastric tumor has a decreased likelihood or probability of response to treatment with the anticancer drug).

In alternative embodiments, the reference expression or activation level of the one or more analytes (e.g., one or more HER2 and/or c-Met signaling pathway components) determined in step (c) is obtained from a cell sensitive to the anticancer drug that is treated with the anticancer drug. In such embodiments, the presence of an identical, similar, or lower level of expression or activation of the one or more analytes (e.g., one or more HER2 and/or c-Met signaling pathway components) compared to the reference expression or activation level indicates that the gastric cancer is responsive to treatment with the anticancer drug (e.g., the gastric tumor has an increased likelihood or probability of response to treatment with the anticancer drug). In certain other alternative embodiments, the reference expression or activation level of the one or more analytes (e.g., one or more HER2 and/or c-Met signaling pathway components) determined in step (c) is obtained from a cell resistant to the anticancer drug that is treated with the anticancer drug. In such embodiments, the presence of an identical, similar, or higher level of expression or activation of the one or more analytes (e.g., one or more HER2 and/or c-Met signaling pathway components) compared to the reference expression or activation level indicates that the gastric cancer is not responsive to treatment with the anticancer drug (e.g., the gastric tumor has a decreased likelihood or probability of response to treatment with the anticancer drug).

In certain embodiments, a higher level of expression or activation of the one or more analytes (e.g., one or more HER2 and/or c-Met signaling pathway components) determined in step (c) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher) than the reference expression or activation level of the corresponding analyte in a cell (e.g., a gastric cancer cell obtained from a patient sample) not treated with the anticancer drug, in an anticancer drug-sensitive cell treated with the anticancer drug, or in an anticancer drug-resistant cell treated with the anticancer drug.

In other embodiments, a lower level of expression or activation of the one or more analytes (e.g., one or more HER2 and/or c-Met signaling pathway components) determined in step (c) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold lower) than the reference expression or activation level of the corresponding analyte in a cell (e.g., a gastric cancer cell obtained from a patient sample) not treated with the anticancer drug, in an anticancer drug-sensitive cell treated with the anticancer drug, or in an anticancer drug-resistant cell treated with the anticancer drug.

Non-limiting examples of analytes such as signal transduction molecules that can be interrogated for expression (e.g., total amount) levels and/or activation (e.g., phosphorylation) levels in a cellular extract include those analytes shown in Table 2 above such as, e.g., receptor tyrosine kinases, non-receptor tyrosine kinases, tyrosine kinase signaling cascade components, nuclear hormone receptors, nuclear receptor coactivators, nuclear receptor repressors, and combinations thereof.

In one embodiment, the methods of the present invention comprise determining the expression (e.g., total amount) level and/or activation (e.g., phosphorylation) level of 1 or any combination of 2, 3, 4, 5, 6, 7, 8, 9, 10, 11, 12, or all 13 of the following analytes in a cellular extract in accordance with the combinations described above: (1) HER1/EGFR/ErbB1; (2) HER2/ErbB2; (3) p95HER2; (4) HER3/ErbB3; (5) c-Met; (6) IGF1R; (7) cKit; (8) PI3K (e.g., PIK3CA and/or PIK3R1); (9) Shc; (10) Akt; (11) p70S6K; (12) VEGFR (e.g., VEGFR1, VEGFR2, and/or VEGFR3); and (13) PDGFR (e.g., PDGFRA and/or PDGFRB).

In one particular embodiment, the present invention comprises determining the expression (e.g., total) level and/or activation (e.g., phosphorylation) level of HER1, HER2, p95HER2, and HER3. In another particular embodiment, the present invention comprises determining the expression (e.g., total) level and/or activation (e.g., phosphorylation) level of HER1, HER2, HER3, c-Met, IGF1R, cKit, PI3K (e.g., PIK3CA and/or PIK3R1), and Shc. In yet another particular embodiment, the present invention comprises determining the expression (e.g., total) level and/or activation (e.g., phosphorylation) level of HER1, HER2, p95HER2, HER3, c-Met, IGF1R, cKit, PI3K (e.g., PIK3CA and/or PIK3R1), Shc, Akt, p70S6K, VEGFR (e.g., VEGFR1, 2, and/or 3), and PDGFR (e.g., PDGFRA and/or B).

In certain embodiments, the present invention further comprises determining the expression (e.g., total) level and/or activation (e.g., phosphorylation) level of one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) additional analytes in the cellular extract. In some embodiments, the one or more additional analytes comprises one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) signal transduction molecules selected from the group consisting of receptor tyrosine kinases, non-receptor tyrosine kinases, tyrosine kinase signaling cascade components, nuclear hormone receptors, nuclear receptor coactivators, nuclear receptor repressors, and combinations thereof.

In particular embodiments, the present invention further comprises determining the expression (e.g., total) level and/or activation (e.g., phosphorylation) level of one or any combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more of the following additional analytes in a cellular extract: HER4, MEK, PTEN, SGK3, 4E-BP1, ERK2 (MAPK1), ERK1 (MAPK3), PDK1, PDK2, GSK-3β, Raf, SRC, NFkB-IkB, mTOR, EPH-A, EPH-B, EPH-C, EPH-D, FLT-3, TIE-1, TIE-2, c-FMS, Abl, FTL 3, RET, FGFR1, FGFR2, FGFR3, FGFR4, ER, PR, NCOR, AIB1, RON, PIP2, PIP3, p27, protein tyrosine phosphatases (e.g., PTP1B, PTPN13, BDP1, etc.), receptor dimers, other HER2 signaling pathway components, other c-Met signaling pathway components, and combinations thereof.

In some embodiments, the cell (e.g., the test cell from which a cellular extract is produced) is a tumor cell such as a gastric cancer cell. In certain instances, the tumor cell is a circulating tumor cell or a fine needle aspirate (FNA) cell obtained from a tumor. In other embodiments, the cell (e.g., the test cell from which a cellular extract is produced) is isolated from a sample that is obtained, e.g., from a gastric cancer patient. Non-limiting examples of samples include bodily fluid samples such as, for example, a whole blood, serum, plasma, ductal lavage fluid, nipple aspirate, lymph, bone marrow aspirate, urine, saliva, and/or fine needle aspirate (FNA) sample. In particular embodiments, the sample comprises a whole blood, serum, plasma, and/or tumor tissue sample such as gastric tumor tissue.

In certain instances, the methods of the present invention may further comprise a step of providing the result of the comparison obtained in step (d) to a user (e.g., a clinician such as an oncologist or a general practitioner) in a readable format. In some instances, the method may further comprise sending or reporting the result of the comparison obtained in step (d) to a clinician, e.g., an oncologist or a general practitioner. In other instances, the method may further comprise recording or storing the result of the comparison obtained in step (d) in a computer database or other suitable machine or device for storing information, e.g., at a laboratory.

In some embodiments, determining the expression level of the one or more analytes (e.g., one or more HER2 and/or c-Met signaling pathway components) in step (c) comprises detecting the total amount of the one or more analytes in the cellular extract with one or more antibodies specific for the corresponding analyte. In particular embodiments, the antibodies bind to the analyte irrespective of the activation state of the analyte to be detected, i.e., the antibodies detect both the non-activated and activated forms of the analyte.

In other embodiments, determining the activation levels of the one or more analytes (e.g., one or more HER2 and/or c-Met signaling pathway components) in step (c) comprises detecting a phosphorylation level of the one or more analytes in the cellular extract with antibodies specific for the phosphorylated form of each of the analytes to be detected.

Expression (e.g., total) level or status and/or activation (e.g., phosphorylation) level or status can be determined using any of a variety of techniques. In particular embodiments, the expression (e.g., total) and/or activation (e.g., phosphorylation) level or status of one or more of the analytes (e.g., one or more HER2 and/or c-Met signaling pathway components) in step (c) is detected with an immunoassay such as a single detection assay or a proximity dual detection assay (e.g., a COllaborative Proximity Immuno-Assay (COPIA)) as described herein.

In yet another aspect, the present invention provides a method for predicting the response of a subject having a gastric cancer to treatment with an anticancer drug, the method comprising:
  (a) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in a cellular extract produced from an isolated cancer cell; and
  (b) predicting the response of the subject having the gastric cancer to treatment with an anticancer drug based upon the expression level and/or activation level of the one or more analytes determined in step (a).

In some embodiments, the expression level and/or activation level of the one or more analytes is expressed as a relative fluorescence unit (RFU) value that corresponds to the signal intensity for a particular analyte of interest that is determined using, e.g., a proximity assay such as the Collaborative Proximity Immunoassay (COPIA) described herein. In other embodiments, the expression level and/or activation level of the one or more analytes is expressed as "−", "+", "+", "++", "+++", or "++++" that corresponds to increasing signal intensity for a particular analyte of interest that is determined using, e.g., a proximity assay such as COPIA. In some instances, an undetectable or minimally detectable level of expression or activation of a particular analyte of interest that is determined using, e.g., a proximity assay such as COPIA, may be expressed as "−" or "±". In other instances, a low level of expression or activation of a particular analyte of interest that is determined using, e.g., a proximity assay such as COPIA, may be expressed as "+". In yet other instances, a moderate level of expression or activation of a particular analyte of interest that is determined using, e.g., a proximity assay such as COPIA, may be expressed as "++". In still yet other instances, a high level of expression or activation of a particular analyte of interest that is determined using, e.g., a proximity assay such as COPIA, may be expressed as "+++". In further instances, a very high level of expression or activation of a particular analyte of interest that is determined using, e.g., a proximity assay such as COPIA, may be expressed as "++++".

In yet other embodiments, the expression level and/or activation level of the one or more analytes is quantitated by calibrating or normalizing the RFU value that is determined using, e.g., a proximity assay such as COPIA, against a standard curve generated for the particular analyte of interest. In certain instances, a computed units (CU) value can be calculated based upon the standard curve. In other instances, the CU value can be expressed as "−", "±", "+", "++", "+++", or "++++" in accordance with the description above for signal intensity. Example 13 provides a non-limiting example of data analysis for the quantitation of signal transduction pathway proteins (e.g., one or more HER2 and/or c-MET signaling pathway components) in gastric cancer cells.

In certain embodiments, the expression or activation level of a particular analyte of interest, when expressed as "−", "±", "+", "++", "+++", or "++++", may correspond to a level of expression or activation that is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher or lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher or lower) than a reference expression level or activation level, e.g., when compared to a negative control such as an IgG control, when compared to a standard curve generated for the analyte of interest, when compared to a positive control such as a pan-CK control, when compared to an expression or activation level determined in the presence of an anticancer drug, and/or when compared to an expression or activation level determined in the absence of an anticancer drug. In some instances, the correlation is analyte-specific. As a non-limiting example, a "+" level of expression or activation determined using, e.g., a proximity assay such as COPIA, may correspond to a 2-fold increase in expression or activation for one analyte and a 5-fold increase for another analyte when compared to a reference expression or activation level.

In some embodiments, the cancer cell is isolated from a subject having the gastric cancer after administration of an anticancer drug to the subject. In other embodiments, the isolated cancer cell is contacted with an anticancer drug. In either of these embodiments, the response of the subject having the gastric cancer to treatment with the anticancer drug may be predicted by comparing the expression level and/or activation level of the one or more analytes to a reference expression and/or activation profile of the one or more analytes generated in the absence of the anticancer drug.

In certain embodiments, step (b) comprises applying the expression level and/or activation level of the one or more analytes determined in step (a) to predict the response of the subject having the gastric cancer to treatment with an anticancer drug.

In one particular embodiment, the present invention provides a method for predicting the response of a subject having a gastric cancer to treatment with an anticancer drug, the method comprising:

(a) isolating a cancer cell after administration of an anticancer drug, or prior to incubation with an anticancer drug;
(b) lysing the isolated cell to produce a cellular extract;
(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract; and
(d) comparing the expression level and/or activation level of the one or more analytes determined in step (c) to a reference expression and/or activation profile of the one or more analytes that is generated in the absence of the anticancer drug to predict the likelihood that the subject having the gastric cancer will respond to treatment with the anticancer drug.

In another particular embodiment, the present invention provides a method for predicting the response of a subject having a gastric cancer to treatment with an anticancer drug, the method comprising:
(a) isolating a cancer cell after administration of an anticancer drug, or prior to incubation with an anticancer drug;
(b) lysing the isolated cell to produce a cellular extract;
(c) determining the expression level and/or activation level of one or more analytes selected from the group consisting of HER1, HER2, p95HER2, HER3, c-Met, IGF1R, cKit, PI3K, Shc, Akt, p70S6K, VEGFR, PDGFR, and combinations thereof in the cellular extract;
(d) comparing the expression level and/or activation level of the one or more analytes determined in step (c) to a reference expression and/or activation profile of the one or more analytes that is generated in the absence of the anticancer drug to predict the likelihood that the subject will respond to treatment with the anticancer drug; and
(e) indicating that the subject having the gastric cancer will likely respond to treatment with the anticancer drug (e.g., the subject having the gastric cancer has an increased likelihood or probability of response to treatment with the anticancer drug) when the expression level and/or activation level determined for the one or more analytes is changed (e.g., substantially decreased) compared to the reference expression and/or activation profile.

In certain instances, the gastric cancer is an adenocarcinoma. In certain other instances, the gastric cancer has metastazied to the esophagus, the small intestine, lymph nodes, organs, bones, or combinations thereof.

In some embodiments, the expression (e.g., total) level and/or activation (e.g., phosphorylation) level of the one or more analytes is considered to be "changed" in the presence of an anticancer drug when it is at least about 5%, 10%, 15%, 20%, 25%, 30%, 35%, 40%, 45%, 50%, 55%, 60%, 65%, 70%, 75%, 80%, 85%, 90%, or 95% more or less activated than in the absence of the anticancer drug. In other embodiments, the expression (e.g., total) level and/or activation (e.g., phosphorylation) level of the one or more analytes is considered to be "substantially decreased" in the presence of an anticancer drug when it is at least about 50%, 55%, 60%, 65%, 70%, 75%, 80%, 85%, 90%, or 95% less activated than in the absence of the anticancer drug. In further embodiments, the expression (e.g., total) level and/or activation (e.g., phosphorylation) level of the one or more analytes is considered to be "substantially decreased" in the presence of an anticancer drug (1) when there is a change from high or strong expression and/or activation of the analyte without the anticancer drug to medium, weak, low, or very weak expression and/or activation of the analyte with the anticancer drug, or (2) when there is a change from medium expression and/or activation of the analyte without the anticancer drug to weak, low, or very weak expression and/or activation of the analyte with the anticancer drug.

To preserve the in situ activation states, signal transduction proteins are typically extracted shortly after the cells are isolated, preferably within 96, 72, 48, 24, 6, or 1 hr, more preferably within 30, 15, or 5 minutes. The isolated cells may also be incubated with growth factors usually at nanomolar to micromolar concentrations for about 1-30 minutes to resuscitate or stimulate signal transducer activation (see, e.g., Irish et al., Cell, 118:217-228 (2004)). Stimulatory growth factors include epidermal growth factor (EGF), heregulin (HRG), TGF-α, PlGF, angiopoietin (Ang), NRG1, PGF, TNF-α, VEGF, PDGF, IGF, FGF, HGF, cytokines, and the like. To evaluate potential anticancer therapies for an individual patient, the isolated cells can be incubated with one or more anticancer drugs of varying doses prior to, during, and/or after growth factor stimulation. Growth factor stimulation can be performed for a few minutes or hours (e.g., about 1-5 minutes to about 1-6 hours). After isolation, treatment with the anticancer drug, and/or growth factor stimulation, the cells are lysed to extract the signal transduction proteins using any technique known in the art. Preferably, the cell lysis is initiated between about 1-360 minutes after growth factor stimulation, and more preferably at two different time intervals: (1) at about 1-5 minutes after growth factor stimulation; and (2) between about 30-180 minutes after growth factor stimulation. Alternatively, the lysate can be stored at −80° C. until use.

In some embodiments, the anticancer drug comprises an agent that interferes with the function of activated signal transduction pathway components in cancer cells. Non-limiting examples of such agents include those listed above in Table 1.

In other embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells such as those anticancer agents described above. In further embodiments, the isolated cells are treated with one or more anti-signaling agents, anti-proliferative agents, and/or hormonal therapeutic agents in combination with at least one chemotherapeutic agent such as those anticancer agents described above.

In certain embodiments, the reference expression or activation level of the one or more analytes (e.g., one or more HER2 and/or c-Met signaling pathway components) determined in step (c) is obtained from a normal cell such as a non-cancerous cell from a healthy individual not having a cancer such as gastric cancer. In certain other embodiments, the reference expression or activation level of the one or more analytes (e.g., one or more HER2 and/or c-Met signaling pathway components) determined in step (c) is obtained from a tumor cell such as a gastric cancer cell from a sample from a patient with a cancer such as gastric cancer.

In some embodiments, the reference expression or activation level of the one or more analytes (e.g., one or more HER2 and/or c-Met signaling pathway components) determined in step (c) is obtained from a cell (e.g., a tumor cell such as a gastric cancer cell obtained from a patient sample)

that is not treated with the anticancer drug. In particular embodiments, the cell that is not treated with the anticancer drug is obtained from the same sample that the isolated cell (e.g., a test cell to be interrogated) used to produce the cellular extract is obtained. In certain instances, the presence of a lower level of expression or activation of the one or more analytes (e.g., one or more HER2 and/or c-Met signaling pathway components) compared to the reference expression or activation level indicates that the subject having the gastric cancer will likely respond to treatment with the anticancer drug (e.g., the subject having the gastric cancer has an increased likelihood or probability of response to treatment with the anticancer drug). In certain other instances, the presence of an identical, similar, or higher level of expression or activation of the one or more analytes (e.g., one or more HER2 and/or c-Met signaling pathway components) compared to the reference expression or activation level indicates that the subject having the gastric cancer will not likely respond to treatment with the anticancer drug (e.g., the subject having the gastric cancer has a decreased likelihood or probability of response to treatment with the anticancer drug).

In alternative embodiments, the reference expression or activation level of the one or more analytes (e.g., one or more HER2 and/or c-Met signaling pathway components) determined in step (c) is obtained from a cell sensitive to the anticancer drug that is treated with the anticancer drug. In such embodiments, the presence of an identical, similar, or lower level of expression or activation of the one or more analytes (e.g., one or more HER2 and/or c-Met signaling pathway components) compared to the reference expression or activation level indicates that the subject having the gastric cancer will likely respond to treatment with the anticancer drug (e.g., the subject having the gastric cancer has an increased likelihood or probability of response to treatment with the anticancer drug). In certain other alternative embodiments, the reference expression or activation level of the one or more analytes (e.g., one or more HER2 and/or c-Met signaling pathway components) determined in step (c) is obtained from a cell resistant to the anticancer drug that is treated with the anticancer drug. In such embodiments, the presence of an identical, similar, or higher level of expression or activation of the one or more analytes (e.g., one or more HER2 and/or c-Met signaling pathway components) compared to the reference expression or activation level indicates that the subject having the gastric cancer will not likely respond to treatment with the anticancer drug (e.g., the subject having the gastric cancer has a decreased likelihood or probability of response to treatment with the anticancer drug).

In certain embodiments, a higher level of expression or activation of the one or more analytes (e.g., one or more HER2 and/or c-Met signaling pathway components) determined in step (c) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher) than the reference expression or activation level of the corresponding analyte in a cell (e.g., a gastric cancer cell obtained from a patient sample) not treated with the anticancer drug, in an anticancer drug-sensitive cell treated with the anticancer drug, or in an anticancer drug-resistant cell treated with the anticancer drug.

In other embodiments, a lower level of expression or activation of the one or more analytes (e.g., one or more HER2 and/or c-Met signaling pathway components) determined in step (c) is considered to be present in a cellular extract when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold lower) than the reference expression or activation level of the corresponding analyte in a cell (e.g., a gastric cancer cell obtained from a patient sample) not treated with the anticancer drug, in an anticancer drug-sensitive cell treated with the anticancer drug, or in an anticancer drug-resistant cell treated with the anticancer drug.

Non-limiting examples of analytes such as signal transduction molecules that can be interrogated for expression (e.g., total amount) levels and/or activation (e.g., phosphorylation) levels in a cellular extract include those analytes shown in Table 2 above such as, e.g., receptor tyrosine kinases, non-receptor tyrosine kinases, tyrosine kinase signaling cascade components, nuclear hormone receptors, nuclear receptor coactivators, nuclear receptor repressors, and combinations thereof.

In one embodiment, the methods of the present invention comprise determining the expression (e.g., total amount) level and/or activation (e.g., phosphorylation) level of 1 or any combination of 2, 3, 4, 5, 6, 7, 8, 9, 10, 11, 12, or all 13 of the following analytes in a cellular extract in accordance with the combinations described above: (1) HER1/EGFR/ErbB1; (2) HER2/ErbB2; (3) p95HER2; (4) HER3/ErbB3; (5) c-Met; (6) IGF1R; (7) cKit; (8) PI3K (e.g., PIK3CA and/or PIK3R1); (9) Shc; (10) Akt; (11) p70S6K; (12) VEGFR (e.g., VEGFR1, VEGFR2, and/or VEGFR3); and (13) PDGFR (e.g., PDGFRA and/or PDGFRB).

In one particular embodiment, the present invention comprises determining the expression (e.g., total) level and/or activation (e.g., phosphorylation) level of HER1, HER2, p95HER2, and HER3. In another particular embodiment, the present invention comprises determining the expression (e.g., total) level and/or activation (e.g., phosphorylation) level of HER1, HER2, HER3, c-Met, IGF1R, cKit, PI3K (e.g., PIK3CA and/or PIK3R1), and Shc. In yet another particular embodiment, the present invention comprises determining the expression (e.g., total) level and/or activation (e.g., phosphorylation) level of HER1, HER2, p95HER2, HER3, c-Met, IGF1R, cKit, PI3K (e.g., PIK3CA and/or PIK3R1), Shc, Akt, p70S6K, VEGFR (e.g., VEGFR1, 2, and/or 3), and PDGFR (e.g., PDGFRA and/or B).

In certain embodiments, the present invention further comprises determining the expression (e.g., total) level and/or activation (e.g., phosphorylation) level of one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) additional analytes in the cellular extract. In some embodiments, the one or more additional analytes comprises one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) signal transduction molecules selected from the group consisting of receptor tyrosine kinases, non-receptor tyrosine kinases, tyrosine kinase signaling cascade components, nuclear hormone receptors, nuclear receptor coactivators, nuclear receptor repressors, and combinations thereof.

In particular embodiments, the present invention further comprises determining the expression (e.g., total) level and/or activation (e.g., phosphorylation) level of one or any combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more of the following additional analytes in a cellular extract: HER4, MEK, PTEN, SGK3, 4E-BP1, ERK2 (MAPK1), ERK1 (MAPK3), PDK1, PDK2, GSK-3β, Raf, SRC, NFkB-IkB, mTOR, EPH-A, EPH-B, EPH-C, EPH-D, FLT-3, TIE-1, TIE-2, c-FMS, Abl, FTL 3, RET, FGFR1, FGFR2, FGFR3, FGFR4, ER, PR, NCOR, AIB1, RON, PIP2, PIP3, p27, protein tyrosine phosphatases (e.g., PTP1B, PTPN13, BDP1, etc.), receptor dimers, other HER2 signaling pathway components, other c-Met signaling pathway components, and combinations thereof.

In some embodiments, the cell (e.g., the test cell from which a cellular extract is produced) is a tumor cell such as a gastric cancer cell. In certain instances, the tumor cell is a circulating tumor cell or a fine needle aspirate (FNA) cell obtained from a tumor. In other embodiments, the cell (e.g., the test cell from which a cellular extract is produced) is isolated from a sample that is obtained, e.g., from a gastric cancer patient. Non-limiting examples of samples include bodily fluid samples such as, for example, a whole blood, serum, plasma, ductal lavage fluid, nipple aspirate, lymph, bone marrow aspirate, urine, saliva, and/or fine needle aspirate (FNA) sample. In particular embodiments, the sample comprises a whole blood, serum, plasma, and/or tumor tissue sample such as gastric tumor tissue.

In certain instances, the methods of the present invention may further comprise a step of providing the result of the comparison obtained in step (d) to a user (e.g., a clinician such as an oncologist or a general practitioner) in a readable format. In some instances, the method may further comprise sending or reporting the result of the comparison obtained in step (d) to a clinician, e.g., an oncologist or a general practitioner. In other instances, the method may further comprise recording or storing the result of the comparison obtained in step (d) in a computer database or other suitable machine or device for storing information, e.g., at a laboratory.

In some embodiments, determining the expression level of the one or more analytes (e.g., one or more HER2 and/or c-MET signaling pathway components) in step (c) comprises detecting the total amount of the one or more analytes in the cellular extract with one or more antibodies specific for the corresponding analyte. In particular embodiments, the antibodies bind to the analyte irrespective of the activation state of the analyte to be detected, i.e., the antibodies detect both the non-activated and activated forms of the analyte.

In other embodiments, determining the activation levels of the one or more analytes (e.g., one or more HER2 and/or c-MET signaling pathway components) in step (c) comprises detecting a phosphorylation level of the one or more analytes in the cellular extract with antibodies specific for the phosphorylated form of each of the analytes to be detected.

Expression (e.g., total) level or status and/or activation (e.g., phosphorylation) level or status can be determined using any of a variety of techniques. In particular embodiments, the expression (e.g., total) and/or activation (e.g., phosphorylation) level or status of one or more of the analytes (e.g., one or more HER2 and/or c-MET signaling pathway components) in step (c) is detected with an immunoassay such as a single detection assay or a proximity dual detection assay (e.g., a COllaborative Proximity Immuno-Assay (COPIA)) as described herein.

IV. c-Met Mediated Cancers c-Met can be overexpressed in many malignancies. In c-Met mediated cancers, amplification and/or activation mutations within the tyrosine kinase domain, juxtamembrane domain, or semaphorin domain have been identified. Selecting a suitable anticancer drug for the treatment of a c-Met mediated cancer is possible by assessing the level of expression and/or activation state of c-Met in the presence of therapeutics. Activation of c-Met leads to increased cell growth, invasion, angiogenesis, and metastasis. In certain embodiments, the present invention provides methods of selecting appropriate therapeutic strategies to inhibit c-Met activation and/or overexpression.

In one embodiment, the present invention provides a method for selecting a suitable anticancer drug for the treatment of a c-Met mediated cancer, the method comprising:
(a) determining the expression level and/or activation level of c-Met and optionally one or more additional analytes in a cellular extract produced from an isolated cancer cell; and
(b) selecting a suitable anticancer drug for the treatment of the c-Met mediated cancer based upon the expression level and/or activation level of the one or more analytes determined in step (a).

In some instances, the present invention provides a method for selecting a suitable anticancer drug for the treatment of a c-Met mediated cancer, the method comprising:
(a) isolating a cancer cell after administration of an anticancer drug, or prior to incubation with an anticancer drug;
(b) lysing the isolated cell to produce a cellular extract;
(c) determining the expression level and/or activation level of c-Met and optionally one or more additional analytes in the cellular extract; and
(d) comparing the expression level and/or activation level of c-Met and optionally one or more additional analytes determined in step (c) to a reference expression and/or activation profile of c-Met and optionally one or more additional analytes that is generated in the absence of the anticancer drug to determine whether the anticancer drug is suitable or unsuitable for the treatment of the c-Met mediated cancer.

In another embodiment, the present invention provides a method for identifying the response of a c-Met mediated cancer to treatment with an anticancer drug, the method comprising:
(a) determining the expression level and/or activation level of c-Met and optionally one or more additional analytes in a cellular extract produced from an isolated cancer cell; and
(b) identifying the response of the c-Met mediated cancer to treatment with an anticancer drug based upon the expression level and/or activation level of the one or more analytes determined in step (a).

In some instances, the present invention provides a method for identifying the response of a c-Met mediated cancer to treatment with an anticancer drug, the method comprising:
(a) isolating a cancer cell after administration of an anticancer drug, or prior to incubation with an anticancer drug;
(b) lysing the isolated cell to produce a cellular extract;
(c) determining the expression level and/or activation level of c-Met and optionally one or more additional analytes in the cellular extract; and (d) comparing the expression level and/or activation level of c-Met and optionally one or more additional analytes determined in step (c) to a reference expression and/or activation profile of c-Met and optionally one or more additional analytes that is generated in the absence of the anticancer drug to identify whether the gastric cancer is responsive or non-responsive to treatment with the anticancer drug.

In yet another embodiment, the present invention provides a method for predicting the response of a subject having a c-Met mediated cancer to treatment with an anticancer drug, the method comprising:
(a) determining the expression level and/or activation level of c-Met and optionally one or more additional analytes in a cellular extract produced from an isolated cancer cell; and
(b) predicting the response of the subject having the c-Met mediated cancer to treatment with an anticancer drug based upon the expression level and/or activation level of the one or more analytes determined in step (a).

In some instances, the present invention provides a method for predicting the response of a subject having a c-Met mediated cancer to treatment with an anticancer drug, the method comprising:
(a) isolating a cancer cell after administration of an anticancer drug, or prior to incubation with an anticancer drug;
(b) lysing the isolated cell to produce a cellular extract;
(c) determining the expression level and/or activation level of c-Met and optionally one or more additional analytes in the cellular extract; and
(d) comparing the expression level and/or activation level of c-Met and optionally one or more additional analytes determined in step (c) to a reference expression and/or activation profile of c-Met and optionally one or more additional analytes that is generated in the absence of the anticancer drug to predict the likelihood that the subject having the gastric cancer will respond to treatment with the anticancer drug.

In certain aspects, the present invention provides methods to evaluate c-Met mediated cancer pathways in patient samples such as circulating tumor cells (CTC) or fine needle aspirates (FNA). The methods herein provide an optimum therapeutic strategy for the patient. In one aspect, at least one, two, three, four, five, six, seven, eight, nine, or more of the following additional analytes can be screened or interrogated to determine the response to a c-Met mediated cancer therapy (e.g., a c-Met inhibitor): HER1, HER2, p95HER2, HER3, IGF1R, cKit, PI3K (e.g., PIK3CA, PIK3R1), Shc, Akt (e.g., Akt1, Akt2, Akt3), p70S6K, VEGFR (e.g., VEGFR1, VEGFR2, VEGFR3), PDGFR (e.g., PDGFRA, PDGFRB), RON, and combinations thereof. For example, a responder to XL-880 has activated c-MET and VEGFR2, while a non-responder may have a combination of RTKs activated.

In certain other instances, the methods provided herein find utility in selecting a combination therapy for the treatment of gastric cancer. For example, gastric cancer patients with activated c-MET, VEGFR2, and EGFR can be successfully treated with a combination of Iressa® and XL880, while gastric cancer patients with activated c-MET, VEGFR2, HER1, HER2, p95HER2, and HER3 can be treated with Tykerb®+XL880.

In tumor cells, it is believed that c-Met activation causes the triggering of a diverse series of signaling cascades resulting in cell growth, proliferation, invasion, and protection from apoptosis. Data from cellular and animal tumor models suggest that the underlying biological mechanisms for tumorgenicity of c-Met mediated cancers are typically achieved in three different ways: (1) with the establishment of HGF/c-Met autocrine loops; (2) via c-Met or HGF overexpression; and (3) in the presence of kinase-activating mutations in the c-Met receptor coding sequence. Overexpression of HGF and c-Met is indicative of the increased aggressiveness of tumors and poor prognostic signs in cancer patients. HGF/c-Met signaling induces tumor angiogenesis by inducing proliferation and migration in endothelial cells, by inducing expression of vascular endothelial growth factor (VEGF), a key proangiogenic factor, as well as by dramatically downregulating thrombospondin 1 (TSP-1), a negative regulator of angiogenesis. HGF and c-Met expression have been observed in tumor biopsies of most solid tumors, and c-Met signaling has been documented in a wide range of human malignancies, including stomach (gastric), bladder, breast, cervical, colorectal, gastric, head and neck, liver, lung, ovarian, pancreatic, prostrate, renal, and thyroid cancers, as well as in various sarcomas, hematopoietic malignancies, and melanoma. Most notably, activating mutations in the tyrosine kinase domain of c-Met have been positively identified in patients with a hereditary form of papillary renal cancer, directly implicating c-Met in human tumorigenesis.

In certain embodiments, the present invention provides methods for detecting the expression and activation states of c-Met and optionally a plurality of deregulated signal transducers, in tumor cells derived from tumor tissue or circulating cells of a solid tumor in a specific, multiplex, high-throughput assay. The present invention also provides methods and compositions for the selection of appropriate therapies to down-regulate or shut down one or more deregulated signaling pathways. Thus, embodiments of the invention may be used to facilitate the design of personalized therapies based on the particular molecular signature provided by the collection of activated signal transduction proteins in a given patient's tumor such as a gastric tumor.

In some embodiments, the anticancer drug (e.g., one or more anticancer drugs suitable for the treatment of a c-Met mediated cancer such as gastric cancer) comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the isolated cells are treated with one or more anti-signaling agents, anti-proliferative agents, and/or hormonal therapeutic agents in combination with at least one chemotherapeutic agent.

In certain embodiments, the antibody such as a HGF- or c-Met-specific antibody prevents ligand/receptor binding, resulting in growth inhibition and tumor regression by inhibiting proliferation and enhancing apoptosis. In some instances, a combination of monoclonal antibodies can also be used. The strategy of using monoclonal antibodies allows for exclusive specificity against HGF/c-Met, a relatively long half-life compared to small molecule kinase inhibitors, and the potential to elicit a host immune response against tumor cells. AMG102 is a fully human IgG2 monoclonal antibody that selectively binds and neutralizes HGF, thereby preventing its binding to c-Met and subsequent activation. AMG102 has been shown to enhance the effects of various standard chemotherapeutic agents such as temozolomide and docetaxel in vitro and in xenografts when combined. MetMAb is a humanized, monovalent, antagonistic anti-c-

Met antibody derived from the agonistic monoclonal antibody 5D5. MetMAb binds to c-Met with high affinity and remains on the cell surface with c-Met, preventing HGF binding and subsequent c-Met phosphorylation as well as downstream signaling activity and cellular responses. Recent preclinical studies show that MetMAb is a potent anti-c-Met inhibitor that has promise as a therapeutic antibody in human cancer, especially in combination with EGFR and/or VEGF inhibitors.

Small molecule inhibitors of c-Met include, but are not limited to, ARQ197 (ArQule), which is a non-ATP-competitive agent highly selective for the c-Met receptor. Other selective c-Met inhibitors have recently entered initial clinical evaluations and include: JNJ-38877605 (Johnson & Johnson), which is a small-molecule, ATP-competitive inhibitor of the catalytic activity of c-Met; PF-04217903 (Pfizer), which is an orally available, ATP-competitive small-molecule inhibitor of c-Met with selectivity of >1000-fold for c-Met compared with a screening panel of >150 protein kinases; SGX523 (SGX Pharmaceuticals), which is another highly selective, ATP-competitive inhibitor of c-Met with >1,000-fold selectivity for c-Met over all other kinases in a screening panel of 213 protein kinases and potent antitumor activity when dosed orally in human xenograft models with no overt toxicity.

GSK 1363089/XL880 (Exelixis) is another example of a small molecule inhibitor of c-Met which targets c-Met at an IC50 of 0.4 nM. Binding affinity is high to both c-Met and VEGFR2, causing a conformational change in the kinase to move XL880 deeper into the ATP-binding pocket. The time on target is >24 hours for both receptors. XL880 has good oral bioavailability, and it is a CYP450 substrate, but not an inhibitor or inducer. Two Phase I clinical trials examined different administration schedules of XL880, either on a 5 day on/9 day off schedule (Study 1) or as a fixed daily dose (Study 2). XL880 acts on two cooperating pathways for proliferation and survival at different points in time, already providing a therapeutic solution for tumor response to the initial assault on tumor angiogenesis. Phase II trials have started in multiple tumor types, including papillary renal cancer, gastric cancer, and head and neck cancers.

XL184 (Exelixis) is a novel, orally administered, small molecule anticancer compound that, in preclinical models, has demonstrated potent inhibition of both c-MET and VEGFR2. MP470 (SuperGen) is a novel, orally bioavailable small molecule with inhibitory activity against c-Met as well as several other protein tyrosine kinase targets, including mutant forms of c-Kit, mutant PDGFRa, and mutant Flt-3. MGCD265 (Methylgene) potently inhibits c-Met, Ron, VEGFRs, and Tie-2 enzymatic activities in vitro and has been reported to abrogate HGF dependent cellular endpoints, such as cell scatter and wound healing, as well as VEGF-dependent responses such as in vitro angiogenesis and in vivo vascular permeability. MK-2461 (Merck) is a potent inhibitor of c-Met, KDR, FGFR1/2/3, and Flt 1/3/4 that is especially active in preclinical models with MET gene amplification, in which c-Met is constitutively phosphorylated. MK-2461 has been well tolerated in early Phase I evaluation.

In certain instances, binding of HGF ligand to the c-Met receptor can be inhibited by subregions of HGF or c-Met that can act as decoys or antagonists. These decoys and antagonists stoichiometrically compete with the ligand or receptor without leading to c-Met activation, thereby preventing activation of downstream pathways and biological outcomes. Several HGF and c-Met variants have been validated experimentally as antagonists both in vitro and in vivo and work by blocking ligand binding or preventing c-Met dimerization. In addition, molecular analogs to HGF that have been shown to compete with HGF for c-Met binding have been developed.

V. Construction of Antibody Arrays

In certain aspects, the expression level and/or activation state of one or more (e.g., a plurality) of analytes (e.g., signal transduction molecules) in a cellular extract of tumor cells such as gastric cancer cells is detected using an antibody-based array comprising a dilution series of capture antibodies restrained on a solid support. The arrays typically comprise a plurality of different capture antibodies at a range of capture antibody concentrations that are coupled to the surface of the solid support in different addressable locations.

In one particular embodiment, the present invention provides an addressable array having superior dynamic range comprising a plurality of dilution series of capture antibodies restrained on a solid support, in which the capture antibodies in each dilution series are specific for one or more analytes corresponding to a component of a signal transduction pathway and other target proteins. In various aspects, this embodiment includes arrays that comprise components of signal transduction pathways characteristic of particular tumors, e.g., signal transduction pathways active in gastric cancer cells (e.g., HER2 and/or c-Met pathways). Thus, the present invention may be advantageously practiced wherein each signal transduction molecule or other protein of interest with a potential expression or activation defect causing gastric cancer is represented on a single array or chip. In some aspects, the components of a given signal transduction pathway active in a particular tumor cell are arrayed in a linear sequence that corresponds to the sequence in which information is relayed through a signal transduction pathway within a cell. Examples of such arrays are described herein and also shown in FIGS. 5-9 of PCT Publication No. WO2009/108637, the disclosure of which is herein incorporated by reference in its entirety for all purposes. The capture antibodies specific for one or more components of a given signal transduction pathway active in a particular tumor cell can also be printed in a randomized fashion to minimize any surface-related artifacts.

The solid support can comprise any suitable substrate for immobilizing proteins. Examples of solid supports include, but are not limited to, glass (e.g., a glass slide), plastic, chips, pins, filters, beads, paper, membranes, fiber bundles, gels, metal, ceramics, and the like. Membranes such nylon (Biotrans™, ICN Biomedicals, Inc. (Costa Mesa, Calif.); Zeta-Probe®, Bio-Rad Laboratories (Hercules, Calif.)), nitrocellulose (Protran®, Whatman Inc. (Florham Park, N.J.)), and PVDF (Immobilon™, Millipore Corp. (Billerica, Mass.)) are suitable for use as solid supports in the arrays of the present invention. Preferably, the capture antibodies are restrained on glass slides coated with a nitrocellulose polymer, e.g., FAST® Slides, which are commercially available from Whatman Inc. (Florham Park, N.J.).

Particular aspects of the solid support which are desirable include the ability to bind large amounts of capture antibodies and the ability to bind capture antibodies with minimal denaturation. Another suitable aspect is that the solid support displays minimal "wicking" when antibody solutions containing capture antibodies are applied to the support. A solid support with minimal wicking allows small aliquots of capture antibody solution applied to the support to result in small, defined spots of immobilized capture antibody.

The capture antibodies are typically directly or indirectly (e.g., via capture tags) restrained on the solid support via covalent or noncovalent interactions (e.g., ionic bonds, hydrophobic interactions, hydrogen bonds, Van der Waals forces, dipole-dipole bonds). In some embodiments, the capture antibodies are covalently attached to the solid support using a homobifunctional or heterobifunctional crosslinker using standard crosslinking methods and conditions. Suitable crosslinkers are commercially available from vendors such as, e.g., Pierce Biotechnology (Rockford, Ill.).

Methods for generating arrays suitable for use in the present invention include, but are not limited to, any technique used to construct protein or nucleic acid arrays. In some embodiments, the capture antibodies are spotted onto an array using a microspotter, which are typically robotic printers equipped with split pins, blunt pins, or ink jet printing. Suitable robotic systems for printing the antibody arrays described herein include the PixSys 5000 robot (Cartesian Technologies; Irvine, Calif.) with ChipMaker2 split pins (TeleChem International; Sunnyvale, Calif.) as well as other robotic printers available from BioRobics (Woburn, Mass.) and Packard Instrument Co. (Meriden, Conn.). Preferably, at least 2, 3, 4, 5, or 6 replicates of each capture antibody dilution are spotted onto the array.

Another method for generating arrays suitable for use in the present invention comprises dispensing a known volume of a capture antibody dilution at each selected array position by contacting a capillary dispenser onto a solid support under conditions effective to draw a defined volume of liquid onto the support, wherein this process is repeated using selected capture antibody dilutions at each selected array position to create a complete array. The method may be practiced in forming a plurality of such arrays, where the solution-depositing step is applied to a selected position on each of a plurality of solid supports at each repeat cycle. A further description of such a method can be found, e.g., in U.S. Pat. No. 5,807,522.

In certain instances, devices for printing on paper can be used to generate the antibody arrays. For example, the desired capture antibody dilution can be loaded into the printhead of a desktop jet printer and printed onto a suitable solid support (see, e.g., Silzel et al., *Clin. Chem.*, 44:2036-2043 (1998)).

In some embodiments, the array generated on the solid support has a density of at least about 5 spots/cm$^2$, and preferably at least about 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000, or 10,000 spots/cm$^2$.

In certain instances, the spots on the solid support each represents a different capture antibody. In certain other instances, multiple spots on the solid support represent the same capture antibody, e.g., as a dilution series comprising a series of descending capture antibody concentrations.

Additional examples of methods for preparing and constructing antibody arrays on solid supports are described in U.S. Pat. Nos. 6,197,599, 6,777,239, 6,780,582, 6,897,073, 7,179,638, and 7,192,720; U.S. Patent Publication Nos. 20060115810, 20060263837, 20060292680, and 20070054326; and Varnum et al., *Methods Mol. Biol.*, 264: 161-172 (2004).

Methods for scanning antibody arrays are known in the art and include, without limitation, any technique used to scan protein or nucleic acid arrays. Microarray scanners suitable for use in the present invention are available from PerkinElmer (Boston, Mass.), Agilent Technologies (Palo Alto, Calif.), Applied Precision (Issaquah, Wash.), GSI Lumonics Inc. (Billerica, Mass.), and Axon Instruments (Union City, Calif.). As a non-limiting example, a GSI ScanArray3000 for fluorescence detection can be used with ImaGene software for quantitation.

VI. Single Detection Assays

In some embodiments, the assay for detecting the expression and/or activation level of one or more analytes (e.g., one or more signal transduction molecules such as one or more components of the HER2 and/or c-Met signaling pathways) of interest in a cellular extract of cells such as tumor cells is a multiplex, high-throughput two-antibody assay having superior dynamic range. As a non-limiting example, the two antibodies used in the assay can comprise: (1) a capture antibody specific for a particular analyte of interest; and (2) a detection antibody specific for an activated form of the analyte (i.e., activation state-dependent antibody). The activation state-dependent antibody is capable of detecting, for example, the phosphorylation, ubiquitination, and/or complexation state of the analyte. Alternatively, the detection antibody comprises an activation state-independent antibody, which detects the total amount of the analyte in the cellular extract. The activation state-independent antibody is generally capable of detecting both the activated and non-activated forms of the analyte.

In one particular embodiment, the two-antibody assay for detecting the expression or activation level of an analyte of interest comprises:

(i) incubating the cellular extract with one or a plurality of dilution series of capture antibodies to form a plurality of captured analytes;

(ii) incubating the plurality of captured analytes with detection antibodies specific for the corresponding analytes to form a plurality of detectable captured analytes, wherein the detection antibodies comprise activation state-dependent antibodies for detecting the activation (e.g., phosphorylation) level of the analyte or activation state-independent antibodies for detecting the expression level (e.g., total amount) of the analyte;

(iii) incubating the plurality of detectable captured analytes with first and second members of a signal amplification pair to generate an amplified signal; and (iv) detecting the amplified signal generated from the first and second members of the signal amplification pair.

The two-antibody assays described herein are typically antibody-based arrays which comprise a plurality of different capture antibodies at a range of capture antibody concentrations that are coupled to the surface of a solid support in different addressable locations. Examples of suitable solid supports for use in the present invention are described above.

The capture antibodies and detection antibodies are preferably selected to minimize competition between them with respect to analyte binding (i.e., both capture and detection antibodies can simultaneously bind their corresponding signal transduction molecules).

In one embodiment, the detection antibodies comprise a first member of a binding pair (e.g., biotin) and the first member of the signal amplification pair comprises a second member of the binding pair (e.g., streptavidin). The binding pair members can be coupled directly or indirectly to the detection antibodies or to the first member of the signal amplification pair using methods well-known in the art. In certain instances, the first member of the signal amplification pair is a peroxidase (e.g., horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, etc.), and the second member of the signal amplification pair is a tyramide reagent (e.g., biotin-tyramide). In these instances, the amplified signal is generated by peroxidase oxidization of the tyramide reagent to produce an activated tyramide in the presence of hydrogen peroxide ($H_2O_2$).

The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

An exemplary protocol for performing the two-antibody assays described herein is provided in Example 3 of PCT Publication No. WO2009/108637, the disclosure of which is herein incorporated by reference in its entirety for all purposes.

In another embodiment of a two-antibody approach, the present invention provides a method for detecting the expression or activation level of a truncated receptor, the method comprising:

(i) incubating the cellular extract with a plurality of beads specific for an extracellular domain (ECD) binding region of a full-length receptor;

(ii) removing the plurality of beads from the cellular extract, thereby removing the full-length receptor to foam a cellular extract devoid of the full-length receptor;

(iii) incubating the cellular extract devoid of the full-length receptor with a dilution series of one or a plurality of capture antibodies specific for an intracellular domain (ICD) binding region of the full-length receptor to form a plurality of captured truncated receptors;

(iv) incubating the plurality of captured truncated receptors with detection antibodies specific for an ICD binding region of the full-length receptor to form a plurality of detectable captured truncated receptors, wherein the detection antibodies comprise activation state-dependent antibodies for detecting the activation (e.g., phosphorylation) level of the truncated receptor or activation state-independent antibodies for detecting the expression level (e.g., total amount) of the truncated receptor;

(v) incubating the plurality of detectable captured truncated receptors with first and second members of a signal amplification pair to generate an amplified signal; and (vi) detecting an amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

FIG. 14A of PCT Publication No. WO2009/108637, the disclosure of which is herein incorporated by reference in its entirety for all purposes, shows that beads coated with an antibody directed to the extracellular domain (ECD) of a receptor of interest binds the full-length receptor (e.g., HER2), but not the truncated receptor (e.g., p95HER2) to remove any full-length receptor from the assay. FIG. 14B of PCT Publication No. WO2009/108637 shows that the truncated receptor (e.g., p95HER2), once bound to a capture antibody, may then be detected by a detection antibody that is specific for the intracellular domain (ICD) of the full-length receptor (e.g., HER2). The detection antibody may be directly conjugated to horseradish peroxidase (HRP). Tyramide signal amplification (TSA) may then be performed to generate a signal to be detected. The expression level or activation state of the truncated receptor (e.g., p95HER2) can be interrogated to determine, e.g., its total concentration or its phosphorylation state, ubiquitination state, and/or complexation state.

In another embodiment, the present invention provides kits for performing the two-antibody assays described above comprising: (a) a dilution series of one or a plurality of capture antibodies restrained on a solid support; and (b) one or a plurality of detection antibodies (e.g., activation state-independent antibodies and/or activation state-dependent antibodies). In some instances, the kits can further contain instructions for methods of using the kit to detect the expression levels and/or activation states of one or a plurality of signal transduction molecules of cells such as tumor cells. The kits may also contain any of the additional reagents described above with respect to performing the specific methods of the present invention such as, for example, first and second members of the signal amplification pair, tyramide signal amplification reagents, wash buffers, etc.

VII. Proximity Dual Detection Assays

In some embodiments, the assay for detecting the expression and/or activation level of one or more analytes (e.g., one or more signal transduction molecules such as one or more components of the HER2 and/or c-Met signaling pathways) of interest in a cellular extract of cells such as tumor cells is a multiplex, high-throughput proximity (i.e., three-antibody) assay having superior dynamic range. As a non-limiting example, the three antibodies used in the proximity assay can comprise: (1) a capture antibody specific for a particular analyte of interest; (2) a detection antibody specific for an activated form of the analyte (i.e., activation state-dependent antibody); and (3) a detection antibody which detects the total amount of the analyte (i.e., activation state-independent antibody). The activation state-dependent antibody is capable of detecting, e.g., the phosphorylation, ubiquitination, and/or complexation state of the analyte, while the activation state-independent antibody is capable of detecting the total amount (i.e., both the activated and non-activated forms) of the analyte.

In one particular embodiment, the proximity assay for detecting the activation level or status of an analyte of interest comprises:

(i) incubating the cellular extract with one or a plurality of dilution series of capture antibodies to form a plurality of captured analytes;

(ii) incubating the plurality of captured analytes with detection antibodies comprising one or a plurality of activation state-independent antibodies and one or a plurality of activation state-dependent antibodies specific for the corresponding analytes to form a plurality of detectable captured analytes, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(iii) incubating the plurality of detectable captured analytes with a second member of the signal amplification pair to generate an amplified signal; and (iv) detecting the amplified signal generated from the first and second members of the signal amplification pair.

In another particular embodiment, the proximity assay for detecting the activation level or status of an analyte of interest that is a truncated receptor comprises:

(i) incubating the cellular extract with a plurality of beads specific for an extracellular domain (ECD) binding region of a full-length receptor;

(ii) removing the plurality of beads from the cellular extract, thereby removing the full-length receptor to form a cellular extract devoid of the full-length receptor;

(iii) incubating the cellular extract devoid of the full-length receptor with one or a plurality of capture antibodies specific for an intracellular domain (ICD) binding region of the full-length receptor to form a plurality of captured truncated receptors;

(iv) incubating the plurality of captured truncated receptors with detection antibodies comprising one or a plurality of activation state-independent antibodies and one or a plurality of activation state-dependent antibodies specific for an ICD binding region of the full-length receptor to form a plurality of detectable captured truncated receptors, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;

(v) incubating the plurality of detectable captured truncated receptors with a second member of the signal amplification pair to generate an amplified signal; and (vi) detecting the amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the activation state-dependent antibodies can be labeled with a facilitating moiety and the activation state-independent antibodies can be labeled with a first member of a signal amplification pair.

As another non-limiting example, the three antibodies used in the proximity assay can comprise: (1) a capture antibody specific for a particular analyte of interest; (2) a first detection antibody which detects the total amount of the analyte (i.e., a first activation state-independent antibody); and (3) a second detection antibody which detects the total amount of the analyte (i.e., a second activation state-independent antibody). In preferred embodiments, the first and second activation state-independent antibodies recognize different (e.g., distinct) epitopes on the analyte.

In one particular embodiment, the proximity assay for detecting the expression level of an analyte of interest comprises:

(i) incubating the cellular extract with one or a plurality of dilution series of capture antibodies to form a plurality of captured analytes;

(ii) incubating the plurality of captured analytes with detection antibodies comprising one or a plurality of first and second activation state-independent antibodies specific for the corresponding analytes to form a plurality of detectable captured analytes, wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(iii) incubating the plurality of detectable captured analytes with a second member of the signal amplification pair to generate an amplified signal; and (iv) detecting the amplified signal generated from the first and second members of the signal amplification pair.

In another particular embodiment, the proximity assay for detecting the expression level of an analyte of interest that is a truncated receptor comprises:

(i) incubating the cellular extract with a plurality of beads specific for an extracellular domain (ECD) binding region of a full-length receptor;

(ii) removing the plurality of beads from the cellular extract, thereby removing the full-length receptor to form a cellular extract devoid of the full-length receptor;

(iii) incubating the cellular extract devoid of the full-length receptor with one or a plurality of capture antibodies specific for an intracellular domain (ICD) binding region of the full-length receptor to form a plurality of captured truncated receptors;

(iv) incubating the plurality of captured truncated receptors with detection antibodies comprising one or a plurality of first and second activation state-independent antibodies specific for an ICD binding region of the full-length receptor to form a plurality of detectable captured truncated receptors, wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(v) incubating the plurality of detectable captured truncated receptors with a second member of the signal amplification pair to generate an amplified signal; and (vi) detecting the amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the first activation state-independent antibodies can be labeled with a first member of a signal amplification pair and the second activation state-independent antibodies can be labeled with a facilitating moiety.

The proximity assays described herein are typically antibody-based arrays which comprise one or a plurality of different capture antibodies at a range of capture antibody concentrations that are coupled to the surface of a solid support in different addressable locations. Examples of suitable solid supports for use in the present invention are described above.

The capture antibodies, activation state-independent antibodies, and activation state-dependent antibodies are preferably selected to minimize competition between them with respect to analyte binding (i.e., all antibodies can simultaneously bind their corresponding signal transduction molecules).

In some embodiments, activation state-independent antibodies for detecting activation levels of one or more of the analytes or, alternatively, first activation state-independent antibodies for detecting expression levels of one or more of the analytes further comprise a detectable moiety. In such instances, the amount of the detectable moiety is correlative to the amount of one or more of the analytes in the cellular extract. Examples of detectable moieties include, but are not limited to, fluorescent labels, chemically reactive labels, enzyme labels, radioactive labels, and the like. Preferably, the detectable moiety is a fluorophore such as an Alexa Fluor® dye (e.g., Alexa Fluor® 647), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The detectable moiety can be coupled directly or indirectly to the activation state-independent antibodies using methods well-known in the art.

In certain instances, activation state-independent antibodies for detecting activation levels of one or more of the analytes or, alternatively, first activation state-independent antibodies for detecting expression levels of one or more of the analytes are directly labeled with the facilitating moiety. The facilitating moiety can be coupled to activation state-independent antibodies using methods well-known in the art. A suitable facilitating moiety for use in the present invention includes any molecule capable of generating an oxidizing agent which channels to (i.e., is directed to) and reacts with (i.e., binds, is bound by, or foams a complex with) another molecule in proximity (i.e., spatially near or close) to the facilitating moiety. Examples of facilitating moieties include, without limitation, enzymes such as glucose oxidase or any other enzyme that catalyzes an oxidation/reduction reaction involving molecular oxygen ($O_2$) as the electron acceptor, and photosensitizers such as methylene blue, rose bengal, porphyrins, squarate dyes, phthalocyanines, and the like. Non-limiting examples of oxidizing agents include hydrogen peroxide ($H_2O_2$), a singlet oxygen, and any other compound that transfers oxygen atoms or gains electrons in an oxidation/reduction reaction. Preferably, in the presence of a suitable substrate (e.g., glucose, light, etc.), the facilitating moiety (e.g., glucose oxidase, photosensitizer, etc.) generates an oxidizing agent (e.g., hydrogen peroxide ($H_2O_2$), single oxygen, etc.) which channels to and reacts with the first member of the signal amplification pair (e.g., horseradish peroxidase (HRP), hapten protected by a protecting group, an enzyme inactivated by thioether linkage to an enzyme inhibitor, etc.) when the two moieties are in proximity to each other.

In certain other instances, activation state-independent antibodies for detecting activation levels of one or more of the analytes or, alternatively, first activation state-independent antibodies for detecting expression levels of one or more of the analytes are indirectly labeled with the facilitating moiety via hybridization between an oligonucleotide linker conjugated to the activation state-independent antibodies and a complementary oligonucleotide linker conjugated to the facilitating moiety. The oligonucleotide linkers can be coupled to the facilitating moiety or to the activation state-independent antibodies using methods well-known in the art. In some embodiments, the oligonucleotide linker conjugated to the facilitating moiety has 100% complementarity to the oligonucleotide linker conjugated to the activation state-independent antibodies. In other embodiments, the oligonucleotide linker pair comprises at least one, two, three, four, five, six, or more mismatch regions, e.g., upon hybridization under stringent hybridization conditions. One skilled in the art will appreciate that activation state-independent antibodies specific for different analytes can either be conjugated to the same oligonucleotide linker or to different oligonucleotide linkers.

The length of the oligonucleotide linkers that are conjugated to the facilitating moiety or to the activation state-independent antibodies can vary. In general, the linker sequence can be at least about 5, 10, 15, 20, 25, 30, 35, 40, 45, 50, 75, or 100 nucleotides in length. Typically, random nucleic acid sequences are generated for coupling. As a non-limiting example, a library of oligonucleotide linkers can be designed to have three distinct contiguous domains: a spacer domain; signature domain; and conjugation domain. Preferably, the oligonucleotide linkers are designed for efficient coupling without destroying the function of the facilitating moiety or activation state-independent antibodies to which they are conjugated.

The oligonucleotide linker sequences can be designed to prevent or minimize any secondary structure formation under a variety of assay conditions. Melting temperatures are typically carefully monitored for each segment within the linker to allow their participation in the overall assay procedures. Generally, the range of melting temperatures of the segment of the linker sequence is between 1-10° C. Computer algorithms (e.g., OLIGO 6.0) for determining the melting temperature, secondary structure, and hairpin structure under defined ionic concentrations can be used to analyze each of the three different domains within each linker. The overall combined sequences can also be analyzed for their structural characterization and their comparability to other conjugated oligonucleotide linker sequences, e.g., whether they will hybridize under stringent hybridization conditions to a complementary oligonucleotide linker.

The spacer region of the oligonucleotide linker provides adequate separation of the conjugation domain from the oligonucleotide crosslinking site. The conjugation domain functions to link molecules labeled with a complementary oligonucleotide linker sequence to the conjugation domain via nucleic acid hybridization. The nucleic acid-mediated hybridization can be performed either before or after antibody-analyte (i.e., antigen) complex formation, providing a more flexible assay format. Unlike many direct antibody conjugation methods, linking relatively small oligonucleotides to antibodies or other molecules has minimal impact on the specific affinity of antibodies towards their target analyte or on the function of the conjugated molecules.

In some embodiments, the signature sequence domain of the oligonucleotide linker can be used in complex multiplexed protein assays. Multiple antibodies can be conjugated with oligonucleotide linkers with different signature sequences. In multiplex immunoassays, reporter oligonucleotide sequences labeled with appropriate probes can be used to detect cross-reactivity between antibodies and their antigens in the multiplex assay format.

Oligonucleotide linkers can be conjugated to antibodies or other molecules using several different methods. For example, oligonucleotide linkers can be synthesized with a thiol group on either the 5' or 3' end. The thiol group can be deprotected using reducing agents (e.g., TCEP-HCl) and the resulting linkers can be purified by using a desalting spin column. The resulting deprotected oligonucleotide linkers can be conjugated to the primary amines of antibodies or other types of proteins using heterobifunctional cross linkers such as SMCC. Alternatively, 5'-phosphate groups on oligonucleotides can be treated with water-soluble carbodiimide EDC to form phosphate esters and subsequently coupled to amine-containing molecules. In certain instances, the diol on the 3'-ribose residue can be oxidized to aldehyde groups and then conjugated to the amine groups of antibodies or other types of proteins using reductive amination. In certain other instances, the oligonucleotide linker can be synthesized with a biotin modification on either the 3' or 5' end and conjugated to streptavidin-labeled molecules.

Oligonucleotide linkers can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). In general, the synthesis of oligonucleotides makes use of common nucleic acid protecting and coupling groups, such as dimethoxytrityl at the 5'-end and phosphoramidites at the 3'-end. Suitable reagents for oligonucleotide synthesis, methods for nucleic acid deprotection, and methods for nucleic acid purification are known to those of skill in the art.

In certain instances, activation state-dependent antibodies for detecting activation levels of one or more of the analytes or, alternatively, second activation state-independent antibodies for detecting expression levels of one or more of the analytes are directly labeled with the first member of the signal amplification pair. The signal amplification pair member can be coupled to activation state-dependent antibodies to detect activation levels or second activation state-independent antibodies to detect expression levels using methods well-known in the art. In certain other instances, activation state-dependent antibodies or second activation state-independent antibodies are indirectly labeled with the first member of the signal amplification pair via binding between a first member of a binding pair conjugated to the activation state-dependent antibodies or second activation state-independent antibodies and a second member of the binding pair conjugated to the first member of the signal amplification pair. The binding pair members (e.g., biotin/streptavidin) can be coupled to the signal amplification pair member or to the activation state-dependent antibodies or second activation state-independent antibodies using methods well-known in the art. Examples of signal amplification pair members include, but are not limited to, peroxidases such horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, and the like. Other examples of signal amplification pair members include haptens protected by a protecting group and enzymes inactivated by thioether linkage to an enzyme inhibitor.

In one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. Methods of using GO and HRP in a proximity assay are described in, e.g., Langry et al., U.S. Dept. of Energy Report No. UCRL-ID-136797 (1999). When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

In another example of proximity channeling, the facilitating moiety is a photosensitizer and the first member of the signal amplification pair is a large molecule labeled with multiple haptens that are protected with protecting groups that prevent binding of the haptens to a specific binding partner (e.g., ligand, antibody, etc.). For example, the signal amplification pair member can be a dextran molecule labeled with protected biotin, coumarin, and/or fluorescein molecules. Suitable protecting groups include, but are not limited to, phenoxy-, analino-, olefin-, thioether-, and selenoether-protecting groups. Additional photo sensitizers and protected hapten molecules suitable for use in the proximity assays of the present invention are described in U.S. Pat. No. 5,807,675. When the photosensitizer is excited with light, it generates an oxidizing agent (i.e., singlet oxygen). If the hapten molecules are within channeling proximity to the photosensitizer, the singlet oxygen generated by the photosensitizer is channeled to and reacts with thioethers on the protecting groups of the haptens to yield carbonyl groups (ketones or aldehydes) and suiphinic acid, releasing the protecting groups from the haptens. The unprotected haptens are then available to specifically bind to the second member of the signal amplification pair (e.g., a specific binding partner that can generate a detectable signal). For example, when the hapten is biotin, the specific binding partner can be an enzyme-labeled streptavidin. Exemplary enzymes include alkaline phosphatase, β-galactosidase, HRP, etc.

After washing to remove unbound reagents, the detectable signal can be generated by adding a detectable (e.g., fluorescent, chemiluminescent, chromogenic, etc.) substrate of the enzyme and detected using suitable methods and instrumentation known in the art. Alternatively, the detectable signal can be amplified using tyramide signal amplification and the activated tyramide either directly detected or detected upon the addition of a signal-detecting reagent as described above.

In yet another example of proximity channeling, the facilitating moiety is a photosensitizer and the first member of the signal amplification pair is an enzyme-inhibitor complex. The enzyme and inhibitor (e.g., phosphonic acid-labeled dextran) are linked together by a cleavable linker (e.g., thioether). When the photosensitizer is excited with light, it generates an oxidizing agent (i.e., singlet oxygen). If the enzyme-inhibitor complex is within channeling proximity to the photosensitizer, the singlet oxygen generated by the photosensitizer is channeled to and reacts with the cleavable linker, releasing the inhibitor from the enzyme, thereby activating the enzyme. An enzyme substrate is added to generate a detectable signal, or alternatively, an amplification reagent is added to generate an amplified signal.

In a further example of proximity channeling, the facilitating moiety is HRP, the first member of the signal amplification pair is a protected hapten or an enzyme-inhibitor complex as described above, and the protecting groups comprise p-alkoxy phenol. The addition of phenylenediamine and $H_2O_2$ generates a reactive phenylene diimine which channels to the protected hapten or the enzyme-inhibitor complex and reacts with p-alkoxy phenol protecting groups to yield exposed haptens or a reactive enzyme. The amplified signal is generated and detected as described above (see, e.g., U.S. Pat. Nos. 5,532,138 and 5,445,944).

An exemplary protocol for performing the proximity assays described herein is provided in Example 4 of PCT Publication No. WO2009/108637, the disclosure of which is herein incorporated by reference in its entirety for all purposes.

In another embodiment, the present invention provides kits for performing the proximity assays described above comprising: (a) a dilution series of one or a plurality of capture antibodies restrained on a solid support; and (b) one or a plurality of detection antibodies (e.g., a combination of activation state-independent antibodies and activation state-dependent antibodies for detecting activation levels and/or a combination of first and second activation state-independent antibodies for detecting expression levels). In some instances, the kits can further contain instructions for methods of using the kit to detect the expression and/or activation status of one or a plurality of signal transduction molecules of cells such as tumor cells. The kits may also contain any of the additional reagents described above with respect to performing the specific methods of the present invention such as, for example, first and second members of the signal amplification pair, tyramide signal amplification reagents, substrates for the facilitating moiety, wash buffers, etc.

VIII. Production of Antibodies

The generation and selection of antibodies not already commercially available for analyzing the expression and/or activation levels of signal transduction molecules (e.g., HER2 and/or c-MET signaling pathway components) in cells such as gastric tumor cells in accordance with the present invention can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., *Guide to Protein Purification*, Murray P. Deutcher, ed., *Meth. Enzymol.*, Vol. 182 (1990); *Solid Phase Peptide Synthesis*, Greg B. Fields, ed., *Meth. Enzymol.*, Vol. 289 (1997); Kiso et al., *Chem. Pharm. Bull.*, 38:1192-99 (1990); Mostafavi et al., *Biomed. Pept. Proteins Nucleic Acids*, 1:255-60, (1995); and Fujiwara et al., *Chem. Pharm. Bull.*, 44:1326-31 (1996). The purified or synthesized polypeptide can then be injected, for example, into mice or rabbits, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic (e.g., retain the functional binding regions of) antibodies can also be prepared from genetic information by various procedures. See, e.g., *Antibody Engineering: A Practical Approach*, Borrebaeck, Ed., Oxford University Press, Oxford (1995); and Huse et al., *J. Immunol.*, 149:3914-3920 (1992).

In addition, numerous publications have reported the use of phage display technology to produce and screen libraries of polypeptides for binding to a selected target antigen (see, e.g., Cwirla et al., *Proc. Natl. Acad. Sci. USA*, 87:6378-6382 (1990); Devlin et al., *Science*, 249:404-406 (1990); Scott et al., *Science*, 249:386-388 (1990); and Ladner et al., U.S. Pat. No. 5,571,698). A basic concept of phage display methods is the establishment of a physical association between a polypeptide encoded by the phage DNA and a target antigen. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target antigen bind to the target antigen and these phage are enriched by affinity screening to the target antigen. The identity of polypeptides displayed from these phage can be determined from their respective genomes. Using these methods, a polypeptide identified as having a binding affinity for a desired target antigen can then be synthesized in bulk by conventional means (see, e.g., U.S. Pat. No. 6,057,098).

The antibodies that are generated by these methods can then be selected by first screening for affinity and specificity with the purified polypeptide antigen of interest and, if required, comparing the results to the affinity and specificity of the antibodies with other polypeptide antigens that are desired to be excluded from binding. The screening procedure can involve immobilization of the purified polypeptide antigens in separate wells of microtiter plates. The solution containing a potential antibody or group of antibodies is then placed into the respective microtiter wells and incubated for about 30 minutes to 2 hours. The microtiter wells are then washed and a labeled secondary antibody (e.g., an anti-mouse antibody conjugated to alkaline phosphatase if the raised antibodies are mouse antibodies) is added to the wells and incubated for about 30 minutes and then washed. Substrate is added to the wells and a color reaction will appear where antibody to the immobilized polypeptide antigen is present.

The antibodies so identified can then be further analyzed for affinity and specificity. In the development of immunoassays for a target protein, the purified target protein acts as a standard with which to judge the sensitivity and specificity of the immunoassay using the antibodies that have been selected. Because the binding affinity of various antibodies may differ, e.g., certain antibody combinations may interfere with one another sterically, assay performance of an antibody may be a more important measure than absolute affinity and specificity of that antibody.

Those skilled in the art will recognize that many approaches can be taken in producing antibodies or binding fragments and screening and selecting for affinity and specificity for the various polypeptides of interest, but these approaches do not change the scope of the present invention.

A. Polyclonal Antibodies

Polyclonal antibodies are preferably raised in animals by multiple subcutaneous (sc) or intraperitoneal (ip) injections of a polypeptide of interest and an adjuvant. It may be useful to conjugate the polypeptide of interest to a protein carrier that is immunogenic in the species to be immunized, such as, e.g., keyhole limpet hemocyanin, serum albumin, bovine thyroglobulin, or soybean trypsin inhibitor using a bifunctional or derivatizing agent. Non-limiting examples of bifunctional or derivatizing agents include maleimidobenzoyl sulfosuccinimide ester (conjugation through cysteine residues), N-hydroxysuccinimide (conjugation through lysine residues), glutaraldehyde, succinic anhydride, $SOCl_2$, and $R_1N\!=\!C\!=\!NR$, wherein R and $R_1$ are different alkyl groups.

Animals are immunized against the polypeptide of interest or an immunogenic conjugate or derivative thereof by combining, e.g., 100 µg (for rabbits) or 5 µg (for mice) of the antigen or conjugate with 3 volumes of Freund's complete adjuvant and injecting the solution intradermally at multiple sites. One month later, the animals are boosted with about ⅕ to ⅒ the original amount of polypeptide or conjugate in Freund's incomplete adjuvant by subcutaneous injection at multiple sites. Seven to fourteen days later, the animals are bled and the serum is assayed for antibody titer. Animals are typically boosted until the titer plateaus. Preferably, the animal is boosted with the conjugate of the same polypeptide, but conjugation to a different immunogenic protein and/or through a different cross-linking reagent may be used. Conjugates can also be made in recombinant cell culture as fusion proteins. In certain instances, aggregating agents such as alum can be used to enhance the immune response.

B. Monoclonal Antibodies

Monoclonal antibodies are generally obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, monoclonal antibodies can be made using the hybridoma method described by Kohler et al., *Nature*, 256:495 (1975) or by any recombinant DNA method known in the art (see, e.g., U.S. Pat. No. 4,816,567).

In the hybridoma method, a mouse or other appropriate host animal (e.g., hamster) is immunized as described above to elicit lymphocytes that produce or are capable of producing antibodies which specifically bind to the polypeptide of interest used for immunization. Alternatively, lymphocytes are immunized in vitro. The immunized lymphocytes are then fused with myeloma cells using a suitable fusing agent, such as polyethylene glycol, to form hybridoma cells (see, e.g., Goding, *Monoclonal Antibodies: Principles and Practice*, Academic Press, pp. 59-103 (1986)). The hybridoma cells thus prepared are seeded and grown in a suitable culture medium that preferably contains one or more substances which inhibit the growth or survival of the unfused, parental myeloma cells. For example, if the parental myeloma cells lack the enzyme hypoxanthine guanine phosphoribosyl transferase (HGPRT), the culture medium for the hybridoma cells will typically include hypoxanthine, aminopterin, and thymidine (HAT medium), which prevent the growth of HGPRT-deficient cells.

Preferred myeloma cells are those that fuse efficiently, support stable high-level production of antibody by the selected antibody-producing cells, and/or are sensitive to a medium such as HAT medium. Examples of such preferred myeloma cell lines for the production of human monoclonal antibodies include, but are not limited to, murine myeloma lines such as those derived from MOPC-21 and MPC-11 mouse tumors (available from the Salk Institute Cell Distribution Center; San Diego, Calif.), SP-2 or X63-Ag8-653 cells (available from the American Type Culture Collection; Rockville, Md.), and human myeloma or mouse-human heteromyeloma cell lines (see, e.g., Kozbor, *J. Immunol.*, 133:3001 (1984); and Brodeur et al., *Monoclonal Antibody Production Techniques and Applications*, Marcel Dekker, Inc., New York, pp. 51-63 (1987)).

The culture medium in which hybridoma cells are growing can be assayed for the production of monoclonal antibodies directed against the polypeptide of interest. Preferably, the binding specificity of monoclonal antibodies produced by hybridoma cells is determined by immunoprecipitation or by an in vitro binding assay, such as a radioimmunoassay (RIA) or an enzyme-linked immunoabsorbent assay (ELISA). The binding affinity of monoclonal antibodies can be determined using, e.g., the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (see, e.g., Goding, *Monoclonal Antibodies: Principles and Practice*, Academic Press, pp. 59-103 (1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody, to induce the synthesis of monoclonal antibodies in the recombinant host cells. See, e.g., Skerra et al., *Curr. Opin. Immunol.*, 5:256-262 (1993); and Pluckthun, *Immunol Rev.*, 130:151-188 (1992). The DNA can also be modified, for example, by substituting the coding sequence for human heavy chain and light chain constant domains in place of the homologous murine sequences (see, e.g., U.S. Pat. No. 4,816,567; and Morrison et al., *Proc. Natl. Acad. Sci. USA*, 81:6851 (1984)), or by covalently joining to the immunoglobulin coding sequence all or part of the coding sequence for a non-immunoglobulin polypeptide.

In a further embodiment, monoclonal antibodies or antibody fragments can be isolated from antibody phage libraries generated using the techniques described in, for example, McCafferty et al., *Nature,* 348:552-554 (1990); Clackson et al., *Nature,* 352:624-628 (1991); and Marks et al., *J. Mol. Biol.,* 222:581-597 (1991). The production of high affinity (nM range) human monoclonal antibodies by chain shuffling is described in Marks et al., *BioTechnology,* 10:779-783 (1992). The use of combinatorial infection and in vivo recombination as a strategy for constructing very large phage libraries is described in Waterhouse et al., *Nuc. Acids Res.,* 21:2265-2266 (1993). Thus, these techniques are viable alternatives to traditional monoclonal antibody hybridoma methods for the generation of monoclonal antibodies.

C. Humanized Antibodies

Methods for humanizing non-human antibodies are known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed by substituting the hypervariable region sequences of a non-human antibody for the corresponding sequences of a human antibody. See, e.g., Jones et al., *Nature,* 321:522-525 (1986); Riechmann et al., Nature, 332:323-327 (1988); and Verhoeyen et al., *Science,* 239:1534-1536 (1988). Accordingly, such "humanized" antibodies are chimeric antibodies (see, e.g., U.S. Pat. No. 4,816,567), wherein substantially less than an intact human variable domain has been substituted by the corresponding sequence from a non-human species. In practice, humanized antibodies are typically human antibodies in which some hypervariable region residues and possibly some framework region (FR) residues are substituted by residues from analogous sites of rodent antibodies.

The choice of human variable domains, both light and heavy, to be used in making the humanized antibodies described herein is an important consideration for reducing antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (see, e.g., Sims et al., *J. Immunol.,* 151:2296 (1993); and Chothia et al., *J. Mol. Biol.,* 196:901 (1987)). Another method uses a particular FR derived from the consensus sequence of all human antibodies of a particular subgroup of light or heavy chains. The same FR may be used for several different humanized antibodies (see, e.g.; Carter et al., *Proc. Natl. Acad. Sci. USA,* 89:4285 (1992); and Presta et al., *J. Immunol.,* 151:2623 (1993)).

It is also important that antibodies be humanized with retention of high affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and specifically involved in influencing antigen binding.

Various forms of humanized antibodies are contemplated in accordance with the present invention. For example, the humanized antibody can be an antibody fragment, such as a Fab fragment. Alternatively, the humanized antibody can be an intact antibody, such as an intact IgA, IgG, or IgM antibody.

D. Human Antibodies

As an alternative to humanization, human antibodies can be generated. In some embodiments, transgenic animals (e.g., mice) can be produced that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggeimann et al., *Year in Immun.,* 7:33 (1993); and U.S. Pat. Nos. 5,591,669, 5,589,369, and 5,545,807.

Alternatively, phage display technology (see, e.g., McCafferty et al., *Nature,* 348:552-553 (1990)) can be used to produce human antibodies and antibody fragments in vitro, using immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats as described in, e.g., Johnson et al., *Curr. Opin. Struct. Biol.,* 3:564-571 (1993). Several sources of V-gene segments can be used for phage display. See, e.g., Clackson et al., *Nature,* 352:624-628 (1991). A repertoire of V genes from unimmunized human donors can be constructed and antibodies to a diverse array of antigens (including self-antigens) can be isolated essentially following the techniques described in Marks et al., *J. Mol. Biol.,* 222:581-597 (1991); Griffith et al., *EMBO J.,* 12:725-734 (1993); and U.S. Pat. Nos. 5,565,332 and 5,573,905.

In certain instances, human antibodies can be generated by in vitro activated B cells as described in, e.g., U.S. Pat. Nos. 5,567,610 and 5,229,275.

E. Antibody Fragments

Various techniques have been developed for the production of antibody fragments. Traditionally, these fragments were derived via proteolytic digestion of intact antibodies (see, e.g., Morimoto et al., *J. Biochem. Biophys. Meth.,* 24:107-117 (1992); and Brennan et al., *Science,* 229:81 (1985)). However, these fragments can now be produced directly using recombinant host cells. For example, the antibody fragments can be isolated from the antibody phage libraries discussed above. Alternatively, Fab'-SH fragments can be directly recovered from E. coli cells and chemically coupled to form F(ab')$_2$ fragments (see, e.g., Carter et al., BioTechnology, 10:163-167 (1992)). According to another approach, F(ab')$_2$ fragments can be isolated directly from recombinant host cell culture. Other techniques for the production of antibody fragments will be apparent to those skilled in the art. In other embodiments, the antibody of choice is a single chain Fv fragment (scFv). See, e.g., PCT Publication No. WO 93/16185; and U.S. Pat. Nos. 5,571,894 and 5,587,458. The antibody fragment may also be a linear antibody as described, e.g., in U.S. Pat. No. 5,641,870. Such linear antibody fragments may be monospecific or bispecific.

F. Bispecific Antibodies

Bispecific antibodies are antibodies that have binding specificities for at least two different epitopes. Exemplary bispecific antibodies may bind to two different epitopes of the same polypeptide of interest. Other bispecific antibodies may combine a binding site for the polypeptide of interest with binding site(s) for one or more additional antigens. Bispecific antibodies can be prepared as full-length antibodies or antibody fragments (e.g., F(ab')$_2$ bispecific antibodies).

Methods for making bispecific antibodies are known in the art. Traditional production of full-length bispecific antibodies is based on the co-expression of two immunoglobulin heavy chain-light chain pairs, where the two chains have different specificities (see, e.g., Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule is usually performed by affinity chromatography. Similar procedures are disclosed in PCT Publication No. WO 93/08829 and Traunecker et al., EMBO J., 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy chain constant region (CH1) containing the site necessary for light chain binding present in at least one of the fusions. DNA encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains into one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. See, e.g., PCT Publication No. WO 94/04690 and Suresh et al., Meth. Enzymol., 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side-chains from the interface of the first antibody molecule are replaced with larger side chains (e.g., tyrosine or tryptophan). Compensatory "cavities" of identical or similar size to the large side-chain(s) are created on the interface of the second antibody molecule by replacing large amino acid side-chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies can be made using any convenient cross-linking method. Suitable cross-linking agents and techniques are well-known in the art, and are disclosed in, e.g., U.S. Pat. No. 4,676,980.

Suitable techniques for generating bispecific antibodies from antibody fragments are also known in the art. For example, bispecific antibodies can be prepared using chemical linkage. In certain instances, bispecific antibodies can be generated by a procedure in which intact antibodies are proteolytically cleaved to generate F(ab')$_2$ fragments (see, e.g., Brennan et al., Science, 229:81 (1985)). These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody.

In some embodiments, Fab'-SH fragments can be directly recovered from E. coli and chemically coupled to form bispecific antibodies. For example, a fully humanized bispecific antibody F(ab')$_2$ molecule can be produced by the methods described in Shalaby et al., J. Exp. Med., 175: 217-225 (1992). Each Fab' fragment was separately secreted from E. coli and subjected to directed chemical coupling in vitro to form the bispecific antibody.

Various techniques for making and isolating bispecific antibody fragments directly from recombinant cell culture have also been described. For example, bispecific antibodies have been produced using leucine zippers. See, e.g., Kostelny et al., J. Immunol., 148:1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VL and VH domains of another fragment, thereby forming two antigen binding sites. Another strategy for making bispecific antibody fragments by the use of single-chain Fv (sFv) dimers is described in Gruber et al., *J. Immunol.*, 152:5368 (1994).

Antibodies with more than two valencies are also contemplated. For example, trispecific antibodies can be prepared. See, e.g., Tutt et al., *J. Immunol.*, 147:60 (1991).

G. Antibody Purification

When using recombinant techniques, antibodies can be produced inside an isolated host cell, in the periplasmic space of a host cell, or directly secreted from a host cell into the medium. If the antibody is produced intracellularly, the particulate debris is first removed, for example, by centrifugation or ultrafiltration. Carter et al., *BioTech.*, 10:163-167 (1992) describes a procedure for isolating antibodies which are secreted into the periplasmic space of *E. coli*. Briefly, cell paste is thawed in the presence of sodium acetate (pH 3.5), EDTA, and phenylmethylsulfonylfluoride (PMSF) for about 30 min. Cell debris can be removed by centrifugation. Where the antibody is secreted into the medium, supernatants from such expression systems are generally concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (see, e.g., Lindmark et al., *J. Immunol. Meth.*, 62:1-13 (1983)). Protein G is recommended for all mouse isotypes and for human γ3 (see, e.g., Guss et al., *EMBO J.*, 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™, chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

One of skill in the art will appreciate that any binding molecule having a function similar to an antibody, e.g., a binding molecule or binding partner which is specific for one or more analytes of interest in a sample, can also be used in the methods and compositions of the present invention. Examples of suitable antibody-like molecules include, but are not limited to, domain antibodies, unibodies, nanobodies, shark antigen reactive proteins, avimers, adnectins, anticalms, affinity ligands, phylomers, aptamers, affibodies, trinectins, and the like.

IX. Methods of Administration

According to the methods of the present invention, the anticancer drugs described herein are administered to a subject by any convenient means known in the art. The methods of the present invention can be used to select a suitable anticancer drug or combination of anticancer drugs for the treatment of a tumor, e.g., gastric (stomach) tumor, in a subject. The methods of the present invention can also be used to identify the response of a tumor, e.g., gastric (stomach) tumor, in a subject to treatment with an anticancer drug or combination of anticancer drugs. In addition, the methods of the present invention can be used to predict the response of a subject having a tumor, e.g., gastric (stomach) tumor, to treatment with an anticancer drug or combination of anticancer drugs. One skilled in the art will appreciate that the anticancer drugs described herein can be administered alone or as part of a combined therapeutic approach with conventional chemotherapy, radiotherapy, hormonal therapy, immunotherapy, and/or surgery.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the subject is treated with one or more anti-signaling agents, anti-proliferative agents, and/or hormonal therapeutic agents in combination with at least one chemotherapeutic agent. Exemplary monoclonal antibodies, tyrosine kinase inhibitors, anti-proliferative agents, chemotherapeutic agents, hormonal therapeutic agents, radiotherapeutic agents, and vaccines are described above.

In some embodiments, the anticancer drugs described herein can be co-administered with conventional immunotherapeutic agents including, but not limited to, immunostimulants (e.g., *Bacillus* Calmette-Guérin (BCG), levamisole, interleukin-2, alpha-interferon, etc.), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

Anticancer drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that an anticancer drug is administered at the same time, just prior to, or just after the administration of a second drug (e.g., another anticancer drug, a drug useful for reducing the side-effects associated with anticancer drug therapy, a radiotherapeutic agent, a hormonal therapeutic agent, an immunotherapeutic agent, etc.).

A therapeutically effective amount of an anticancer drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an anticancer drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anticancer drug.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an anticancer drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An anticancer drug can also be formulated into a suppository disposed, for example, in a polyethylene glycol (PEG) carrier.

Liquid dosage forms can be prepared by dissolving or dispersing an anticancer drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An anticancer drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an anticancer drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized foam. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

A subject can also be monitored at periodic time intervals to assess the efficacy of a certain therapeutic regimen. For example, the activation states of certain signal transduction molecules may change based on the therapeutic effect of treatment with one or more of the anticancer drugs described herein. The subject can be monitored to assess response and understand the effects of certain drugs or treatments in an individualized approach. Additionally, subjects who initially respond to a specific anticancer drug or combination of anticancer drugs may become refractory to the drug or drug combination, indicating that these subjects have developed acquired drug resistance. These subjects can be discontinued on their current therapy and an alternative treatment prescribed in accordance with the methods of the present invention.

In certain aspects, the methods described herein can be used in conjunction with panels of gene expression markers that predict the likelihood of stomach cancer prognosis and/or recurrence in various populations. These gene panels can be useful for identifying individuals who are unlikely to experience recurrence and, thus, unlikely to benefit from adjuvant chemotherapy. The expression panels can be used to identify individuals who can safely avoid adjuvant chemotherapy, without negatively affecting disease-free and overall survival outcomes. Suitable systems include, but are not limited to, Oncotype DX™, which is a 21-gene panel from Genomic Health, Inc.; MammaPrint,® which is a 70-gene panel from Agendia; and a 76-gene panel from Veridex.

In addition, in certain other aspects, the methods described herein can be used in conjunction with panels of gene expression markers that identify the original tumors for cancers of unknown primary (CUP). These gene panels can be useful in identifying patients with metastatic cancer who would benefit from therapy consistent with that given to patients diagnosed initially with stomach cancer. Suitable systems include, but are not limited to, the Aviara Cancer-TYPE ID assay, an RT-PCR-based expression assay that measures 92 genes to identify the primary site of origin for 39 tumor types; and the Pathwork® Tissue of Origin Test, which measures the expression of more than 1600 genes on a microarray and compares a tumor's gene expression "signature" against those of 15 known tissue types."

X. Examples

The following examples are offered to illustrate, but not to limit, the claimed invention.

Example 1

Isolation, Stimulation, and Lysis of Circulating Cells

Circulating cells of a solid tumor comprise cells that have either metastasized or micrometastasized from a solid tumor and include circulating tumor cells (CTCs), cancer stem cells (CSCs), and/or cells that are migrating to the tumor (e.g., circulating endothelial progenitor cells (CEPCs), circulating endothelial cells (CECs), circulating pro-angiogenic myeloid cells, circulating dendritic cells, etc.). Patient samples containing circulating cells can be obtained from any accessible biological fluid (e.g., whole blood, serum, plasma, ductal lavage fluid, nipple aspirate, lymph, urine, saliva, fine needle aspirate, etc.). The circulating cells can be isolated from a patient sample using one or more separation methods such as, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), the CellTrack™ System by Immunicon (Huntingdon Valley, Pa.), microfluidic separation (see, e.g., Mohamed et al., *IEEE Trans. Nanobiosci.*, 3:251-256 (2004); Lin et al., Abstract No. 5147, 97th AACR Annual Meeting, Washington, D.C. (2006)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J. Oncol.*, 21:521-530 (2002)).

Manual Isolation of CTCs:

Immunomagnetic separation of CTCs—manual isolation followed by an activation assay:
1) Magnetic beads (Dynal M450; Dynal AS; Oslo, Norway) that have been previously conjugated to an anti-EpCAM monoclonal antibody (Kordia Life Sciences; Leiden, The Netherlands) are used. Alternatively, polyclonal antibodies or mixtures of monoclonal antibodies can be used.
2) Just prior to use, the pre-coated Dynabeads are washed once in an equal volume of PBS with BSA at 0.01%.
3) 25 µl of the pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample Preparation:
1) Peripheral blood from human subjects is drawn in a siliconized tube containing 1 mg/ml EDTA. The first 3-5 ml is discarded to avoid contamination with epithelial cells released from the punctured vein.
2) 1 ml of whole blood is diluted 1:3 with 0.9% NaCl prior to use.

Control Preparation:
1) Cell line controls are made by spiking human cancer cell lines into HL-60 cells.
2) Cell line controls are made by spiking human cancer cell lines into whole blood from healthy donors.

Manual Isolation of CECs and CEPCs:

As a non-limiting example, viable CECs and CEPCs can be isolated using the immunomagnetic isolation/enrichment technique described in Beerepoot et al., *Ann. Oncology*, 15:139-145 (2004). Briefly, peripheral blood is incubated with magnetic beads (Dynal M450 IgG$_1$) that have been previously conjugated to an anti-CD146 monoclonal antibody (Kordia Life Sciences). This antibody recognizes all lineages of endothelial cells, but not hematopoetic or epithelial cells, in peripheral blood (George et al., *J. Immunol. Meth.*, 139:65-75 (1991)). Negative selection of hematopoetic and epithelial cells can be used prior to the positive selection with magnetic beads conjugated to appropriate antibodies (e.g., Dynal-CD45 beads for depleting leukocytes, Dynal-CD14 beads for depleting monocytes, Dynal-EpCAM for depleting epithelial cells (Invitrogen; Carlsbad, Calif.)). In this example, only positive selection is used.

Immunomagnetic separation of CECs and CEPCs—manual isolation followed by an activation assay:
1) Magnetic beads (Dynal M450) that have been previously conjugated to an anti-CD146 monoclonal antibody (Kordia Life Sciences) are used.
2) Just prior to use, the pre-coated Dynabeads are washed once in an equal volume of PBS with BSA at 0.01%.
3) 25 µl pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample Preparation:
1) Peripheral blood from human subjects is drawn in a siliconized tube containing 1 mg/ml EDTA. The first 3-5 ml is discarded to avoid contamination with endothelial cells released from the punctured vein.
2) 1 ml of whole blood is diluted 1:3 with 0.9% NaCl prior to use.

Control Preparation:
1) Cell line controls are made by spiking human umbilical vein endothelial cells (HUVEC) into HL-60 cells.
2) Cell line controls are made by spiking human umbilical vein endothelial cells (HUVEC) into whole blood donated by healthy individuals.

Manual Isolation of CEPCs (without CECs):

CEPCs are a circulating subtype of bone marrow-derived progenitor cells that have the capacity of differentiating into mature endothelial cells in response to various angiogenic growth factors. CEPCs may be isolated by selection with antibodies recognizing the surface marker CD34. CD133 is a surface marker that differentiates immature endothelial progenitor cells (EPCs) or primitive hematopoetic stem cells (HSCs) from CEPCs. Various isolation procedures of CEPCs from different sources have been described using adherence culture or magnetic microbeads. In this example, a protocol modified from that described in Asahara et al., *Science*, 275:964-967 (1997) is used.

Immunomagnetic separation of CEPCs—manual isolation followed by an activation assay:
1) Magnetic beads (Dynal M450 CD34) are used. These beads are coated with a monoclonal antibody specific for the CD34 surface antigen.
2) Just prior to use, the pre-coated Dynabeads are washed once in an equal volume of PBS with BSA at 0.01%.
3) 25 µl pre-coated Dynabeads are added to 1 ml of the sample.
4) The mixture is incubated for 20 minutes at 2-8° C. with gentle tilting and rotation.
5) The tube is placed in the magnetic separator (MPL-1 magnet) for 2 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample Preparation:
1) Peripheral blood from human subjects is drawn in a siliconized tube containing 1 mg/ml EDTA. The first 3-5 ml is discarded to avoid contamination with endothelial cells released from the punctured vein.
2) 10 ml of blood is diluted 1:1 with a balanced salt solution.
3) 4 ml of diluted blood is layered onto 3 ml of Ficoll-Paque in 10 ml tubes.
4) Tubes are spun at 400×g for 30-40 min at 18-20° C.
5) The upper layer containing plasma and platelets is drawn off using a sterile Pasteur pipette, leaving the layer of mononuclear cells undisturbed at the interface.
6) The mononuclear cells are transferred to a sterile centrifuge tube using a sterile pipette.
7) 6 ml of balanced salt solution is added and the cells are gently resuspended.
8) The mixture is centrifuged at 60-100×g for 10 min at 18-20° C.
9) The supernatant is removed and the mononuclear cells from each tube are resuspended in 1 ml PBS.

Cell Isolation of CTCs, CECs, and CEPCs using the Veridex System:
Veridex, LLC (Warren, N.J.) has commercialized the CellSearch system, which consists of the CellTracks® AutoPrep® System, the CellSearch™ Epithelial Cell Kit, and the CellTracks® Analyzer. The CellTracks® AutoPrep® System is a semi-automated sample preparation system (Kagan et al., *J. Clin. Ligand Assay*, 25:104-110 (2002)). The CellSearch™ Epithelial Cell Kit consists of: ferrofluids coated with anti-EpCAM antibodies specific for epithelial cells; phycoerythrin-conjugated antibodies to cytokeratins 8, 18, and 19; an anti-CD45 antibody conjugated to allophycocyanin; DAPI dye; and buffers for washing, permeabilizing, and resuspending the cells. The protocol used in this example is also described in Allard et al., *Clin. Cancer Res.*, 10:6897-6904 (2004). The entire Veridex system can be used for CTC enumeration or, by removing the sample manually after isolation with the CellTracks® AutoPrep® System, can provide a method of isolation prior to analysis for pathway activation. The number of CTCs can be informative for algorithm development.

Veridex System—CTC Enrichment Followed by Enumeration:
1) 7.5 ml of blood are mixed with 6 ml of buffer, centrifuged at 800×g for 10 minutes, and then placed on the CellTracks® AutoPrep® System.
2) After the instrument aspirates the supernatant, the instrument adds the ferrofluids.
3) The instrument performs the incubation and subsequent magnetic separation step.
4) Unbound cells and the remaining plasma are aspirated.
5) Staining reagents are added in conjunction with the permeabilization buffer for fluorescence staining.
6) After incubation by the system, the cells are again separated magnetically and resuspended in the MagNest® cell presentation device.
7) The MagNest® cell presentation device is then placed on the CellTracks®Analyzer, a four-color semi-automated fluorescence microscope.
8) Images are captured that meet the Veridex defined criteria and are shown via a web-based browser for final manual selection.
9) Results of cell enumeration are expressed as the number of cells per 7.5 ml of blood.

Veridex system—CTC enrichment followed by an activation assay:
1) 7.5 ml of blood are mixed with 6 ml of buffer, centrifuged at 800×g for 10 minutes, and then placed on the CellTracks® AutoPrep® System.
2) After the instrument aspirates the supernatant, the instrument adds the ferrofluids.
3) The instrument performs the incubation and subsequent magnetic separation step.
4) Unbound cells and the remaining plasma are aspirated.
5) The sample is resuspended in 100 µl of stimulation buffer.

Veridex system—CEC and CEPC enrichment followed by an activation assay:
1) Veridex offers a CellSearch™ Endothelial Cell Kit utilizing capture with an anti-CD146 antibody. The CellSearch™ Endothelial Cell Kit is used in conjunction with the CellTracks® AutoPrep® System for blood sample preparation and the CellTracks® Analyzer to count and characterize CECs and CEPCs from whole blood. The protocol is the same as for the CellSearch™ Epithelial Cell Kit.

Sample preparation:
1) Enumeration: Peripheral blood from human subjects is drawn in the CellSave Preservative Tube according to manufacturer's instructions. The first 3-5 ml is discarded to avoid contamination with epithelial or endothelial cells released from the punctured vein.
2) Pathway analysis: Peripheral blood from human subjects is drawn in a siliconized tube containing 1 mg/ml EDTA. The first 3-5 ml is discarded to avoid contamination with epithelial or endothelial cells released from the punctured vein.

Manual Isolation of CSCs:
Evidence is building that tumors contain a small population of putative cancer stem cells with unique self-renewal and survival mechanisms (see, e.g., Sells, *Crit. Rev. Oncol. Hematol.*, 51:1-28 (2004); Reya et al., *Nature*, 414:105-111 (2001); Dontu et al., *Trends Endocrinol. Metal.*, 15:193-197 (2004); and Dick, *Nature*, 423:231-233 (2003)). Cancer stem cells (CSCs) may exist in a quiescent state for a long time, making them resistant to chemotherapeutic drugs which target dividing cells. This cancer-initiating population can be characterized for activation of self-renewal and survival pathways subject to targeted therapy for selective removal. Isolation procedures of CSCs have been described using adherence culture or magnetic microbeads. In this example, a protocol modified from that described in Cote et al., *Clin. Can. Res.*, 12:5615 (2006) is used.

Immunomagnetic CSC isolation—manual isolation followed by an activation assay:
1) Magnetic beads (Dynal AS; Oslo, Norway) are used. These beads are coated with a monoclonal antibody specific for either the CD34 or CD133 surface antigen.
2) Just prior to use, the pre-coated Dynabeads are washed once in an equal volume of PBS with BSA at 0.01%.
3) $1\text{-}10^7$ pre-coated Dynabeads are added to 3 ml of the sample.
4) The mixture is incubated for 60 minutes at 2-8° C. with gentle tilting and rotating.
5) The mixture is divided into 1 ml portions and each tube is placed in the magnetic separator (MPL-1 magnet) for at least 6 minutes.
6) The supernatant is discarded and the bead-bound cells are washed three times by resuspending in PBS with BSA at 0.01% followed by magnetic separation.
7) The sample is resuspended in 100 µl of stimulation buffer.

Sample preparation:
1) Bone marrow specimens are obtained from cancer patients following patient informed consent.
2) Processing the bone marrow aspirates is performed as described in Bauer et al., *Clin. Can. Res.*, 6:3552-3559 (2000). The mononuclear cell fraction containing any disseminated tumor cells is enriched by Ficoll-Hypaque density gradient centrifugation using a Beckman GS-6 centrifuge at 4000×g for 35 minutes and washed twice with PBS.

Cell Stimulation and Lysis of Isolated CTCs:
Cell stimulation:
1) Growth factors TGF-α (100 nM), Hrg (100 nM), and/or IGF (100 nM) are added to the cells and incubated at 37° C. for 5 minutes.

Cell stimulation with drug treatment:
1) Sample is incubated with Herceptin, Lapatinib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is incubated with Herceptin, Lapatinib, Tarceva, and/or Rapamycin analogs at therapeutically effective concentrations for 30 min. at 37° C.
2) Cells are then stimulated by TGF-α (100 nM), Hrg (100 nM), and/or IGF (100 nM) and incubated at 37° C. for 120 minutes.

Stimulated CTCs are lysed using the following protocol:
1) Fresh lysis buffer is freshly prepared by mixing the reagents set forth in Table 3.
2) After the final wash, cells are resuspended on ice in 100 µl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

TABLE 3

Lysis Buffer Recipe (10 ml)

| Reagents | Stock conc. | Final conc. | Volume |
|---|---|---|---|
| 10% Triton X-100 | 10 | 1 | 1.00 |
| 1M Tris, pH 7.5 | 1 | 0.05 | 0.05 |
| 1M NaF | 1 | 0.05 | 0.05 |
| 5M NaCl | 5 | 0.1 | 0.20 |
| 2M B-glycerolphosphate | 1 | 0.05 | 0.50 |
| 0.1M $Na_3VO_4$ | 0.1 | 0.001 | 0.10 |
| 1 mg/ml pepstatin | 1 | 0.10 | |
| Complete mini protease | | | 1 tablet |
| 0.5M EDTA | 0.5 | 0.005 | 0.10 |
| | | Total (ml) | 3.00 |
| | | Water (ml) | 7.00 |

Cell Stimulation and Lysis of Isolated CECs and/or CEPCs:
VEGF is thought to promote survival by activating anti-apoptotic pathways in both CEPCs (Larrivee et al., *J. Biol. Chem.*, 278:22006-22013 (2003)) and mature CECs, which have been sloughed off the vessel wall (Solovey et al., *Blood*, 93:3824-3830 (1999)). VEGF may also stimulate the proliferation of CEPCs or mature CECs, although mature CECs seem to have only a limited proliferative capacity compared with CEPCs (Lin et al., *J. Clin. Invest.*, 105:71-77 (2000)). For these reasons, CECs and/or CEPCs are activated by incubation with VEGF family growth factors prior to lysis.

Cell stimulation:
1) The growth factors VEGF, FGF, PDGF, P1GF, and/or Ang, each at 100 nM, are added to the cells and incubated at 37° C. for 5 minutes.

Cell stimulation with drug treatment:
1) Sample is incubated with Avastin, Nexavar, Sutent, and/or Rapamycin analogs at therapeutically effective concentrations for 30 min. at 37° C.
2) Cells are then stimulated by adding factors VEGF, FGF, PDGF, PIGF, and/or Ang, each at 100 nM, and incubated at 37° C. for 5 minutes.

Cell stimulation with drug treatment (feedback loop):
1) Sample is incubated with Avastin, Nexavar, Sutent, and/or Rapamycin analogs at therapeutically effective concentrations for 30 min. at 37° C.
2) Cells are then stimulated by adding VEGF, FGF, PDGF, PIGF, and/or Ang, each at 100 nM, and incubated at 37° C. for 120 minutes.

Isolated CECs and/or CEPC cells are lysed using the following protocol:
1) Fresh lysis buffer is freshly prepared by mixing the reagents set forth in Table 3.
2) After the final wash, cells are resuspended on ice in 100 µl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Cell Stimulation and Lysis of Isolated CSCs:
Stimulated cells:
1) Growth factors TGF-α (100 nM), Hrg (100 nM), and/or IGF (100 nM) are added to the cells and incubated at 37° C. for 5 minutes.

Stimulated cells with drug treatment:
1) Sample is incubated with Herceptin, Lapatinib, Tarceva, and/or Rapamycin analogs at therapeutically effective concentrations for 30 min. at 37° C.

2) Cells are then stimulated by adding factors TGF-α (100 nM), Hrg (100 nM), and/or IGF (100 nM) and incubated at 37° C. for 5 minutes.

Stimulated cells with drug treatment (feedback loop):
1) Sample is incubated with Herceptin, Lapatinib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 120 minutes.

Isolated CSC cells are lysed using the following protocol:
1) Fresh lysis buffer is freshly prepared by mixing the reagents set forth in Table 3.
2) After the final wash, cells are re-suspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Example 2

Preparation of Tumor Cell Extracts from Tissue, Biopsy, or Primary Cultures

This example illustrates methods for isolating, stimulating, and lysing cells from tumor tissue or biopsy specimens. This example also illustrates methods for initiating, stimulating, and lysing primary cultures of tumor cells isolated from tissue, biopsy, or whole blood. Additional methods for isolating and culturing tumor cells from biological specimens for screening chemotherapeutic agents are described, e.g., in U.S. Pat. Nos. 5,728,541; 6,416,967; 6,887,680; 6,900,027; 6,933,129; and 7,112,415; and in U.S. Patent Publication Nos. 20040023375 and 20050202411. The cellular extracts prepared in accordance with this example can be used in the single detection or proximity assays described herein.

Isolation of Tumor Cells from Primary or Metastatic Tissues:
Cell Isolation and Culture:
1) Approximately 5-100 mg non-necrotic, non-contaminated tumor tissue are harvested surgically and placed into 100 ml bottle containing sterile cell culture media (e.g., RMPI-1640 with 10% FBS and antibiotics).
2) Samples can be stored or shipped at room temperature within 72 hours of extraction.
3) Samples are rinsed three times in cell culture media.
4) The tissue is minced into small pieces with a scalpel and then disaggregated into a cell suspension by passing through a fine wire mesh.
5) Alternatively, minced tissue is treated with a cocktail containing 0.25% Collagenase II and 0.001% DNase diluted in serum-free cell culture media containing antibiotics. Incubation is for 15-20 min with gentle agitation. Enzymes are removed after treatment by washing 3 times with cell culture media.
6) Cell concentration is adjusted to $10^6$/ml and cells are seeded into 6-well plates and allowed to settle overnight. The following day, the cells are trypsinized and re-seeded into microtiter plates for stimulation with ligands and/or inhibition with targeted drugs.

Cell Stimulation and Lysis of Cells from Disaggregated Tumors:
Cell stimulation:
1) Growth factors TGF-α (100 nM), Hrg (100 nM), and/or IGF (100 nM) are added to the cells and incubated at 37° C. for 5 minutes.

Cell stimulation with drug treatment:
1) Sample is incubated with Herceptin, Lapatinib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is incubated with Herceptin, Lapatinib, Tarceva, and/or Rapamycin analogs at therapeutically effective concentrations for 30 min. at 37° C.
2) Cells are then stimulated by TGF-α (100 nM), Hrg (100 nM), and/or IGF (100 nM) and incubated at 37° C. for 120 minutes.

Stimulated cells are lysed using the following protocol:
1) Fresh lysis buffer is freshly prepared by mixing the reagents set forth in Table 3 above.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Isolation of Tumor Cells from Biopsy Specimens:
Cell isolation and culture:
1) Core biopsies are extracted surgically (2 cores for 14 gauge needles, 3 cores for 16 gauge needles, and 4 cores for 18 gauge needles, with 1-2 biopsies for vacuum-assisted biopsies) and placed into a 10 ml sterile vial containing cell culture media as for tumor specimens.
2) Samples can be stored or shipped at room temperature within 72 hours of extraction.
3) Cellular material from core biopsies is disaggregated into a cell suspension by passing through a fine wire mesh.
4) Alternatively, biopsies may be treated with a cocktail containing 0.25% Collagenase II and 0.001% DNase diluted in cell culture media containing antibiotics. Incubation is for 15-20 min with gentle agitation. Enzymes are removed after treatment by washing 3 times with cell culture media.
5) Cell concentration is adjusted to $10^6$/ml and cells are seeded into 6-well plates and allowed to settle overnight. The following day, the cells are trypsinized and re-seeded into microtiter plates for stimulation with ligands and/or inhibition with targeted drugs.

Cell Stimulation and Lysis of Cells from Biopsies:
Cell stimulation:
1) Growth factors TGF-α (100 nM), Hrg (100 nM), and/or IGF (100 nM) are added to the cells and incubated at 37° C. for 5 minutes.

Cell stimulation with drug treatment:
1) Sample is incubated with Herceptin, Lapatinib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is incubated with Herceptin, Lapatinib, Tarceva, and/or Rapamycin analogs at therapeutically effective concentrations for 30 min. at 37° C.
2) Cells are then stimulated by TGF-α (100 nM), Hrg (100 nM), and/or IGF (100 nM) and incubated at 37° C. for 120 minutes.

Stimulated cells are lysed using the following protocol:
1) Fresh lysis buffer is freshly prepared by mixing the reagents set forth in Table 3 above.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Initiation of Primary Cultures from Tumor Cells Isolated from Tissue, Biopsy, or Whole Blood:

Cell culture:
1) Tumor cells isolated from tissue, biopsy, or whole blood as described above are cultured in small sterile flasks (e.g., T-25), Petri dishes (e.g., 10 mm), or plates (e.g., 24-well plates) depending on the number of isolated tumor cells.
2) Incubation is done in cell culture media (e.g., RMPI-1640 with 2% FBS and antibiotics) in a humidified 37° C. incubation supplemented with 5% $CO_2$. Over time, cells form a monolayer on the bottom of the vessel and begin to divide. When the cells are close to confluence, they are trypsinized and re-seeded into microtiter plates for stimulation with ligands and/or inhibition with targeted drugs.

Cell Stimulation and Lysis of Primary Cultures from Tumor Cells Isolated from Tissue, Biopsy, or Whole Blood:

Cell stimulation:
1) Growth factors TGF-α (100 nM), Hrg (100 nM), and/or IGF (100 nM) are added to the cells and incubated at 37° C. for 5 minutes.

Cell stimulation with drug treatment:
1) Sample is incubated with Herceptin, Lapatinib, Tarceva, and/or Rapamycin analogs at therapeutically effective concentrations for 30 min. at 37° C.
2) Cells are then stimulated by adding factors TGF-α (100 nM), Hrg (100 nM), and/or IGF (100 nM) and incubated at 37° C. for 5 minutes.

Cell stimulation with drug treatment (feedback loop):
1) Sample is incubated with Herceptin, Lapatinib, Tarceva, and/or Rapamycin analogs at therapeutically effective concentrations for 30 min. at 37° C.
2) Cells are then stimulated by TGF-α (100 nM), Hrg (100 nM), and/or IGF (100 nM) and incubated at 37° C. for 120 minutes.

Stimulated cells are lysed using the following protocol:
1) Fresh lysis buffer is freshly prepared by mixing the reagents set forth in Table 3 above.
2) After the final wash, cells are resuspended on ice in 100 μl of chilled buffer.
3) Incubation is performed on ice for 30 minutes.
4) The mixture is spun in a microfuge at maximum speed for 10 minutes to separate the beads from the lysate.
5) The lysate is transferred to a new tube for assay or storage at −80° C.

Example 3

Single Detection Microarray ELISA with Tyramide Signal Amplification

This example illustrates a multiplex, high-throughput, single detection microarray ELISA having superior dynamic range that is suitable for analyzing the activation states of signal transduction molecules in rare circulating cells:
1) Capture antibody was printed on a 16-pad FAST slide (Whatman Inc.; Florham Park, N.J.) with a 2-fold serial dilution.
2) After drying overnight, the slide was blocked with Whatman blocking buffer.
3) 80 μl of cell lysate was added onto each pad with a 10-fold serial dilution. The slide was incubated for two hours at room temperature.
4) After six washes with TBS-Tween, 80 μl of biotin-labeled detection antibody (e.g., a monoclonal antibody recognizing phosphorylated c-Met or a monoclonal antibody recognizing c-Met regardless of activation state) was incubated for two hours at room temperature.
5) After six washes, streptavidin-labeled horseradish peroxidase (SA-HRP) was added and incubated for 1 hour to allow the SA-HRP to bind to the biotin-labeled detection antibody.
6) For signal amplification, 80 μl of biotin-tyramide at 5 μg/ml was added and reacted for 15 minutes. The slide was washed six times with TBS-Tween, twice with 20% DMSO/TBS-Tween, and once with TBS.
7) 80 μl of SA-Alexa 555 was added and incubated for 30 minutes. The slide was then washed twice, dried for 5 minutes, and scanned on a microarray scanner (Perkin-Elmer, Inc.; Waltham, Mass.).

Example 4

Proximity Dual Detection Microarray ELISA with Tyramide Signal Amplification

This example illustrates a multiplex, high-throughput, proximity dual detection microarray ELISA having superior dynamic range that is suitable for analyzing the activation states of signal transduction molecules in rare circulating cells:
1) Capture antibody was printed on a 16-pad FAST slide (Whatman Inc.) with a serial dilution ranging from 1 mg/ml to 0.004 mg/ml.
2) After drying overnight, the slide was blocked with Whatman blocking buffer.
3) 80 μl of A431 cell lysate was added onto each pad with a 10-fold serial dilution.
The slide was incubated for two hours at room temperature.
4) After six washes with TBS-Tween, 80 μl of detection antibodies for the proximity assay diluted in TBS-Tween/2% BSA/1% FBS was added to the slides. The incubation was for 2 hours at room temperature.
   a) As a non-limiting example, the detection antibodies can comprise the following: (i) an anti-c-Met monoclonal antibody that is directly conjugated to glucose oxidase (GO); and (ii) a monoclonal antibody recognizing phosphorylated c-Met that is directly conjugated to horseradish peroxidase (HRP).

b) Alternatively, the detection step can utilize a biotin-conjugate of the monoclonal antibody recognizing phosphorylated c-Met. In these instances, after six washes, an additional sequential step of incubation with streptavidin-HRP for 1 hour is included.

c) Alternatively, the detection step can utilize an oligonucleotide-mediated glucose oxidase (GO) conjugate of the anti-c-Met antibody. Either the directly conjugated or the biotin-steptavidin (SA) linked conjugate of HRP to the phosphorylated c-Met antibody can be used.

5) For signal amplification, 80 µl of biotin-tyramide at 5 µg/ml was added and reacted for 15 min. The slide was washed six times with TBS-Tween, twice with 20% DMSO/TBS-Tween, and once with TBS.

6) 80 µl of SA-Alexa 555 was added and incubated for 30 min. The slide was then washed twice, dried for 5 minutes, and scanned on a microarray scanner (Perkin-Elmer, Inc.).

Example 5

Generation of Activation Profiles for Drug Selection

Figure 2:
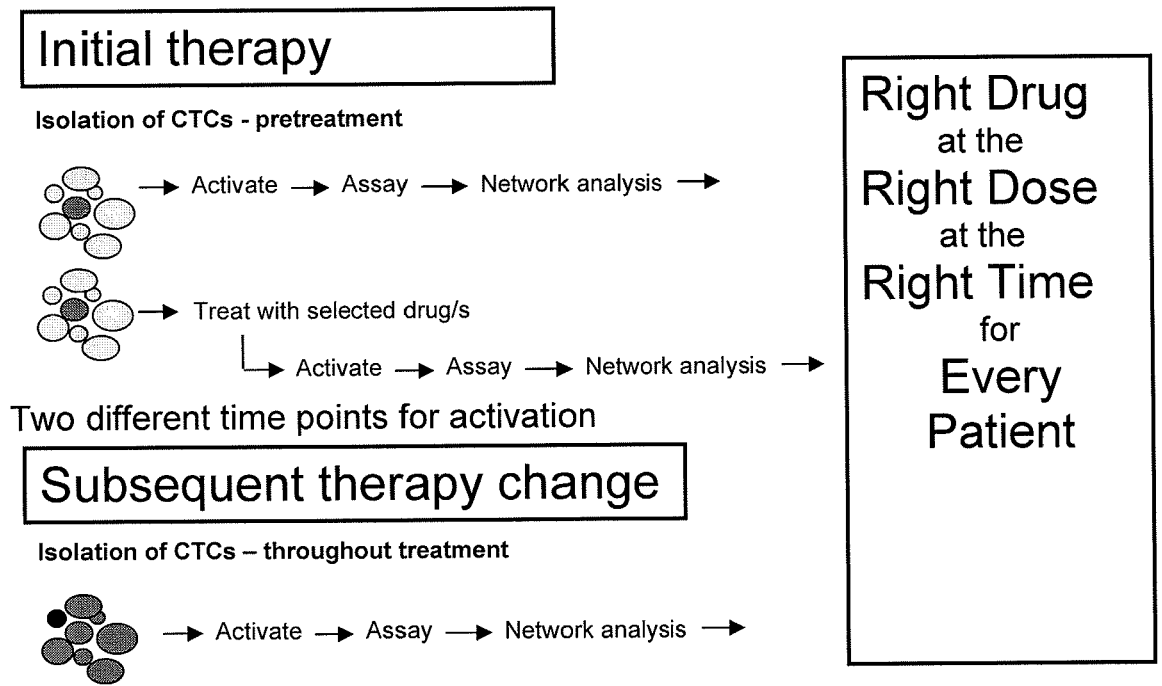
FIG. 2 shows schematically the application of the addressable arrays of the invention for drug selection throughout the course of cancer treatment.

The methods and compositions of the present invention can be applied for drug selection for cancer treatment. A typical protocol entails the generation of two profiles, a reference activation profile and a test activation profile, which are then compared to determine the efficacy of a particular drug treatment regimen (see, FIG. 2).

Reference Activation Profile

To derive a reference activation profile, a blood or fine needle aspirate (FNA) sample is obtained from a patient having a specific type of cancer (e.g., gastric cancer) prior to anticancer drug treatment. Rare circulating cells derived from the cancerous tumor are isolated from the blood sample or tumor cells are isolated from the FNA sample using, e.g., immunomagnetic separation techniques as described in greater detail herein. The isolated cells can be stimulated in vitro with one or more growth factors. The stimulated cells are then lysed to produce a cellular extract. The cellular extract is applied to an addressable array containing a dilution series of a panel of capture antibodies specific for signal transduction molecules whose activation states may be altered in the patient's type of cancer. Single detection or proximity assays are performed using the appropriate detection antibodies (e.g., activation state-independent antibodies and/or activation state-dependent antibodies) to determine the activation state of each signal transduction molecule of interest. The "Pathway Selection" table shown in Table 2 is particularly useful for selecting which activation states to detect based upon the patient's type of cancer. For example, one patient may have a type of cancer that displays the activation states of the EGFR pathway set forth in "Pathway 1" of Table 2. Alternatively, another patient may have another type of cancer that displays the activation states of the EGFR pathway set forth in "Pathway 2" of Table 2. A reference activation profile is thus generated providing the activation states of signal transduction molecules in the patient's cancer in the absence of any anticancer drugs.

Test Activation Profile

To obtain a test activation profile, a second blood or FNA sample is obtained from the patient having the specific type of cancer (e.g., gastric cancer) either prior to anticancer drug treatment or after administration of an anticancer drug (e.g., at any time throughout the course of cancer treatment). Rare circulating cells derived from the cancerous tumor are isolated from the blood sample or tumor cells are isolated from the FNA sample. If isolated cells are obtained from a patient who has not received treatment with an anticancer drug, the isolated cells are incubated with anticancer drugs which target one or more of the activated signal transduction molecules determined from the reference activation profile described above. The "Drug Selection" table (Table 1) is particularly useful for selecting appropriate anticancer drugs that are either approved or in clinical trials which inhibit specific activated target signal transduction molecules. For example, if it is determined from the reference activation profile that EGFR is activated, then the cells can be incubated with one or more of the drugs listed in column "A" or "B" of Table 1. The isolated cells can then be stimulated in vitro with one or more growth factors. The isolated cells are then lysed to produce a cellular extract. The cellular extract is applied to the addressable array and proximity assays are performed to determine the activation state of each signal transduction molecule of interest. A test activation profile for the patient is thus generated providing the activation states of signal transduction molecules in the patient's cancer in the presence of specific anticancer drugs.

Drug Selection

The anticancer drugs are determined to be suitable or unsuitable for treatment of the patient's cancer by comparing the test activation profile to the reference activation profile. For example, if drug treatment causes most or all of the signal transduction molecules to be substantially less activated than in the absence of the drugs, e.g., a change from strong activation without the drugs to weak or very weak activation with the drugs, then the treatment is determined to be suitable for the patient's cancer. In such instances, treatment is either initiated with the suitable anticancer drug in a patient who has not received drug therapy or subsequent treatment is continued with the suitable anticancer drug in a patient already receiving the drug. However, if the drug treatment is deemed unsuitable for treatment of the patient's cancer, different drugs are selected and used to generate a new test activation profile, which is then compared to the reference activation profile. In such instances, treatment is either initiated with a suitable anticancer drug in a patient who has not received drug therapy or subsequent treatment is changed to a suitable anticancer drug in a patient currently receiving the unsuitable drug.

Example 6

Method to Detect c-Met Activation for Anticancer Drug Therapy Selection

This example illustrates the use of the multiplexed protein microarray platform described herein to identify patients who would respond to anti-c-Met inhibitors and to identify patients who would benefit from a combination of anti-c-Met inhibitors with other targeted agents.

A wide variety of human malignancies exhibit sustained c-Met stimulation, overexpression, or mutation, including carcinomas of the breast, liver, lung, ovary, kidney, and thyroid. Notably, activating mutations in c-Met have been positively identified in patients with a particular hereditary form of papillary renal cancer, directly implicating c-Met in human tumorigenesis. Aberrant signaling of the c-Met signaling pathway due to dysregulation of the c-Met receptor or overexpression of its ligand, hepatocyte growth factor (HGF), has been associated with an aggressive phenotype.

Extensive evidence that c-Met signaling is involved in the progression and spread of several cancers and an enhanced understanding of its role in disease have generated considerable interest in c-Met and HGF as major targets in cancer drug development. This has led to the development of a variety of c-Met pathway antagonists with potential clinical applications. The three main approaches of pathway-selective anticancer drug development have included antagonism of ligand/receptor interaction, inhibition of the tyrosine kinase catalytic activity, and blockade of the receptor/effector interaction.

Several c-Met antagonists are now under clinical investigation. Preliminary clinical results of several of these agents, including both monoclonal antibodies and small-molecule tyrosine kinase inhibitors, have been encouraging. Interestingly, patients with c-Met amplification do not respond to tyrosine kinase inhibitors. Several multi-targeted therapies have also been under investigation in the clinic and have demonstrated promise, particularly with regard to tyrosine kinase inhibition.

The c-Met receptor tyrosine kinase can be overexpressed in many malignancies and is important in biological and biochemical functions. Activation of the c-Met receptor can lead to increased cell growth, invasion, angiogenesis, and metastasis. Amplification and/or activation mutations within the tyrosine kinase domain, juxtamembrane domain, or semaphorin domain have been identified for c-Met. A number of therapeutic strategies have been employed to inhibit c-Met. Several clinical trials are investigating c-Met and its ligand, hepatocyte growth factor, for various malignancies. As such, methods for profiling c-Met phosphorylation in the limited number of cancer cells found in a patient's whole blood or fine needle aspirate (FNA) sample provide valuable insight into the overall disease pathogenesis, and therefore lead to better anticancer therapy selection.

Figure 3:
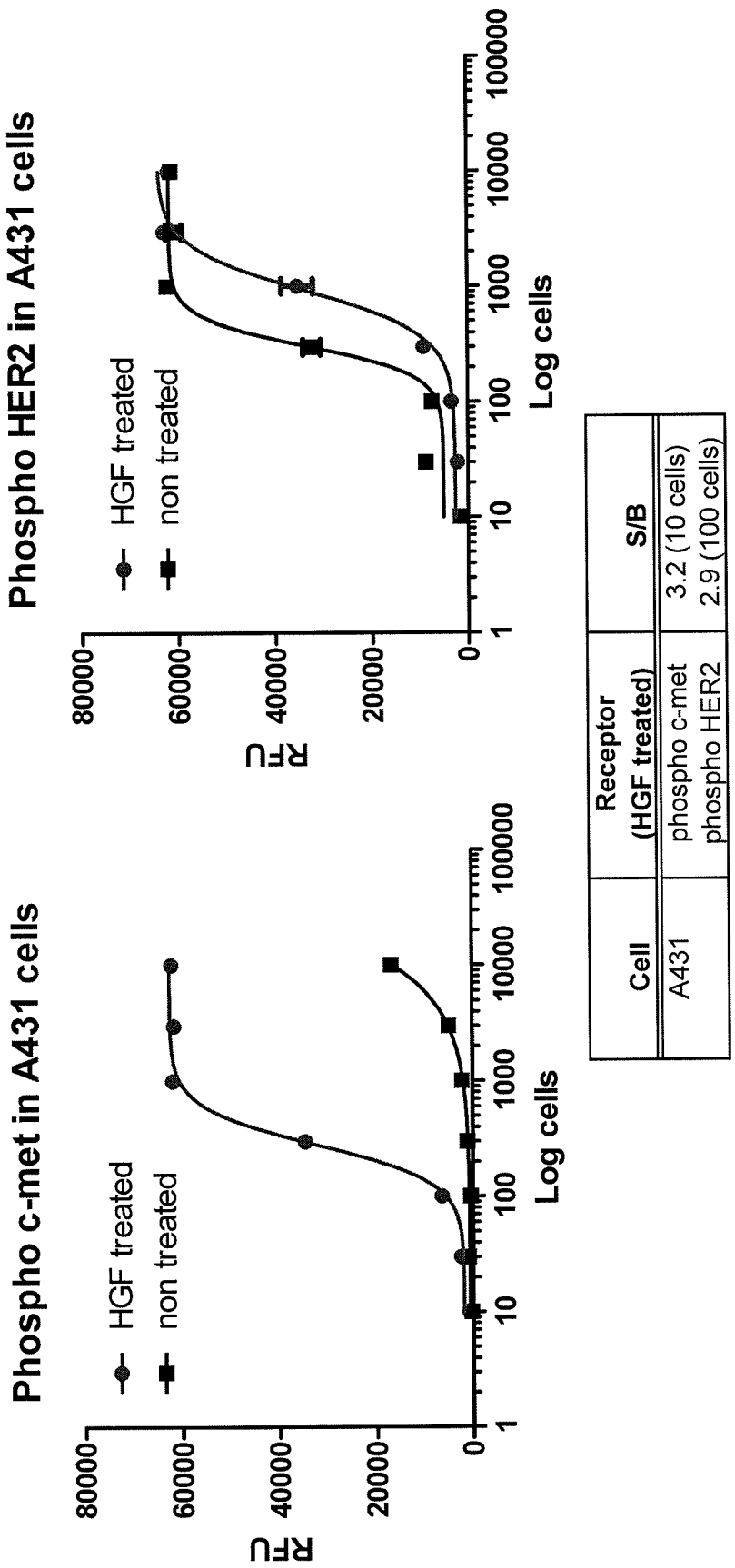
FIG. 3 shows the levels of c-Met and HER2 activation in HGF-treated A431 epidermoid carcinoma cells.

FIG. 3 shows that the c-Met ligand HGF stimulated c-Met phosphorylation, but not HER2 phosphorylation, in A431 epidermoid carcinoma cells. HER2 phosphorylation was slightly decreased with HGF treatment.

Figure 4:
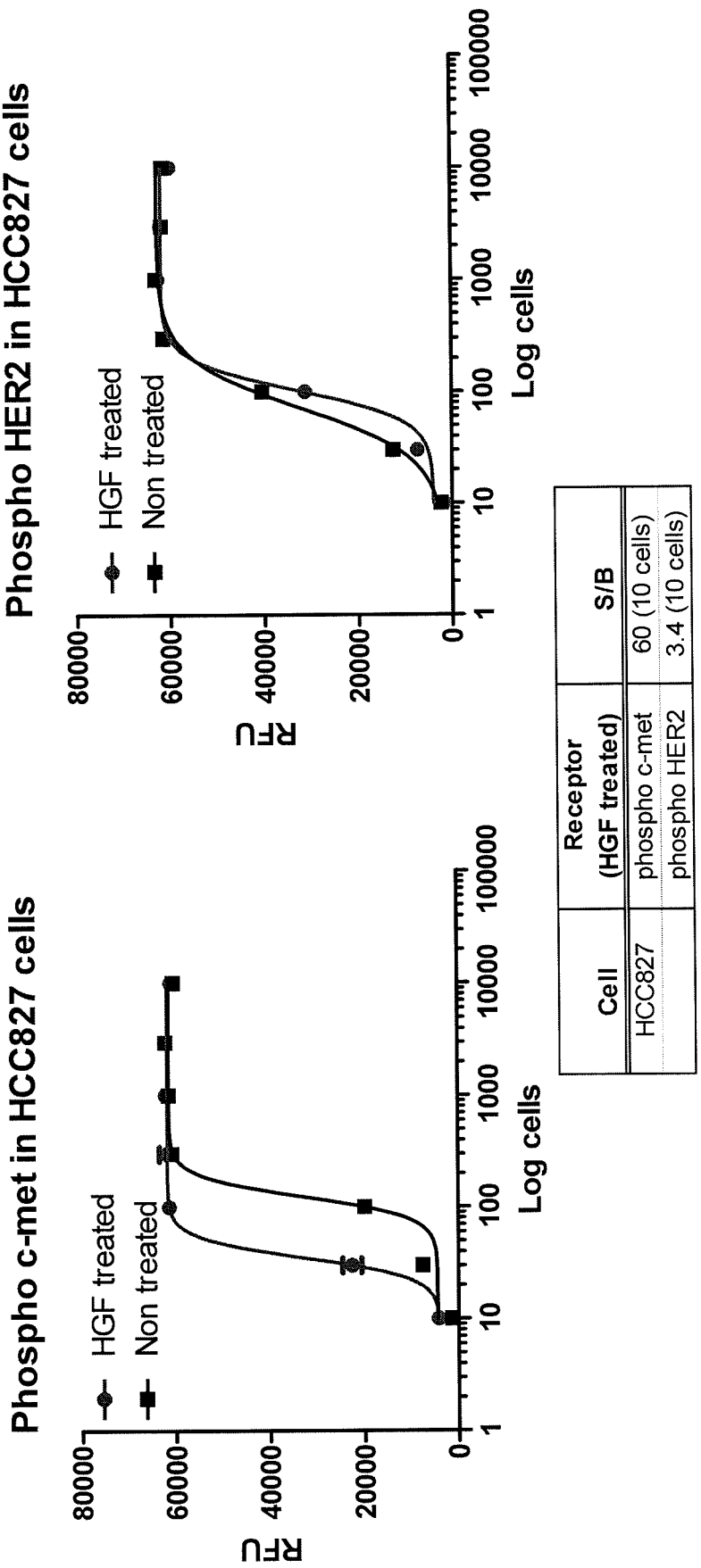
FIG. 4 shows the levels of c-Met and HER2 activation in HGF-treated HCC827 lung cancer cells.

FIG. 4 shows that c-Met was highly phosphorylated in HCC827 lung cancer cells. HGF treatment increased c-Met phosphorylation by about 4-fold in these HCC827cells. HER2 phosphorylation was not affected by HGF treatment.

Figure 5:
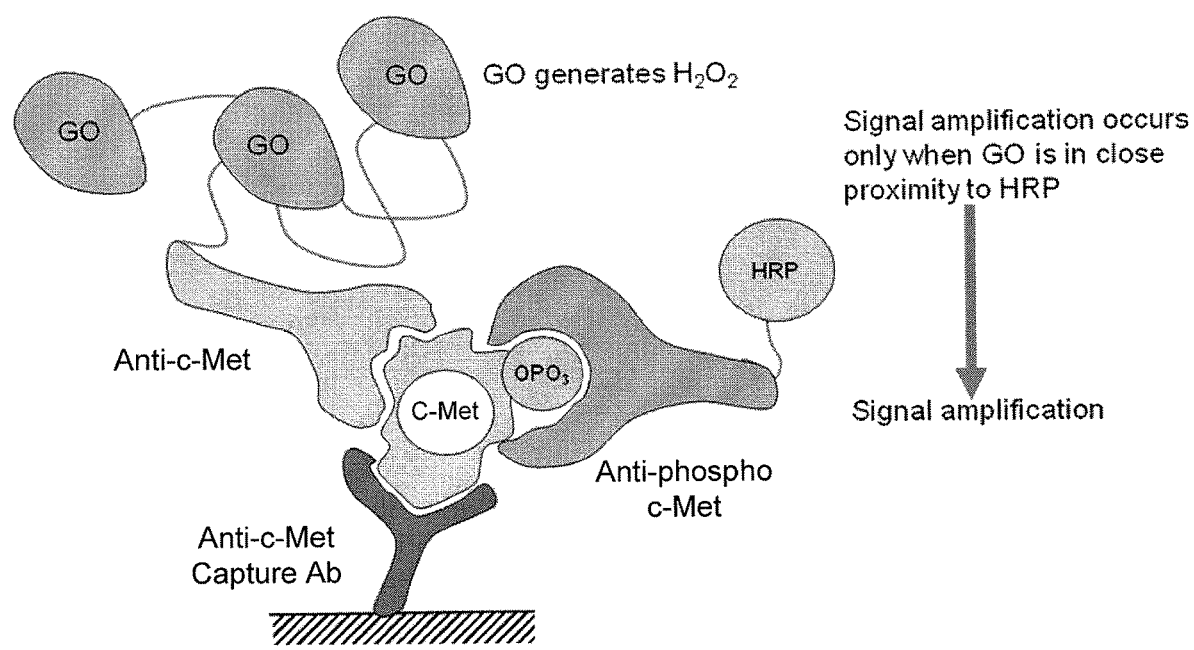
FIG. 5 shows one embodiment of the proximity assay format of the invention (COPIA), which relies on the co-localization of two additional detector antibodies linked with enzymes for subsequent channeling events per each target protein bound.

The multiplexed protein microarray platform described herein utilizes the formation of a unique immuno-complex requiring the co-localization of two detector enzyme-conjugated-antibodies once target proteins are captured on the microarray surface. The channeling events between two detector enzymes (glucose oxidase (GO) and horseradish peroxidase (HRP)) in proximity enables the profiling of a receptor tyrosine kinase (RTK) such as c-Met with extreme sensitivity. The analytical specificity is greatly enhanced given the requirement for simultaneous binding of three different antibodies. In particular, the multiplexed proximity assay is based on (1) a multiplexed protein microarray platform combined with (2) a triple-antibody-enzyme channeling signal amplification process. The unique and novel design is provided by the triple-antibody enzyme approach that confers ultra-high sensitivity while preserving specificity:

(1) The selected target is captured by target-specific antibodies printed in serial dilutions on a microarray surface. This format requires a co-localization of two additional detector-antibodies linked with enzymes for subsequent channeling events per each target'protein bound (FIG. 5).

(2) The immuno-complex formed by the initial target binding by capture antibodies and the secondary binding of GO (TON of $10^5$/min) conjugated antibodies that recognize an alternate epitope on the captured target molecules can produce $H_2O_2$ in the presence of the GO substrate, glucose.

(3) The target-specific local influx of $H_2O_2$ is then utilized by phospho-peptide-specific antibodies conjugated with HRP (TON of $10^4$/min) that bind to the phosphorylated peptide on the captured targets, hence amplifying target specific signals. Specificity for the detection of phosphorylated targets is greatly increased through the collaborative immuno-detection and amplification process given the requirement for simultaneous binding of three different types of antibodies. The detection and quantification of as few as ~$2$-$3\times10^4$ phosphorylation events is routinely achieved by this method, bringing its detection to a "single" cell level. In certain instances, this collaborative immunoassay configuration can be further applied to investigate protein interactions and activations.

Table 4 illustrates the percentage of patients with primary tumors having c-Met expression, mutation, or activation. Interestingly, patients with MET amplification in gastric cancer do not respond to c-Met inhibitors.

TABLE 4

| Tumor Type | MET Expression (% patients) | MET Mutation (% patients) | Met Amplification (% patients) |
| --- | --- | --- | --- |
| Brain | 54-88 | 0-9 | 9-20 |
| Head & Neck | 52-68 | 11-27 | n/a |
| Mesothelioma | 74-100 | 0 | n/a |
| Lung | 41-72 | 8-13 | 0 |
| Thyroid | 40-91 | 6-10 | n/a |
| Breast | 25-60 | 0 | n/a |
| Renal cell | 54-87 | 13-100 | Trisomy 7 |
| Hepatoma | 68 | 0-30 | n/a |
| Colon | 55-78 | 0 | 4-89 |
| Ovarian | 64 | 0-4 | 0 |
| Gastric | 75-90 | n/a | 10-20 |
| Melanoma | 17-30 | 0 | n/a | c-Met has been demonstrated to interact with and phosphorylate kinases such as RON, EGFR, HER2, HER3, PI3K, and SHC. c-Met may interact with other kinases as well, e.g., p95HER2, IGF-1R, c-KIT, and others. The multiplexed protein microarray described herein may be performed to interrogate the status of one or more of these kinases and their pathways using the limited number of cancer cells found in a patient's whole blood (e.g., circulating tumor cells) or FNA sample. The results of the assay enable the determination of the correct anticancer therapy for each individual patient.

FIG. 6 illustrates an exemplary addressable array of the invention for determining the expression and/or activation status of the following markers: c-MET, HER1/ErbB1, HER2/ErbB2, p95ErbB2, HER3/ErbB3, IGF-1R, RON, c-KIT, PI3K, SHC, VEGFR1, VEGFR2, and VEGFR3. Interrogation of these receptor tyrosine kinases and their pathways using the proximity assay microarray format advantageously enables the prediction of a patient's response to a particular c-Met inhibitor therapy. As a non-limiting example, patients who respond to XL-880 will have activated c-MET and VEGFR2, while non-responders will have a combination of RTKs activated. Importantly, the proximity assay microarray platform can also be used to select the appropriate combination therapy. For example, patients with activated c-MET, VEGFR2, and EGFR should be treated with a combination of Iressa +XL880, while patients with activated c-MET, VEGFR2, ErbB1, ErbB2, ErbB3, and p95ErbB2 should be treated with Tykerb+ XL880.

The multiplexed proximity-mediated platform advantageously provides single cell level sensitivity for detecting the activation of RTKs such as c-Met in a limited amount of sample. As such, circulating tumor cell (CTC) and/or mFNA samples obtained from patients with metastatic cancer can be profiled to provide valuable information for tailoring therapy and impacting clinical practice.

Example 7

Profiling Gastric Cancer Using Proximity Assays for Anticancer Drug Therapy Selection The expression/activation profiling of kinases and other signal transduction pathway molecules on a serial sampling of tumor tissues provides valuable information on changes occurring in tumor cells as a function of time and therapies. This temporal profiling of tumor progression enables clinicians to monitor rapidly evolving cancer signatures in each patient. This example illustrates a novel and robust assay to detect the level of expression and the degree of phosphorylation of receptor tyrosine kinase (RTK) pathways implicated in gastric cancer and demonstrates the advantages of using such a therapy-guiding diagnostic system with single cell level sensitivity. The assay generally relies on samples such as fine needle aspirates (FNAs) and blood and achieves high sensitivity and specificity for interrogating the limited amount of cancer cells obtained from such samples.

This example further aims to evaluate the incidence and clinical features of p95Her2(+) gastric cancer by: (1) surveying the frequency of p95Her2 in gastric cancer; (2) analyzing correlations between clinicopathologic variables and p95Her2 in gastric cancer; (3) correlating with preclinical data from Herceptin-resistant p95Her2(+) gastric cancer in vitro; and (4) implementing a clinical trial on lapatinib-based treatment in p95Her2(+) gastric cancer patients.

Gastric cancer is the leading cause of cancer death worldwide with the incidence of 18.9/100,000 per year. The incidence of gastric cancer was estimated to be 934,000 cases, with 56% of the new cases occurring in East Asia. Gastric cancer accounts for 20.8% of all cancers in Korea according to the Central Tumor Registry data for 2002. Although gastrectomy is the only curative treatment in gastric cancer patients, a high recurrence rate ranging from 40-60% following curative surgery still accounts for poor overall survival. One of the milestone studies in adjuvant trials was the U.S. Intergroup study, INT-0116, which reported a significantly better survival from chemoradiation therapy with 5-fluorouracil (5-FU)/leucovorin and $^{45}$Gy radiation mostly in D0-D1 nodal dissected gastric cancer patients. Moreover, a potential survival benefit from adjuvant chemoradiation therapy (INT-0116) was recently demonstrated in D2 dissected patients.

In order to further improve survival, there is an urgent need to identify reliable molecular prognostic markers for survival or recurrence following adjuvant chemoradiation therapy, which will evolve to the development of patient-tailored treatment strategies. Furthermore, improvement of gastric cancer therapy will eventually depend on novel therapeutic approaches.

RTKs are a family of 56 proteins characterized by a transmembrane domain and a tyrosine kinase motif. They function in cell signaling and transmit signals regulating growth, differentiation, adhesion, migration, and apoptosis. The mutational activation and/or overexpression of RTKs transforms cells and often plays a crucial role in the development of cancers. For such reasons, RTKs have become targets of various molecularly targeted agents such as trastuzumab, cetuximab, gefitinib, erlotinib, sunitinib, imatinib, nilotinib, etc. The median of relative gene expression levels of the 56 known RTKs in gastric cancer indicates that several RTKs, including EGFR, FGFR, and VEGFR subtypes, are present in gastric cancer.

Recently, an interim analysis of a ToGA clinical trial which compared capecitabine+cisplatin (XP) vs XP+trastuzumab in HER2(+) gastric cancer demonstrated a significant prolongation in progression free survival rate in the trastuzumab arm. Intriguingly, one of the mechanisms of trastuzumab resistance is the accumulation of truncated forms of the HER2 receptor, p95HER2, that lack the extracellular trastuzumab-binding domain. A recent study demonstrated that breast tumors that express p95HER2 are resistant to trastuzumab and may require alternative or additional anti-HER2 targeting strategies such as combination therapy with trastuzumab and lapatinib. Thus, it is important to establish the frequency of p95HER2 expression in order to lay the groundwork for future clinical trials incorporating HER2-targeted agents in gastric cancer.

The multiplexed protein microarray platform described herein can be used to interrogate the expression/activation of kinases and other signal transduction pathway molecules associated with gastric cancer. As such, methods for profiling gastric cancer markers in the limited number of cancer cells found in a patient's whole blood or fine needle aspirate (FNA) sample provide valuable insight into the overall disease pathogenesis, and therefore lead to better anticancer therapy selection.

Whole blood or FNA samples may be obtained from patients with gastric cancer for RTK pathway interrogation using the proximity assays described herein. Alternatively, samples for pathway analysis can be obtained from frozen tissues either by sectioning or performing a frozen FNA procedure. In certain instances, tissue sectioning is the preferred method for frozen specimens for subsequent profile analysis, while the relatively non-invasive FNA procedure is the preferred method for obtaining samples from patients (and xenografts) in a clinical environment.

Frozen tissue samples may be collected by the following methods:

Option #1. Tissue Section Collection:
1. Keep a plastic weighing boat on dry ice, in which sample cutting will take place.
   a. To chill the materials, keep razor blades or microtome blades, fine forceps, and pre-labeled sample collection vials on dry ice.
2. Take frozen human cancer tissues from −80° C. freezer and transfer samples immediately onto dry ice.
3. Place frozen tissue to weighting boat on dry ice, cut small pieces of frozen tissue (10 μm section×3) using razor blade or microtome blade, and transfer the tissue into pre-chilled and pre-labeled sample collection vial using pre-chilled forceps.
4. Close cap and keep it on dry ice.
5. Place collected specimens into a double plastic bag first and then into a Styrofoam container (primary container) with adequate amount of dry ice.
   a. Use at least 6-8 pounds dry ice. Use more in the summer months.

NOTE: Exact amount of dry ice will be determined after consulting with a shipping company.
b. Consult with shipping company for the international shipping process for necessary permits and documentations.
c. Do not use wet ice, or coolants (i.e., Cool Packs).
6. Make certain the requisition and sample list is placed in the box, but on the outside of the double bag.
7. Securely seal the container and label "Frozen Tissue—Do Not Thaw."

Option #2. FNA Prep from Frozen Tissues:
1. Take frozen human cancer tissues from −80° C. freezer and transfer sample vials immediately on dry ice.
2. Samples ready for FNA procedure should be placed on wet ice for 10 minutes to soften the tissue.
3. FNA sample collection should be performed by passing a 23 or 25 gauge needle through softened frozen tissue 5 to 10 times. Return remaining sample vial to dry ice.
4. Wipe the FNA sample collection vial lid with alcohol.
5. Frozen FNA tissues should be collected by direct injection into the collection vial containing 100 µl of "protein later solution" (Prometheus Laboratories; San Diego, Calif.). Dispense collected tissue materials by gently mixing the content.
6. Hold the FNA collection vial firmly with one hand and perform rapid finger tapping (~15×) to ensure through cell lysis (vortex for 10 seconds if possible).
7. Place collected specimens into a double plastic bag first and then into a Styrofoam container (primary container) with Cool Packs.
a. Consult with shipping company for the international shipping process for necessary permits and documentations.
8. Make certain the requisition and sample list is placed in the box, but on the outside of the double bag.
9. Securely seal the container and label with "Biological Specimen."

FIG. 7 illustrates an exemplary addressable array of the invention for profiling signal transduction pathways activated in gastric cancer based on the expression and/or activation status of the following markers: HER1/ErbB1, HER2/ErbB2, HER3/ErbB3, p95HER2/p95ErbB2, IGF-1R, c-MET, PI3K, SHC, Akt, and Erk. This activation profile can be compared to the results from the cohort of 500 gastric cancer specimens which are currently being profiled for several molecular targets (expression), including HER1, HER2, c-Met, PI3K, Akt, and FGFR2. Interrogation of these RTKs and their pathways using the proximity assay microarray format advantageously enables the prediction of a patient's response to a particular therapeutic regimen for the treatment of gastric cancer. In addition, the RTK expression/activation profile based on the proximity assay microarray technology can assist clinical trials based on RTK-targeted therapeutics. Currently, lapatinib is under clinical investigation in a LOGiC trial, where its addition to the chemotherapy regimen of capecitabine+oxaliplatin (CapeOx) is being evaluated for its impact in extending the time to progression and overall survival of patients with locally advanced, unresectable, or metastatic gastric, esophageal, or gastroesophageal junction cancer with amplification of the ErbB2 gene. As such, profiling each disease for activated p95ErbB2, HER2, and HER1 in addition to HER2 expression provides clinically relevant information for selecting the right patients for HER2-targeted therapy.

Figure 24:
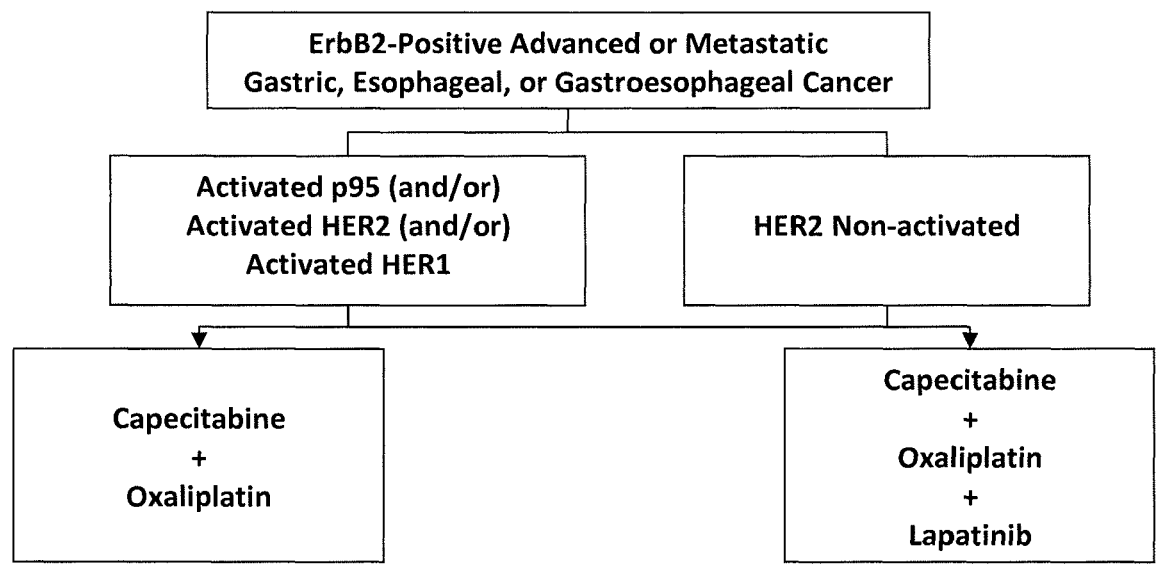
FIG. 24 shows that patients with ErbB2-positive advanced or metastatic gastric, esophageal, or gastroesophageal cancer having activated p95ErbB2 and/or activated HER2 and/or activated HER1 as determined by the proximity assay described herein should be treated with a combination of capecitabine and oxaliplatin, while those patients having non-activated HER2 should be treated with a combination of capecitabine, oxaliplatin, and lapatinib.

As a non-limiting example, FIG. 24 shows that patients with ErbB2-positive advanced or metastatic gastric, esophageal, or gastroesophageal cancer having activated p95ErbB2 and/or activated HER2 and/or activated HER1 as determined by the proximity assay described herein should be treated with a combination of capecitabine and oxaliplatin, while those patients having non-activated HER2 should be treated with a combination of capecitabine, oxaliplatin, and lapatinib.

The multiplexed proximity-mediated platform advantageously provides single cell level sensitivity for detecting the activation of RTKs and their pathways in a limited amount of sample. As such, CTC and/or mFNA samples obtained from patients with gastric cancer can be profiled to provide valuable information for tailoring therapy and impacting clinical practice.

Example 8

Selection of Patients for Treatment After Determination of Primary Tissue of Origin by a Gene Expression Panel Approximately 3% to 5% of all metastatic tumors are classified into the category of cancer of unknown primary (CUP). Correct diagnosis of the tissue of origin is important in treatment decisions because current therapies are based largely on anatomical site. Gene expression panels can be useful in identifying patients with metastatic gastric cancer who would benefit from therapy consistent with that given to patients diagnosed initially with gastric cancer. Suitable systems include, but are not limited to, the Rosetta Genomics CUP assay, which classifies cancers and tissues of origin through the analysis of the expression patterns of microRNAs (see, e.g., PCT Publication No. WO 08/117,278); the Aviara DX (Carlsbad, Calif.) CancerTYPE ID™ assay, an RT-PCR-based expression assay that measures 92 genes to identify the primary site of origin for 39 tumor types; and the Pathwork™ Tissue of Origin Test (Sunnyvale, Calif.), which measures the expression of more than 1600 genes on a microarray and compares a tumor's gene expression "signature" against those of 15 known tissue types. Once the patient has been identified with the esophagus and/or stomach as the tissue of primary cancer, pathway activation profiles can be used to select the appropriate targeted therapies to include in the treatment schedule.

The following protocol provides an exemplary embodiment of the present invention wherein gene expression profiling is used in conjunction with activation state profiling to select the appropriate targeted therapy or combination of targeted therapies for the treatment of gastric, esophageal, or gastroesophageal cancer:

1) Two or more glass slides with 7 µm thick sections of a tissue removed, either surgically or by fine needle biopsy, from a metastatic tumor are obtained from the patient. These cells are fixed in formalin and embedded in paraffin (FFPE). One additional slide of the same tumor is stained with H&E.
2) A pathologist reviews the H&E slide and indicates the area to be collected for the CancerTYPE ID™ assay. The slides are sent to Aviara DX for analysis.
3) The test report from Aviara DX indicates the top 5 most probable sites of origin as determined from a k-nearest neighbor analysis and a prediction is derived. If the prediction for the patient is for esophagus and/or stomach as the tumor of unknown origin, the patient's tumor cells can be assessed for pathway activation.
4) Tumor cells (e.g., CTCs) are isolated from blood and prepared for analysis as described in Example 1. Alternatively, a fine needle biopsy can be used to prepare a tumor cell extract as described in Example 2. The cell preparations are assayed as described in either Example 3 or Example 4. The activation profile is evaluated in a similar manner as described in Example 6 or Example 7. The appropriate targeted therapy or combination of targeted therapies is selected.

Example 9

Functional Profiling of Signal Transduction Pathway Proteins in Gastric Cancer Patients Although gastrectomy is the only curative treatment in gastric cancer (GCA) patients, a high recurrence rate ranging from 40~60% following curative surgery still accounts for poor overall survival. In order to further improve survival, there is an urgent need to identify reliable molecular prognostic markers for survival or recurrence following adjuvant chemoradiation therapy, which will evolve to the development of patient-tailored treatment strategies. The improvement of gastric cancer therapy will eventually depend on novel therapeutic approaches targeting molecules critical for cancer proliferation. As the transduction pathway proteins function in cell signaling and transmit signals regulating growth, differentiation, adhesion, migration, and apoptosis, they have become targets of various therapeutic agents. The multiplexed immunoassay platform described herein can be utilized for the functional profiling of these transduction pathway proteins.

The COllaborative Proximity ImmunoAssay (COPIA) is a multiplexed protein microarray platform that utilizes the formation of a unique immuno-complex requiring co-localization of two detector-antibodies. The detector-antibodies are conjugated with corresponding channeling-enzymes, glucose oxidase (GO) and horseradish peroxidase (HRP). Once target proteins are bound by the capture antibodies, the channeling events between GO and HRP in proximity enables the profiling of the target proteins with extreme sensitivity. COPIA delivers extremely high analytical specificity as it requires multiple entities within target specific proximity for the signal generation/amplification. COPIA can also be configured for each specific target protein to allow differential detection of truncated targets (i.e., p95HER2) from their normal counter parts (i.e., HER2). COPIA was applied to investigate the levels of expression and activation of signaling proteins in frozen tissues collected from GCA patients.

This example demonstrates the prevalence of HER1, HER2, p95HER2, HER3, IGF1-R, c-MET, PI3K, Shc, VEGFR, panCK, and other signal transduction pathway protein expression and their levels of activation in GCA patients. The improvement of gastric cancer therapy will eventually depend on novel therapeutic approaches targeting specific markers identified by functional profiling. As the disease profile often shifts in recurrent cancers and under different therapeutic pressure, clinical information obtained by analyzing samples (often with limited availability) obtained from 'evolving/heterogeneous disease' can help clinicians adjust their disease treatment options for each patient according to 'personal' cancer profile-shift.

Example 10

Functional Profiling of Multiple Signal Pathway Proteins in Gastric Cancer Patients Abstract
Although gastrectomy is the only curative treatment in gastric cancer (GCA) patients, a high recurrence rate ranging from 40~60% following curative surgery still accounts for poor overall survival. In order to further improve survival, there is an urgent need to identify reliable molecular prognostic markers for survival or recurrence following adjuvant chemoradiation therapy, which will evolve to the development of patient-tailored treatment strategies. Hence, we have developed a multiplexed immunoassay platform for functional profiling of the signal transduction pathway proteins using a multiplexed immuno-microarray platform. This example demonstrates the functional profiling of HER2, HER1, HER3, PI3K, cMET, and IGF1R in GCA.

Introduction
Gastric cancer is the leading cause of cancer death worldwide with an incidence of 18.9/100,000 per year and a mortality rate of 14.7/100,000 per year. Metastatic gastric cancer remains a therapeutic challenge for medical oncologists due to poor prognosis. In quest of a novel therapeutic target for gastric cancer, HER2 over-expression has been tested and was reported in 6-35% of stomach and gastroesophageal tumors. Trastuzumab, a humanized monoclonal antibody which selectively targets HER2, has shown survival benefit in patients with HER2(+) metastatic breast cancer. Of note, 70-80% of patients HER2 over-expressing breast cancer do not respond to trastuzumab due to either primary or acquired resistance. One of the important mechanisms for trastuzumab resistance is the accumulation of truncated forms of the HER2 (p95-HER2) which lack the extracellular trastuzumab-binding domain. Herein, we report the expression/activation-profiling of HER2, p95-HER2, and other pathway proteins with transactivational potential for HER2 activation in order to lay groundwork for future clinical trials incorporating HER2 targeted agents in gastric cancer.

Figure 8:
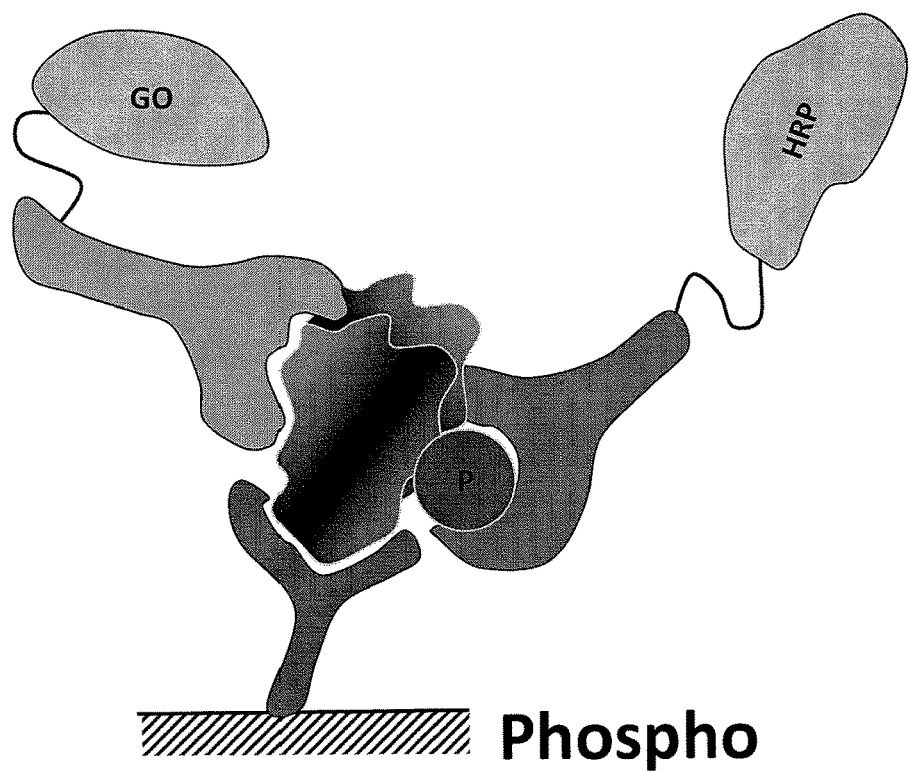
FIG. 8 shows another embodiment of the proximity assay format of the invention (COPIA), which is particularly useful in determining activated (e.g., phosphorylated) and total analyte levels in a biological sample.
Figure 8:
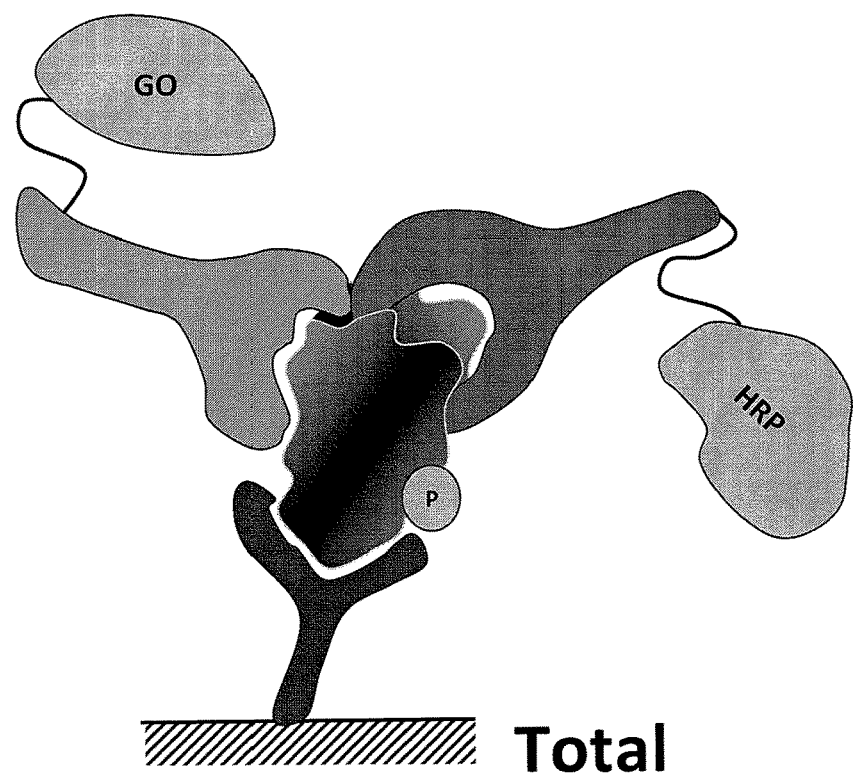

Methods
COllaborative Proximity ImmunoAssay (COPIA): Target proteins present in tissue lysates are bound to specific capture antibodies printed on nitrocellulose surface and unbound non-target proteins are removed from the slide. The enzymatic interaction between one detector antibody against an alternate epitope on a captured target protein conjugated to Glucose Oxidase (GO) and the other detector antibody specific for a phosphorylated site on the target protein or another non-overlapping epitope conjugated to HRP results in signal generation and subsequent tyramide-mediated signal amplification (FIG. 8).

Slide Printing: Capture antibodies for each specific target protein are printed in triplicates in serial dilution. Each slide contains cell line controls for standard curve generation for accurate quantitation of samples on each slide run. Internal quality control samples are run on each slide to ensure the quality of data generated from each array-slide.

Clinical Samples: The flash frozen breast cancer tissues were from patients with localized, histologically confirmed GCA (Samsung Medical Center). The flash frozen tissue samples were lysed in 100 µL of lysis buffer, and the resulting lysates were stored at −80° C. before subsequent analysis.

p95HER2Enrichment: The full-length HER2 receptors were removed from the cell lysate using magnetically labeled antibodies specific to the extracellular domain (ECD) of HER2.

Figure 9:
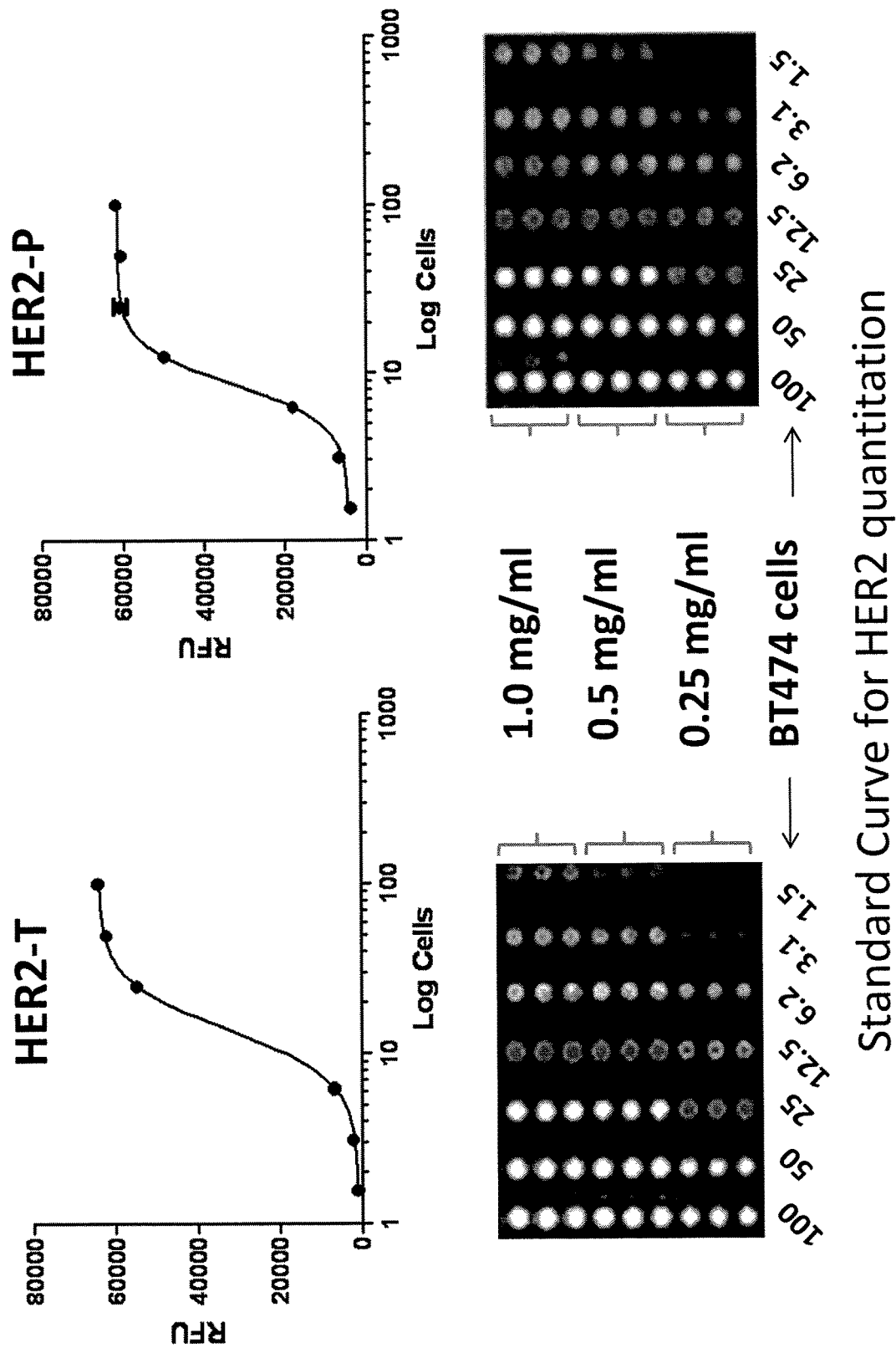
FIG. 9 shows standard titration curves generated for HER2 quantitation.
Figure 10B:
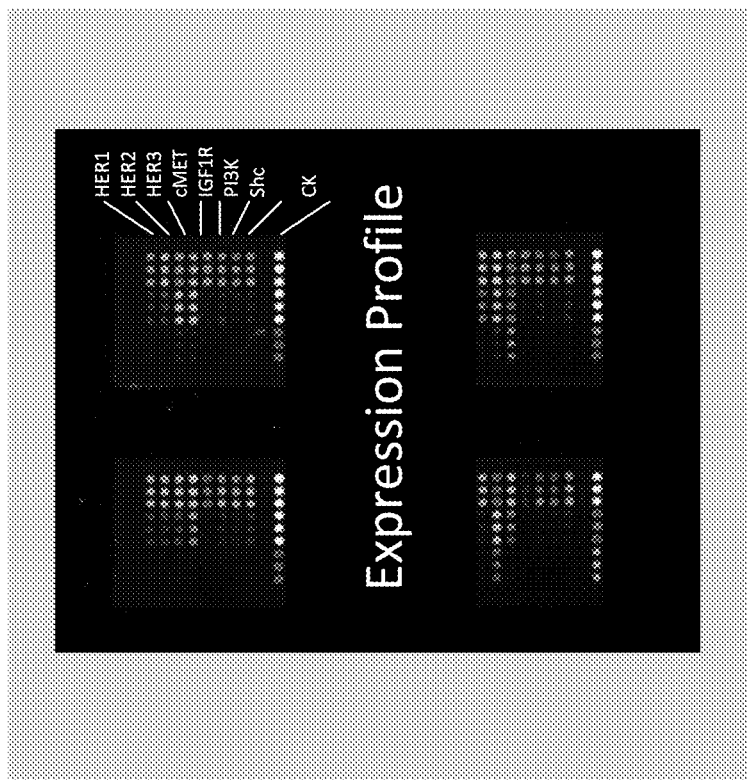
FIG. 10B shows the quantitation of target protein expression and phosphorylation based on cell lines with known levels of RTK expression treated with ligands specific for each RTK.
Figure 10A:
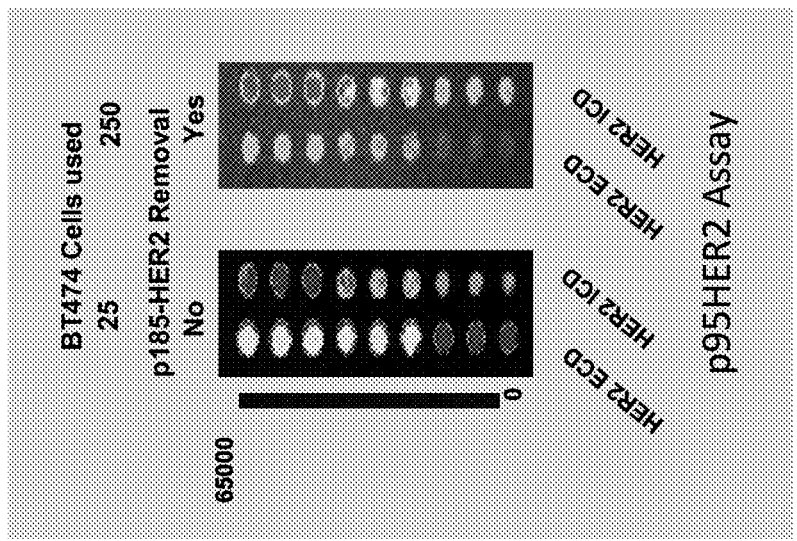
FIG. 10A shows a comparison of the differential HER2 profiling (with HER2-ECD and HER2-ICD captures) of BT474 cells with and without the removal of the full-length HER2.

Results
The HER2 standard titration curves were generated using BT474 cells, and single cell level sensitivity was achieved as shown in FIG. 9. These values are used as a standard to generate quantitative values for clinical samples. The comparison of the differential HER2 profiling (with HER2-ECD and HER2-ICD captures) of BT474 cells with and without the removal of the full-length HER2 showed that there was approximately 4.4% p95HER2 in the HER2-amplified reference cell line BT474 (FIG. 10A). The quantitation of target protein expression and phosphorylation was based on cell lines with known levels of RTK expression (e.g., BT474, T47D, HCC827) treated with ligands specific for each RTK (FIG. 10B).

Figure 11:
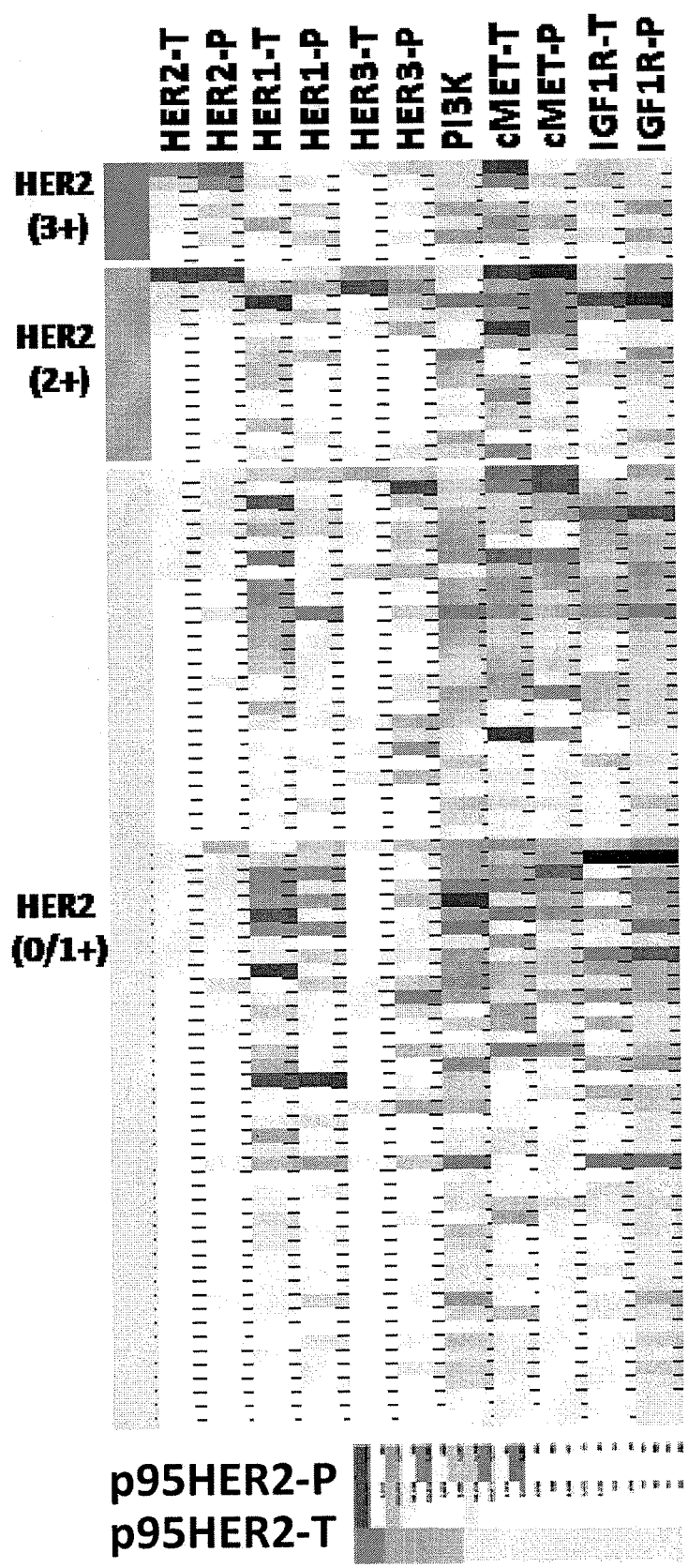
FIG. 11 shows that a wide range of pathway protein expression in GCA samples was observed. "T"=Total; "P"=phosphorylated.

A wide range of pathway protein expression in GCA samples was observed as shown on in FIG. 11. The sample with the highest signal for each marker is indicated with the darkest color. The COPIA-HER2 showed high correlation with IHC-HER2 status. Higher levels of HER1 were found in samples with lower HER2 expression. The HER3-P level showed high degree of correlation with HER3-T and PI3K activation. The cMET profile also showed strong correlation with PI3K activation. The expression of IGF1R in this cohort was relatively lower in most samples. The p95HER2 levels were prominent in samples with higher HER2 expression; however, evidence of p95HER2 activation had a wider distribution. Table 5 summarizes the RTK expression in 95 GCA samples.

TABLE 5

|   | HER2 | HER1 | HER3 | cMET | IGF1R |
|---|------|------|------|------|-------|
| H | 13 (14%) | 13 (14%) | 24 (25%) | 5 (5%) | 0 |
| M | 67 (70%) | 64 (67%) | 45 (47%) | 51 (54%) | 0 |
| L | 15 (16%) | 18 (19%) | 26 (28%) | 39 (41%) | 95 (100) |

"H" = High; "M" = Medium; "L" = Low.

Conclusion

The findings described in this example on the status of HER2 and its variant forms as well as other RTKs provide critical information on the potential mechanisms for HER2-positive GCA patients who do not respond to trastuzumab due to either primary or acquired resistance. The COPIA format and analysis of the present invention can be advantageously utilized to profile GCA patients for their signal transduction proteins for selecting effective targeted therapy.

Example 11

Functional Profiling of Signal Transduction Pathway Proteins in CTCs Isolated from Gastric Cancer Patients This example demonstrates the functional profiling of signal transduction pathway proteins such as HER1 and HER2 in circulating tumor cells (CTCs) obtained from the blood of gastric cancer (GCA) patients using the COllaborative Proximity ImmunoAssay (COPIA) multiplexed protein microarray platform described herein. As such, one particular objective of the experiments set forth in this example was to survey the frequency of HER2-positive CTCs in GCA.

Patients and testing samples: Stage III or IV gastric cancer patients (N=100) were enrolled in the study and single blood sample collection was performed. In some instances, an ascites sample was obtained.

Outcome Measures: HER1 and HER2 expression and activation in CTCs isolated from blood samples of GCA patients.

Enrollment and Status:

| Sample type | No. expected | Enrollment |
|-------------|--------------|------------|
| Blood       | 100          | 83 (80)    |
| Ascites     | not defined  | 3          |

3 GCA patients had an insufficient blood volume for COPIA analysis.

Figure 12:
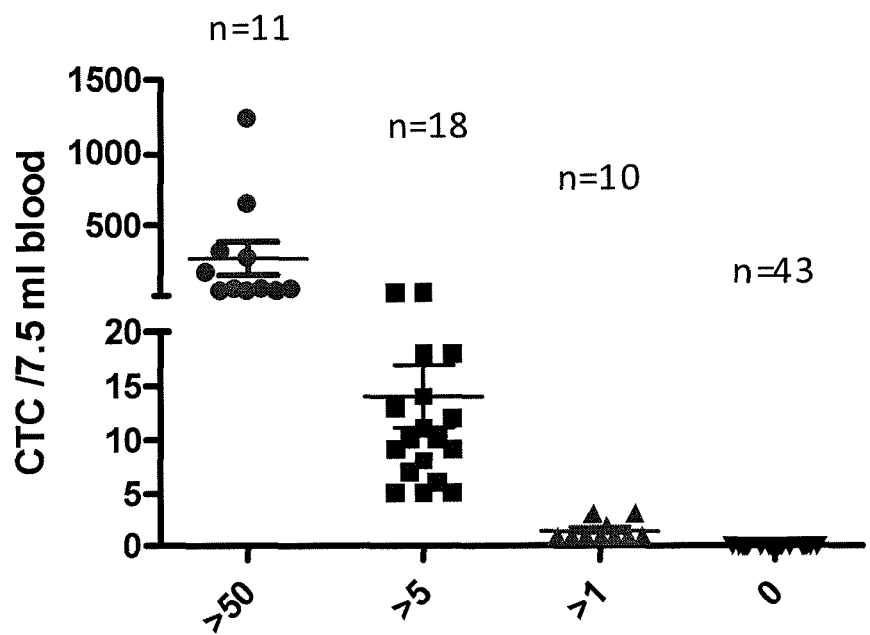
FIG. 12 shows the number of CTCs obtained in a specific volume of blood from GCA patients as determined by the Veridex CTC enumeration system.

FIG. 12 shows the number of CTCs obtained from 7.5 mls of blood in 82 GCA patient samples as determined by the Veridex CTC enumeration system. In particular, 39 out of 82 (48%) of the GCA blood samples were CTC-positive, while 12 out of 82 (14.6%) of the GCA blood samples were HER2-positive.

Figure 13:
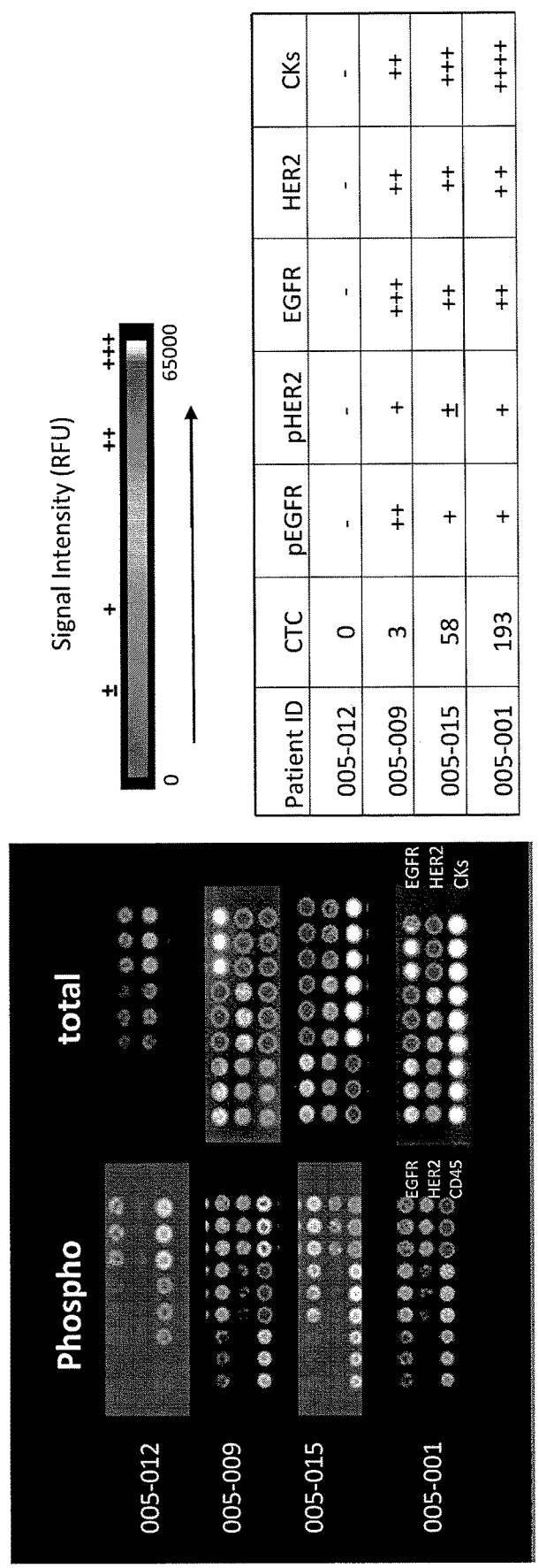
FIG. 13 shows the expression and activation of HER1/EGFR and HER2 in CTCs isolated from GCA patients as determined by COPIA.

FIG. 13 shows the expression and activation of HER1/EGFR and HER2 in CTCs isolated from GCA patients as determined by COPIA. Samples with CTCs as identified by the Veridex system displayed prominent HER1 and HER2 expression, with lower levels of HER1 and HER2 activation (i.e., phosphorylation).

The COPIA format and analysis of the present invention can be advantageously utilized to profile GCA patients for their signal transduction proteins for selecting effective targeted therapy. For example, determination of the expression and activation of HER1 and HER2 in GCA patients provides insight into whether therapy targeting to one or both of these RTKs would be effective.

Example 12

Functional Profiling of Signal Transduction Pathway Proteins in Tumor Tissue Isolated from Gastric Cancer Patients This example demonstrates the functional profiling of signal transduction pathway proteins such as HER1, HER2, HER3, c-Met, IGF1R, cKit, PI3K, and Shc in gastric cancer (GCA) tumor tissue samples using the COllaborative Proximity ImmunoAssay (COPIA) multiplexed protein microarray platform described herein. This example also demonstrates the functional profiling of p95HER2 in GCA tumor tissue samples using COPIA. As such, particular objectives of the experiments set forth in this example were (1) to survey the frequency of p95HER2 in GCA tumor tissue, (2) to analyze the correlation between clinicopathologic variables and p95HER2, and (3) to correlate with preclinical data from trastuzumab-resistant p95HER2(+) gastric cancer in vitro.

Patients and testing samples: 447 frozen GCA tumor tissue specimens obtained from surgical resection were used in this study.

Outcome Measures: Expression and activation of signal transduction pathway proteins including p95HER2 in GCA.

Enrollment: 447 frozen GCA tissue samples were collected and 10 markers tested.

Figure 14:
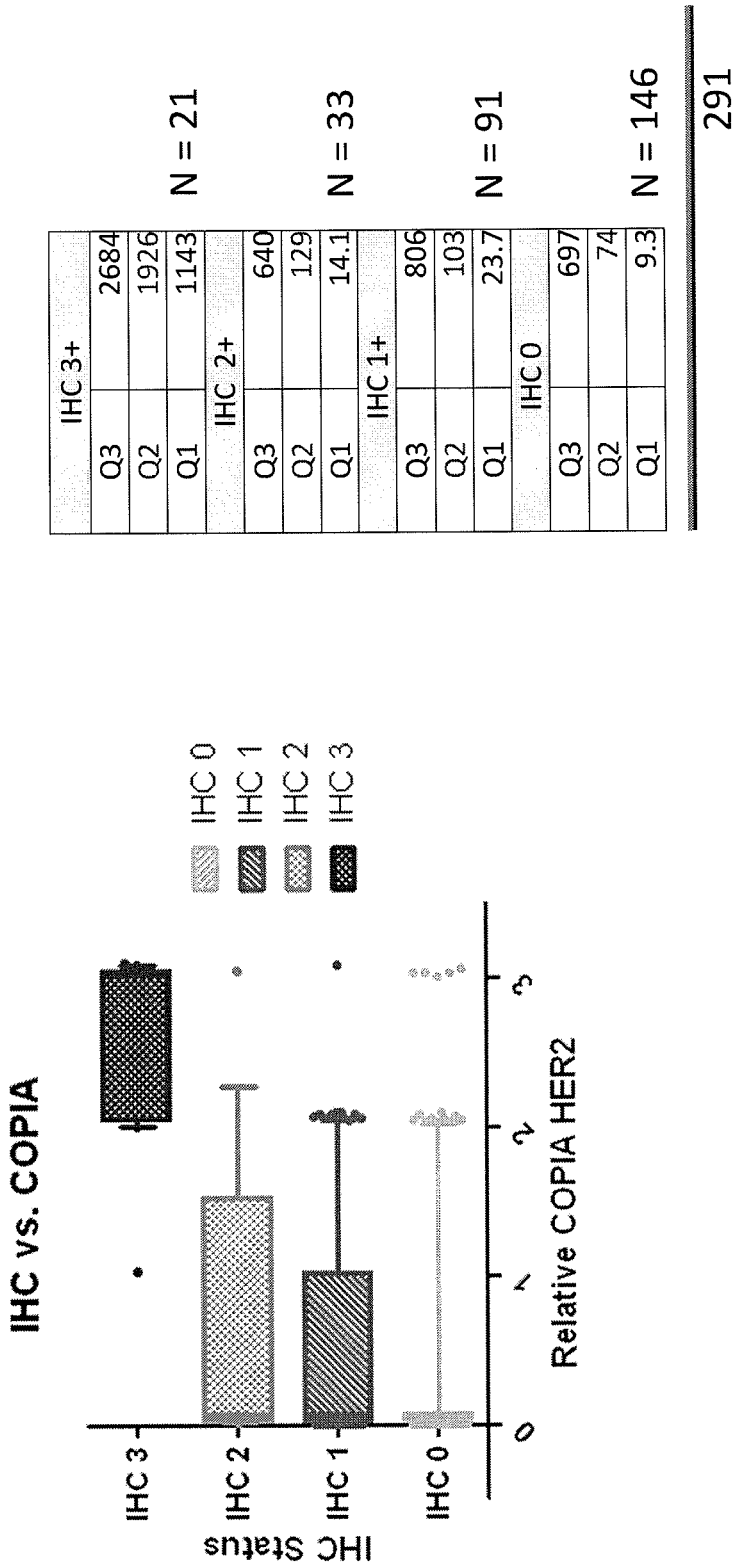
FIG. 14 shows the degree of correlation between immunohistochemistry (IHC) and COPIA for detecting HER2 expression in GCA tumor tissue.

FIG. 14 shows the degree of correlation between immunohistochemistry (IHC) and COPIA for detecting HER2 expression in GCA tumor tissue. In particular, FIG. 14 shows that there was a high degree of correlation between IHC and COPIA in the "IHC 3" category, which corresponds to GCA tissue samples having the highest level of HER2 expression as determined by IHC. However, a significant number of GCA tissue samples identified as "IHC 0" (which corresponds to no detectable HER2 expression by IHC) actually had moderate to high levels of HER2 expression as determined by COPIA. As such, FIG. 14 illustrates the dramatically increased sensitivity achieved using COPIA when compared to standard IHC anaylsis of HER2 expression.

Figure 15:
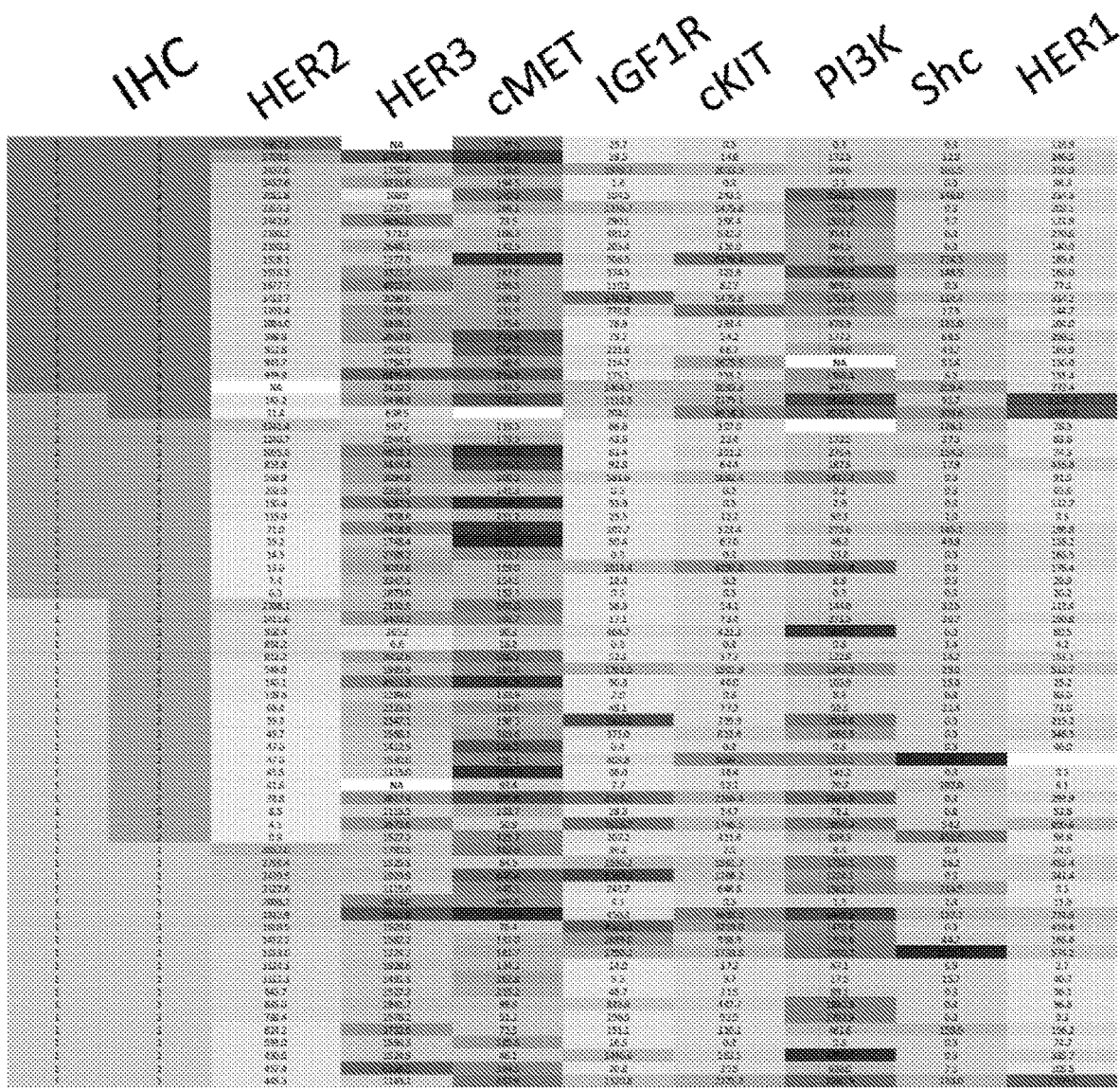
FIG. 15 shows that a wide range of pathway protein expression in GCA samples was observed. The analytes assayed by COPIA included the following signal transduction pathway proteins: HER1, HER2, HER3, c-Met, IGF1R, cKit, PI3K, and Shc. N=291.
Figure 15:
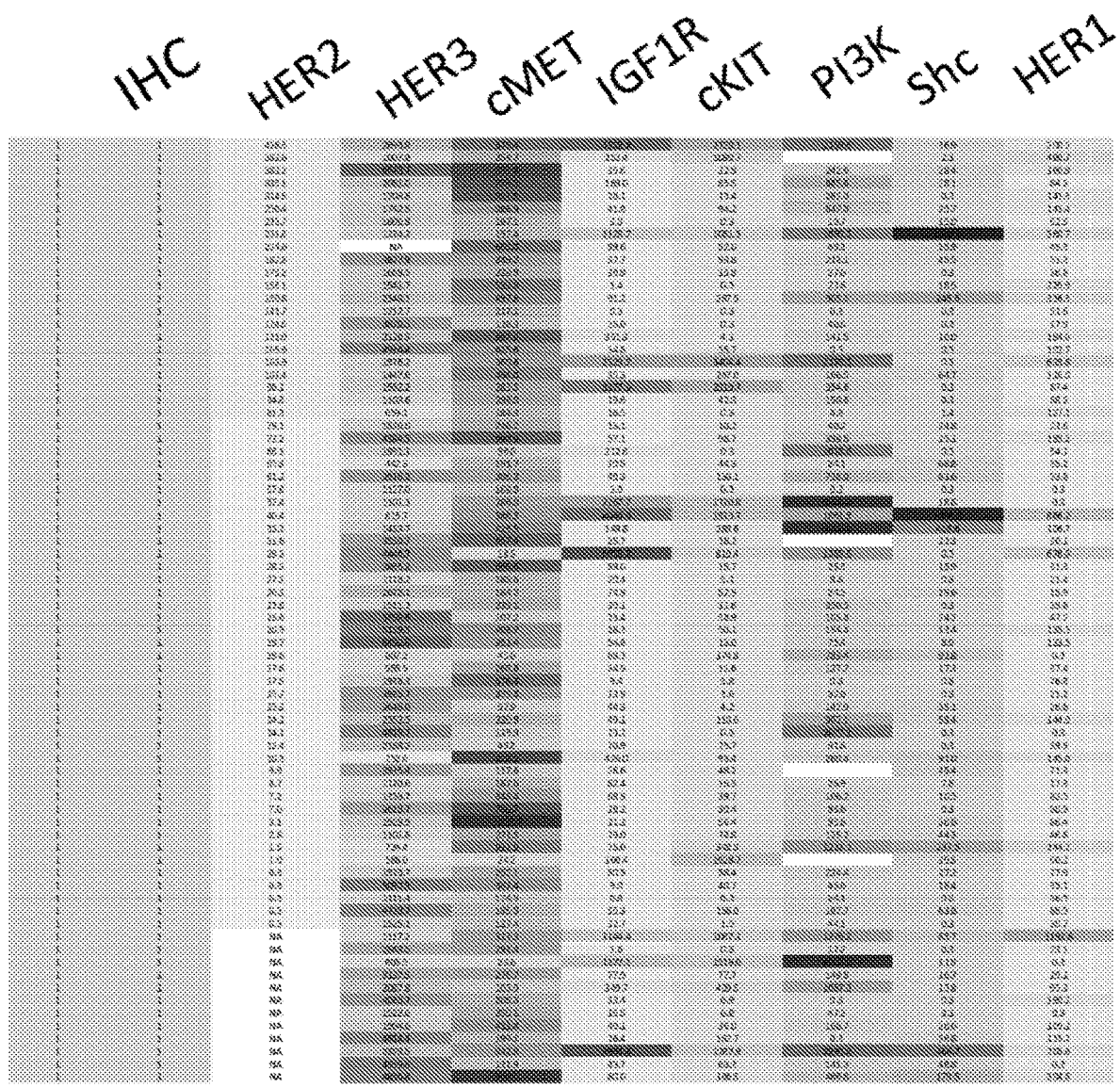
Figure 15:
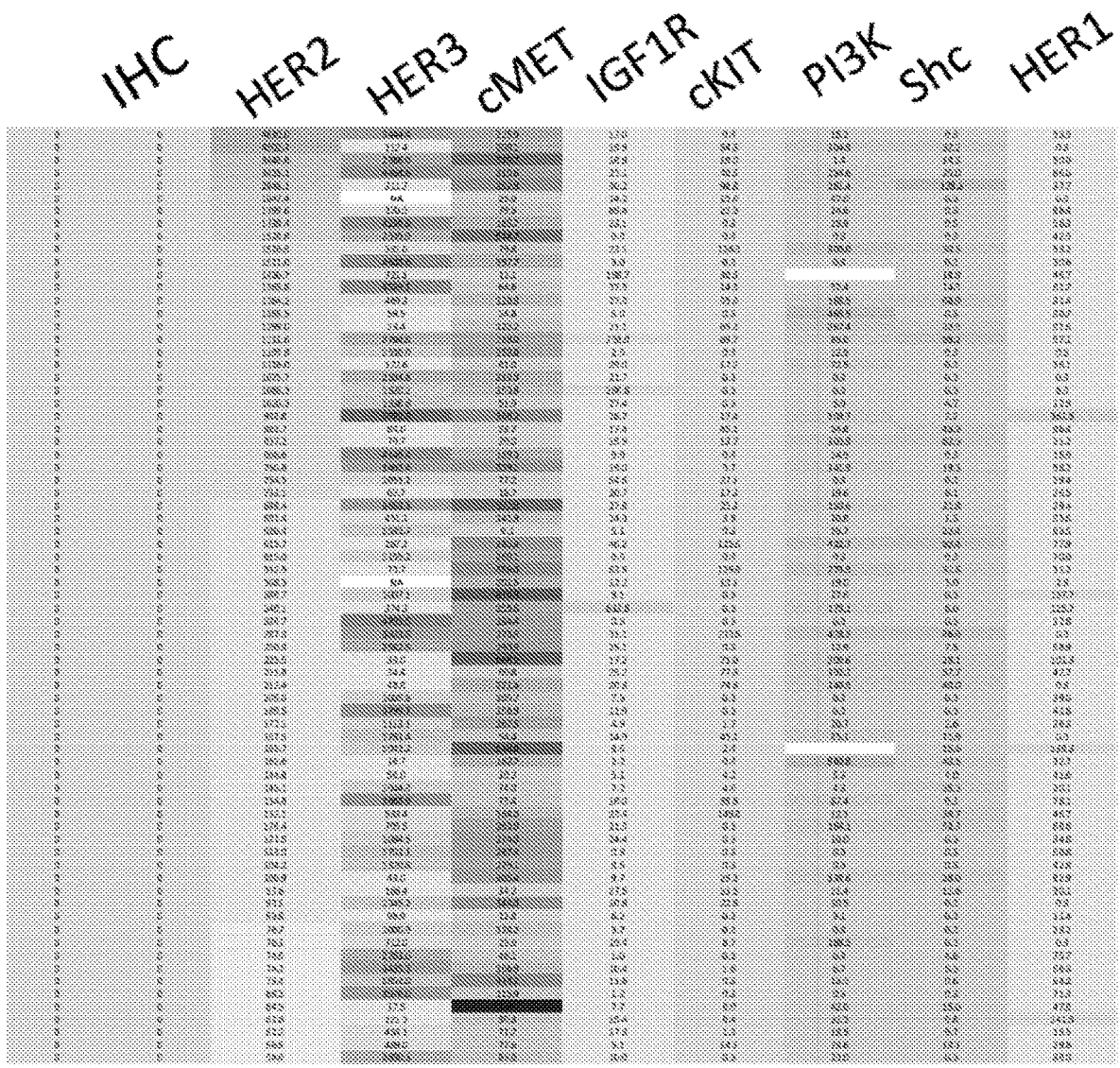
Figure 15:
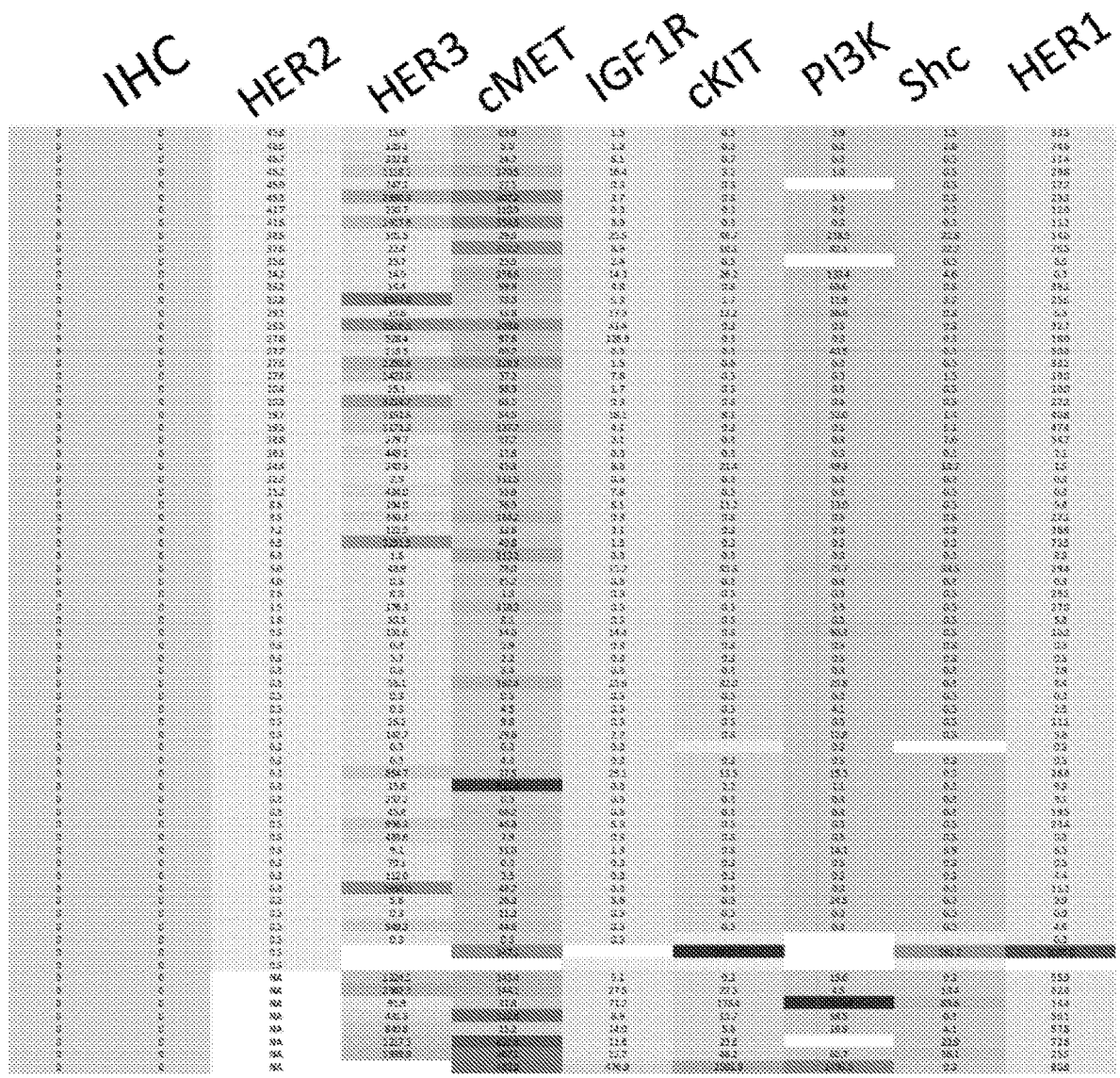

A wide range of pathway protein expression in GCA samples was observed as shown on in FIG. 15. The sample with the highest signal for each marker is indicated with the darkest color. The analytes assayed by COPIA included the following signal transduction pathway proteins: HER1, HER2, HER3, c-Met, IGF1R, cKit, PI3K, and Shc. These analytes can be analyzed for both expression levels and activation (e.g., phosphorylation) levels using COPIA. In certain embodiments, the expression and/or activation (e.g., phosphorylation) levels of at least one, two, three, four, five, or more additional analytes including, but not limited to, p95HER2, Akt, p70S6K, VEGFR, and/or PDGFR can be analyzed in GCA tissue samples using COPIA.

Figure 16:
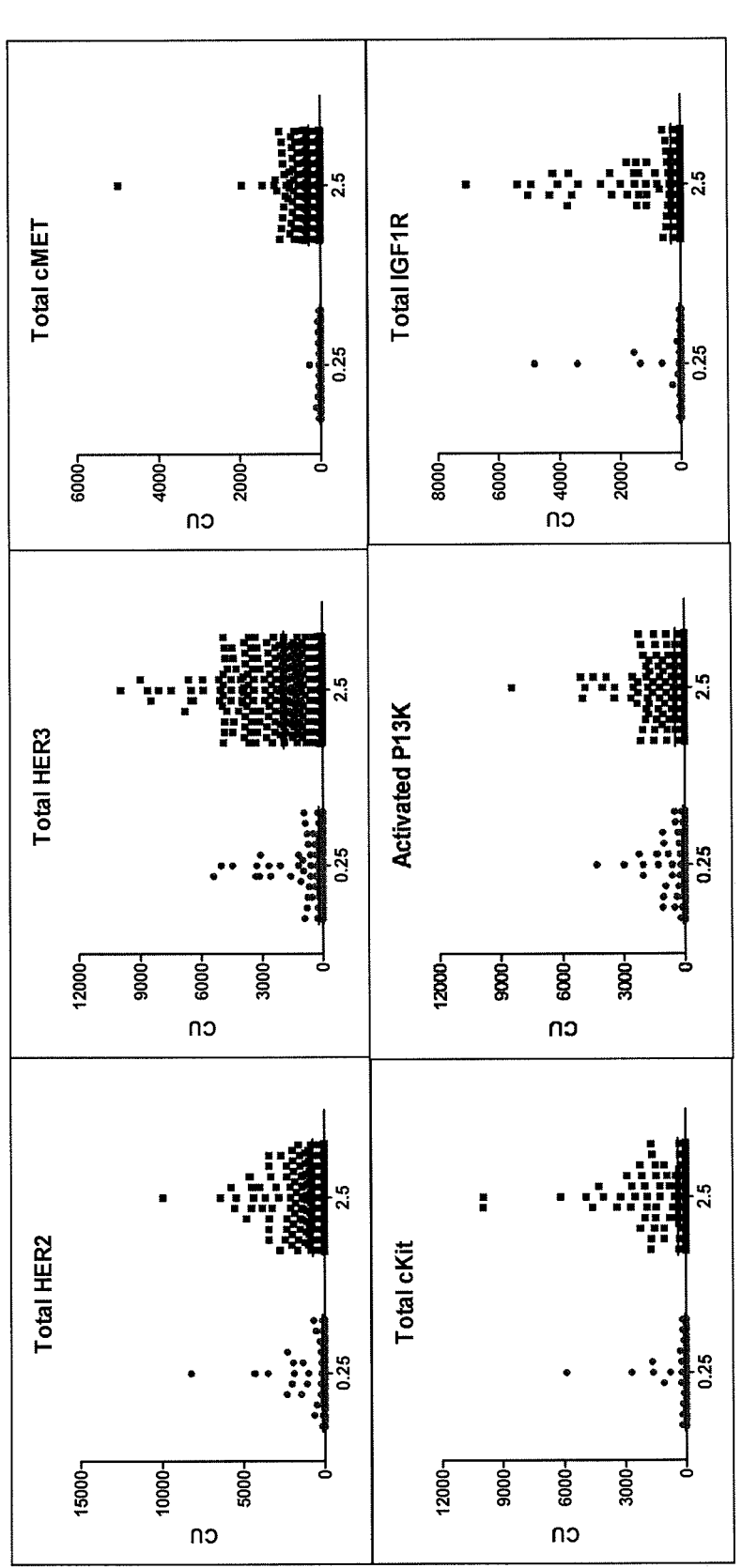
FIG. 16 shows COPIA analyses of the expression levels of HER2, HER3, c-Met, IGF1R, and cKit and the activation levels of PI3K in GCA tumor tissue at two different tumor lysate concentrations.

FIG. 16 shows COPIA analyses of the expression levels of HER2, HER3, c-Met, IGF1R, and cKit and the activation levels of PI3K in GCA tumor tissue at two different tumor lysate concentrations. In particular, COPIA was capable of detecting the expression or activation levels of each interrogated analyte at both tumor lysate concentrations.

Figure 17:
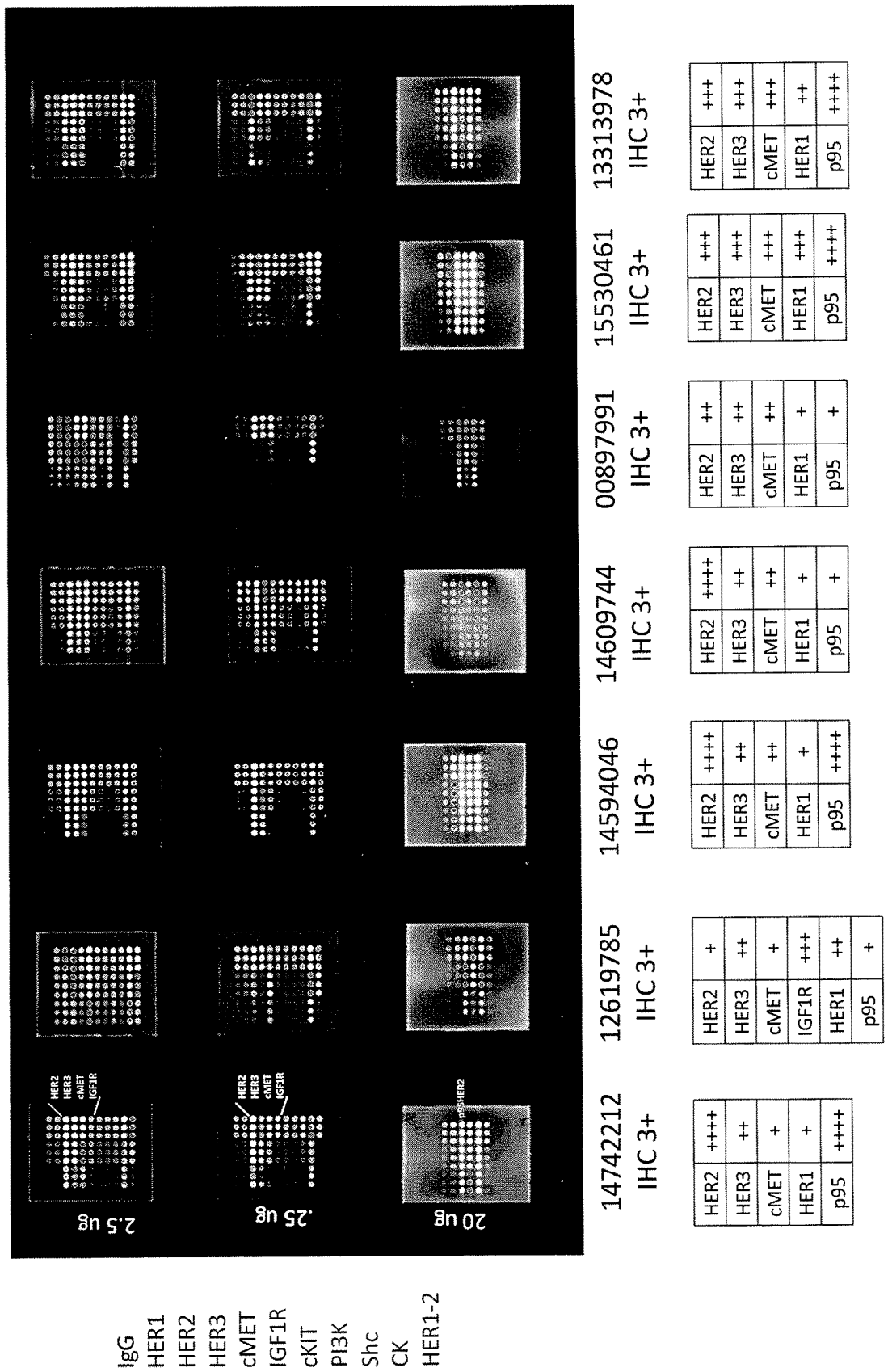
FIG. 17 shows the expression profiling of HER1, HER2, HER3, c-Met, IGF1R, cKit, PI3K, and Shc in GCA tumor tissue samples using COPIA. IgG and cytokeratin (CK) were used as controls and HER1 expression levels were assayed with two different capture antibodies (denoted "HER1" and "HER1-2"). The amount of tumor lysate assayed is also shown (i.e., 0.25 µg, 2.5 µg, 20 µg).

FIG. 17 shows the expression profiling of HER1, HER2, HER3, c-Met, IGF1R, cKit, PI3K, and Shc in GCA tumor tissue samples using the COPIA multiplexed protein microarray platform described herein. IgG and cytokeratin (CK) were used as controls and HER1 expression levels were assayed with two different capture antibodies (denoted "HER1" and "HER1-2"). The GCA tissue samples analyzed in FIG. 17 all had the highest level of HER2 expression as determined by IHC (denoted "IHC 3+"). In particular, FIG. 17 shows that high HER2 expression as determined by IHC (i.e., IHC 3+) does not always correlate with HER2 expression levels measured by COPIA. Without being bound to any particular theory, the discordance observed between IHC and COPIA is due to the increased sensitivity and specificity and superior dynamic range achieved with the COPIA multiplexed protein microarray platform described herein. FIG. 17 also illustrates that functional profiling of multiple components of signal transduction pathways such as the HER2 and/or c-MET pathways provides valuable insight into the selection of one or more suitable anticancer drugs for the treatment of gastric cancer.

For example, FIG. 17 illustrates that Patient 14742212 will likely not respond to Herceptin® due to high levels of p95HER2 and HER3. Pertuzumab will also not be effective in preventing dimerization due to high level of p95HER2. One suitable anticancer therapy is the use of one or more small molecule pan-HER inhibitors such as PF-00299804. Another suitable anticancer therapy is the use of one or more c-MET inhibitors in combination with one or more pan-HER inhibitors such as neratinib. FIG. 17 further illustrates that Patient 12619785, with high levels of HER1, HER3, and IGF1R expression, should be administered one or more small molecule pan-HER inhibitors such as PF-00299804 or one or more IGF1R inhibitors in combination with one or more pan-HER inhibitors such as neratinib. FIG. 17 also illustrates that Patient 14609744 will likely not respond to Herceptin® due to high levels of HER3. However, this patient has a low level of p95 HER2. As such, one example of a suitable anticancer therapy is the use of pertuzumab or other HER2-dimerization inhibitor. In certain instances, pertuzumab may be combined with one or more c-MET inhibitors, pan-HER inhibitors, and/or PI3K inhibitors. In certain other instances, PI3K inhibitors are used in the combination along with mTOR and/or MEK inhibitors. Another example of a suitable anticancer therapy is the use of one or more pan-HER inhibitors in combination with one or more c-MET inhibitors. In addition, FIG. 17 shows that Herceptin® will likely not be an effective therapy due to co-expression of other RTKs in Patients 15530461 and 13313978. Pertuzumab will likely not be effective as p95HER2 level is high. One suitable anticancer therapy is the use of one or more pan-HER inhibitors in combination with one or more c-MET inhibitors.

Figure 18:
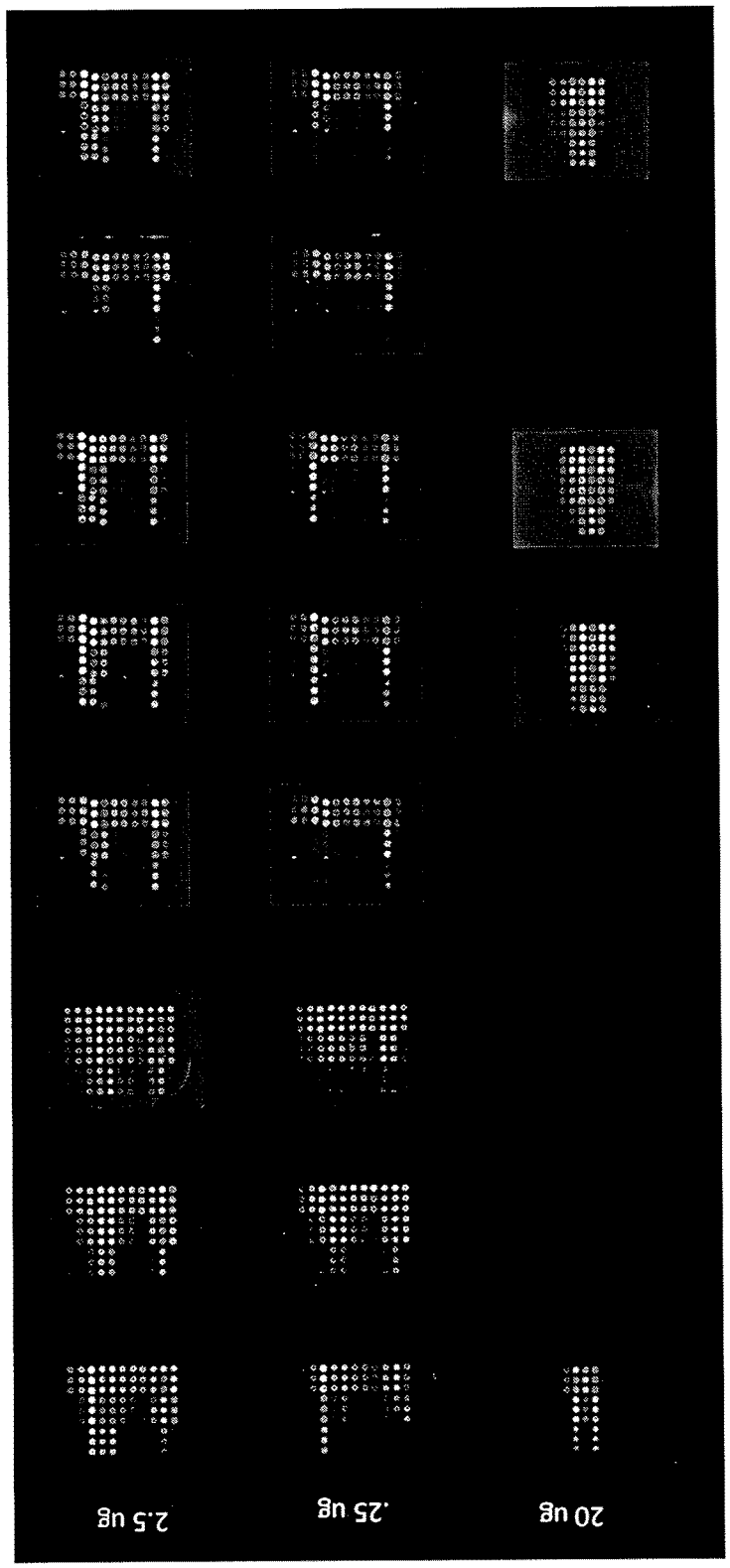
FIG. 18 shows the expression profiling of HER1, HER2, HER3, c-Met, IGF1R, cKit, PI3K, and Shc in additional GCA tumor tissue samples using COPIA. IgG and CK were used as controls and HER1 expression levels were assayed with two different capture antibodies (denoted "HER1" and "HER1-2"). The amount of tumor lysate assayed is also shown (i.e., 0.25 µg, 2.5 µg, 20 µg).
Figure 19:
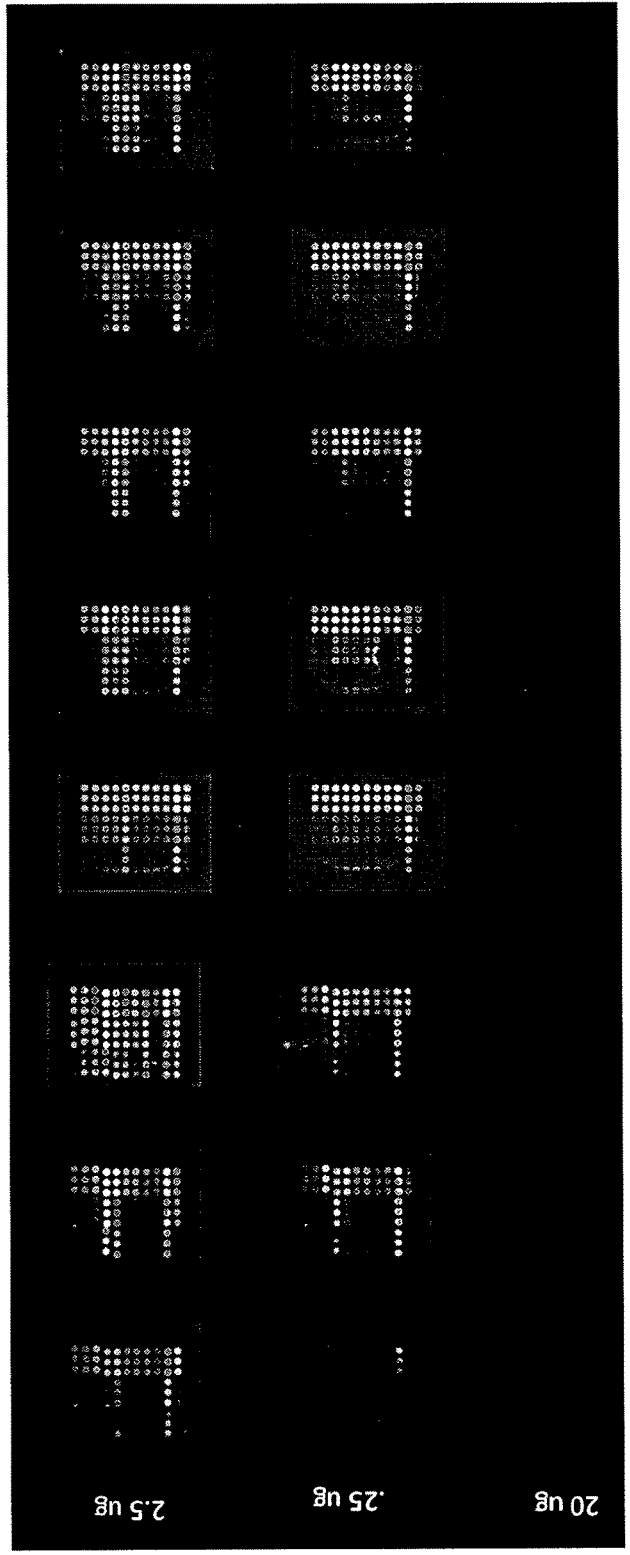
FIG. 19 shows the expression profiling of HER1, HER2, HER3, c-Met, IGF1R, cKit, PI3K, and Shc in additional GCA tumor tissue samples using COPIA. IgG and CK were used as controls and HER1 expression levels were assayed with two different capture antibodies (denoted "HER1" and "HER1-2"). The amount of tumor lysate assayed is also shown (i.e., 0.25 µg, 2.5 µg, 20 µg).

FIGS. 18 and 19 show the expression profiling of HER1, HER2, HER3, c-Met, IGF1R, cKit, PI3K, and She in additional GCA tumor tissue samples using COPIA. IgG and cytokeratin (CK) were used as controls and HER1 expression levels were assayed with two different capture antibodies (denoted "HER1" and "HER1-2"). The GCA tissue samples analyzed in FIGS. 18 and 19 had varying levels of HER2 expression as determined by IHC. In particular, these figures show that the level of HER2 expression as determined by IHC does not always correlate with the level of HER2 expression measured by COPIA. Without being bound to any particular theory, the discordance observed between IHC and COPIA is due to the increased sensitivity and specificity and superior dynamic range achieved with the COPIA multiplexed protein microarray platform described herein. In addition, these figures illustrate that functional profiling of multiple components of signal transduction pathways such as the HER2 and/or c-MET pathways provides valuable insight into the selection of one or more suitable anticancer drugs for the treatment of gastric cancer.

For example, FIG. 18 shows that Herceptin® may be effective in Patient 15199037 since p95HER2 level is low. However, there is a likelihood that this patient may develop resistance to Herceptin® due to the expression of HER3 and c-MET. As such, one example of a suitable anticancer therapy is to use or switch to one or more small molecule pan-HER inhibitors such as PF-00299804 and/or pertuzumab in combination with one or more c-MET inhibitors. FIG. 18 also illustrates that Patient 15286982 has a low level of HER2, but a high level of HER3. This patient may benefit from the administration of one or more pan-HER inhibitors and/or pertuzumab when combined with one or more c-MET inhibitors and one or more chemotherapeutic agents. FIG. 18 further illustrates that Patient 13777507, with no detectable HER2 expression, may be administered one or more c-MET inhibitors in combination with one or more chemotherapeutic agents.

FIG. 19 shows that one or more chemotherapeutic agents should be selected for Patient 13758944 due to low levels of HER1, HER2, HER3, and c-MET and undetectable levels of p95HER2. FIG. 19 also shows that Patient 13725795 may benefit from therapy with one or more pan-HER inhibitors and/or pertuzumab in combination with one or more c-MET inhibitors and one or more chemotherapeutic agents. In addition, FIG. 19 illustrates that Patient 13690624, with high levels of HER1, HER2, HER3, and IGF1Ras determined by COPIA, may be administered one or more pan-HER inhibitors and/or pertuzumab with one or more IGF1R inhibitors. FIG. 19 also shows that one or more c-MET inhibitors should be selected for Patient 14622912 due to undetectable levels of HER2, p95HER2, and HER3 and the presence of c-MET expression. FIG. 19 further shows that pertuzumab and/or one or more pan-HER inhibitors such as PF-00299804 in combination with one or more c-MET inhibitors may be selected as an appropriate therapy for Patient 04021208. Moreover, FIG. 19 shows that Patient 14691628, with c-MET and IGF1R expression as well as HER expression, may benefit from the use of one or more pan-HER inhibitors in combination with one or more c-MET inhibitors and one or more IGF inhibitors.

Figure 20:
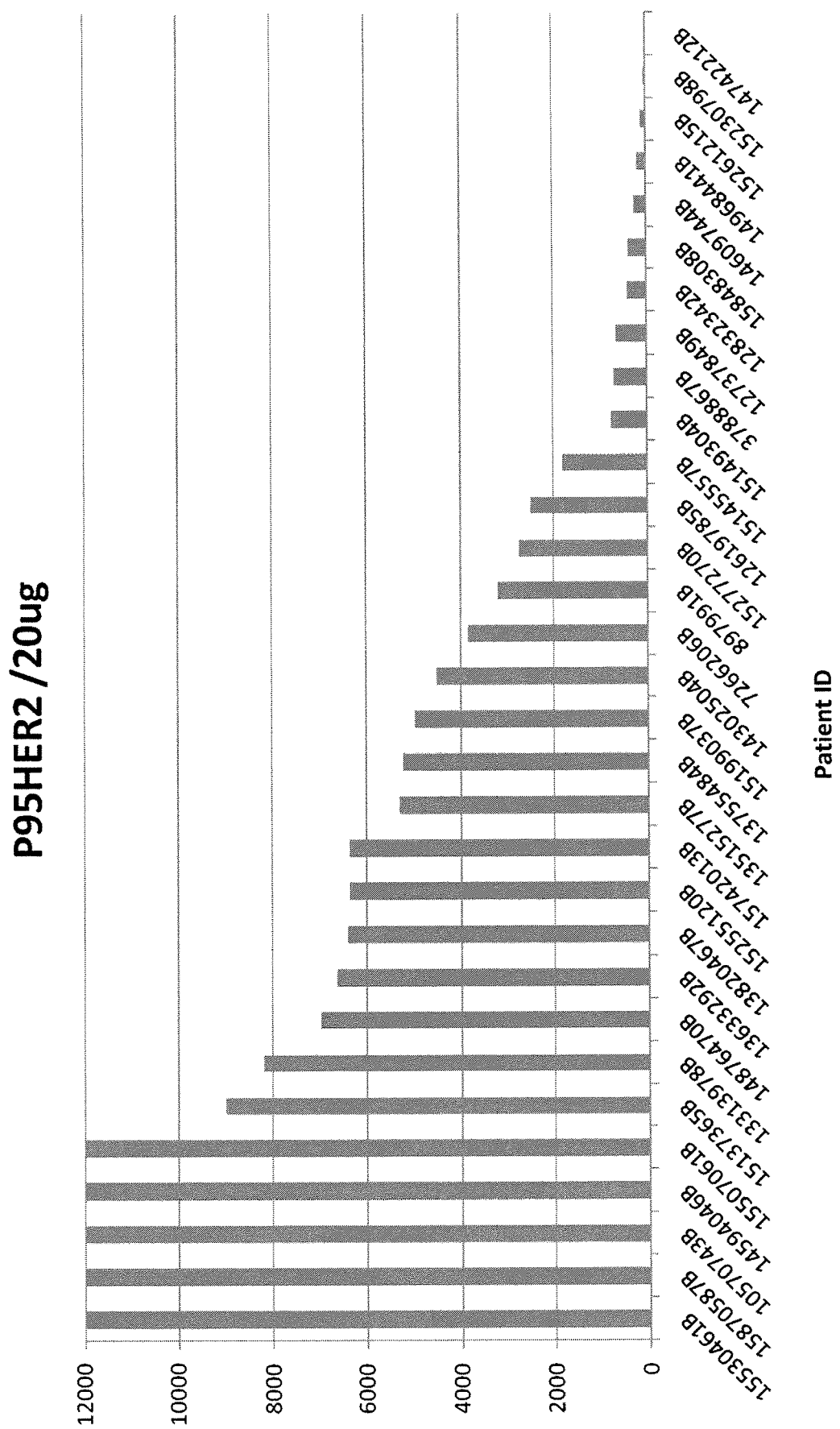
FIG. 20 shows the expression level of p95HER2 in GCA tumor tissue samples as determined by COPIA (e.g., using the truncated receptor proximity assay as described herein) in samples that were determined by IHC to be IHC 3+ for HER2 expression.

FIG. 20 shows the expression level of p95HER2 in GCA tumor tissue samples as determined by COPIA (e.g., using the truncated receptor proximity assay as described herein) in samples that were determined by IHC to be IHC 3+ for HER2 expression. GCA patients with high or higher p95HER2 expression levels have a higher probability of not responding to HER2-targeted therapies such as Herceptin® (e.g., GCA patients shown on the left side of the graph in FIG. 20), while GCA patients with low or lower p95HER2 expression levels have a higher probability of responding to HER2-targeted therapies such as Herceptin® (e.g., GCA patients shown on the right side of the graph in FIG. 20).

Figure 21:
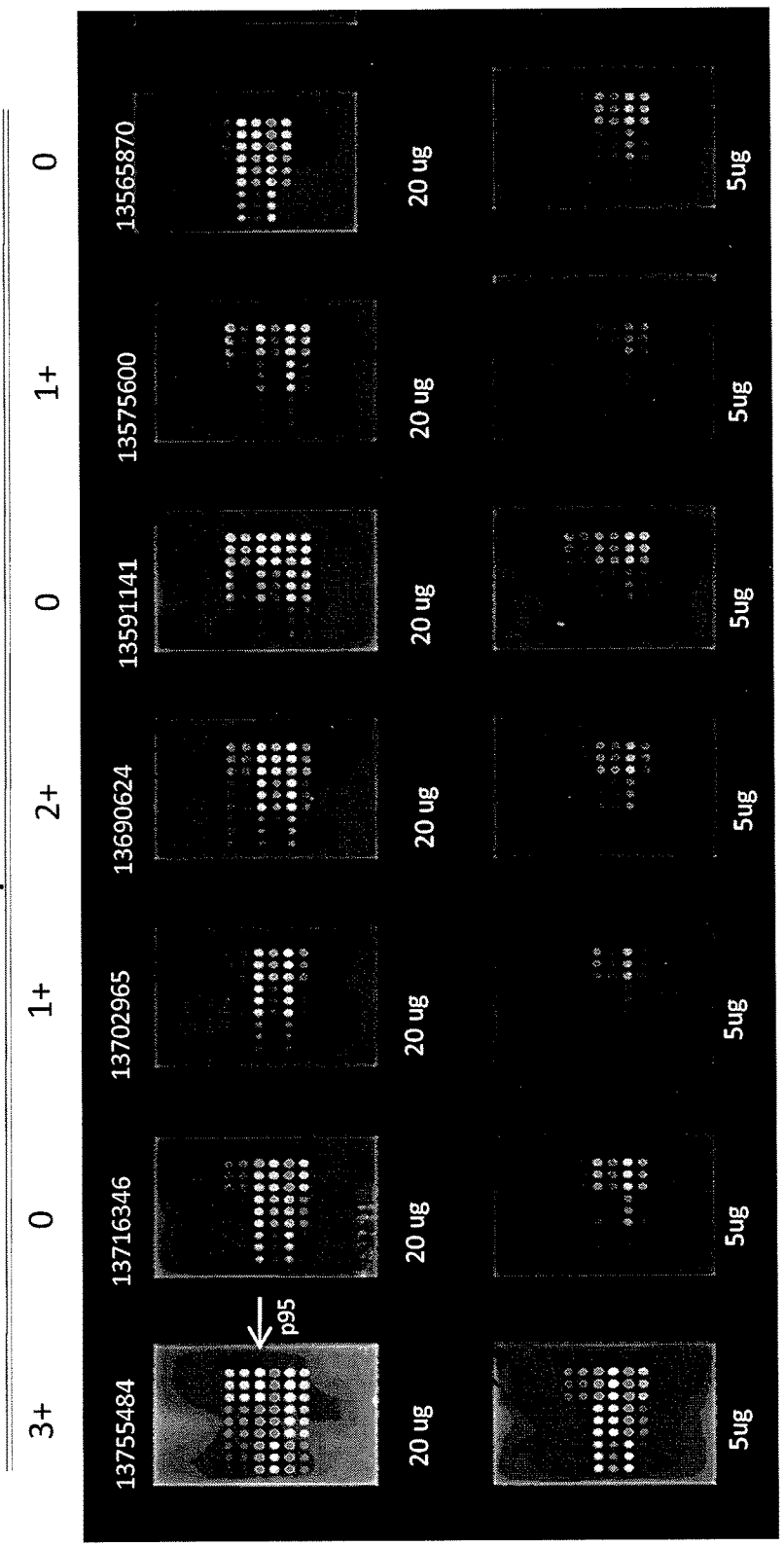
FIG. 21 shows the discordance observed between IHC and COPIA with regard to HER2 expression. CU=Computer Units normalized against a standard.
Figure 22:
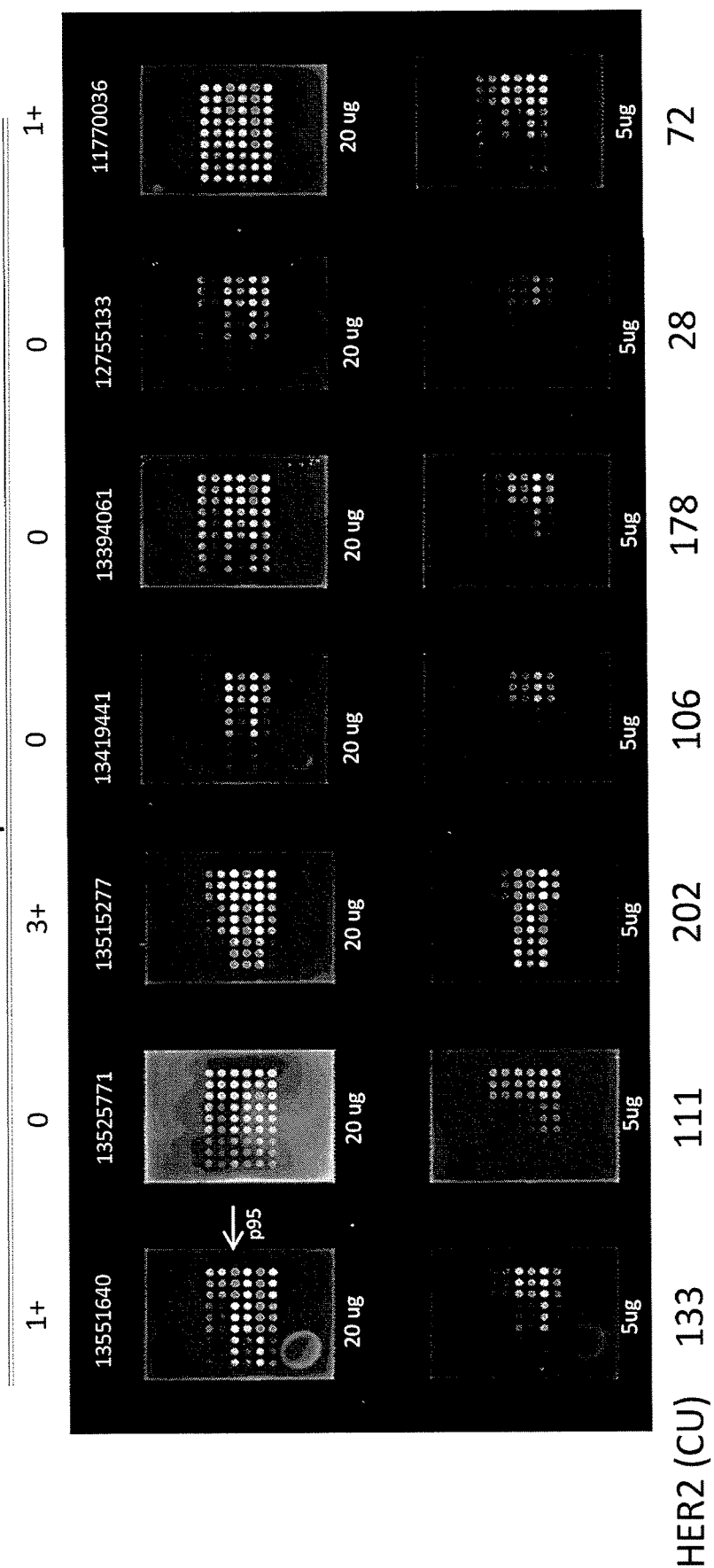
FIG. 22 shows additional GCA tumor tissue samples illustrating the discordance observed between IHC and COPIA with regard to HER2 expression.
Figure 23:
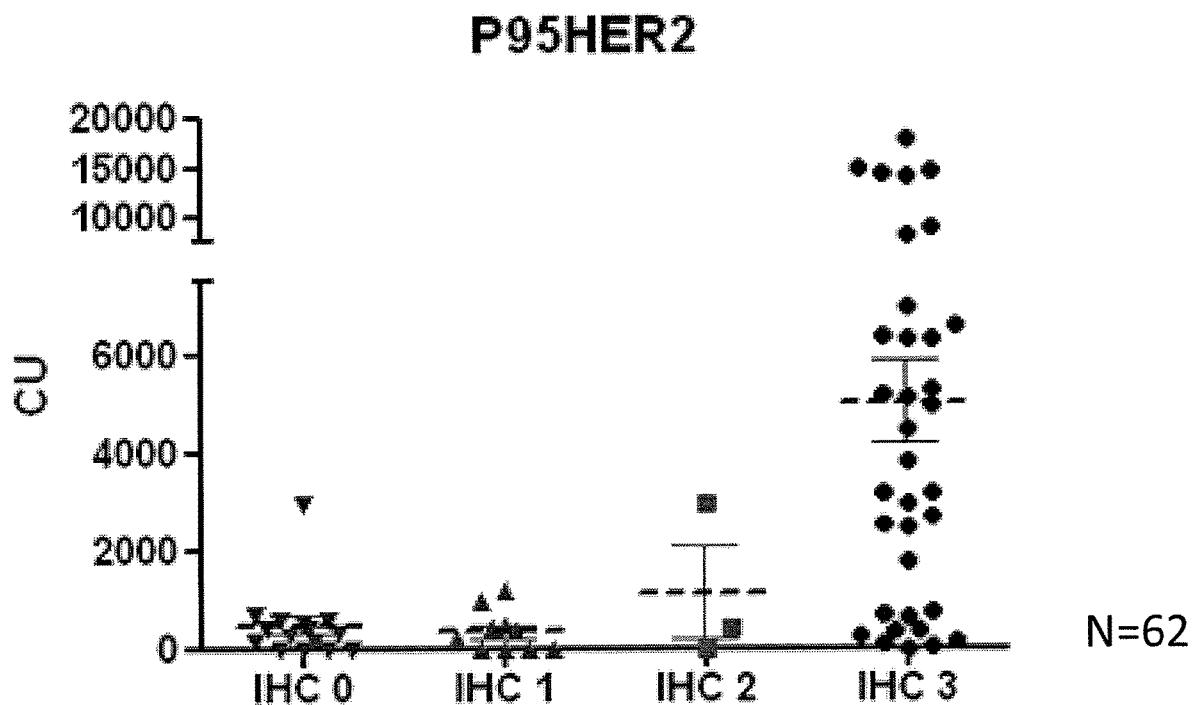
FIG. 23 shows p95HER2 expression levels observed by COPIA in GCA tumor samples that were also scored by IHC for HER2 expression.

FIGS. 21 and 22 show the discordance observed between IHC and COPIA with regard to HER2 expression. In particular, GCA tumor tissue samples that actually had high levels of HER2 were scored as having low of no detectable HER2 by IHC. These figures also show the expression level of p95HER2 in the HER2 discordant GCA samples (arrow). In addition, FIG. 23 illustrates the wide range of p95HER2 expression levels observed by COPIA in GCA tumor samples that were scored by IHC to have the highest level of HER2 expression (i.e., IHC 3+).

Example 13

Data Analysis for Quantitation of Signal Transduction Pathway Proteins in Gastric Cancer Cells This example illustrates the quantitation of the expression and/or activation levels of one or more analytes such as one or more signal transduction proteins in a biological sample (e.g., blood or tumor tissue) against a standard curve generated for the particular analyte of interest.

In some embodiments, each COPIA slide is scanned at three photomultiplier (PMT) gain settings to improve sensitivity and reduce the impact of saturation. Perkin Elmer ScanArray Express software is used for spot finding and signal quantitation. The identifiers for each spot are imported from a GenePix Array List (.gal) file. The de-identified study specific number for each clinical sample on a slide is incorporated into the resulting data set.

In other embodiments, background corrected signal intensities are averaged for replicate spots printed in triplicate. The relative fluorescence value of the respective reagent blank is subtracted from each sample. Several quality criteria are used to filter data from further analysis including limits on the spot footprint, coefficient of variation for spot replicates, overall pad background and the intensity of the reagent blank.

For each assay, a sigmoidal standard curve can be generated from multiple (e.g., two, three, four, five, six, seven, etc.) concentrations of serially diluted cell lysates prepared from cell lines such as MD-468 (HER1 positive), SKBr3 (HER2 positive), BT474 (HER2and p95HER2 positive), HCC827 (c-MET and HER1 positive), T47D stimulated with IGF (IGF1R positive), and/or T47D stimulated with HRG (HER3 positive). Each curve can be plotted as a function of signal intensity vs. log concentration derived units, CU (Computed Unit). The data can be fit to a five parameter equation (5PL) by nonlinear regression (Ritz, C. and Streibig, J. C., *J. Statistical Software*, 12, 1-22 (2005)), simultaneously fitting all three dilutions of the capture antibody. Fitting is carried out using R, an open source statistical software package (Development Core Team, R: A language and environment for statistical computing. R Foundation for Statistical Computing, Vienna, Austria. ISBN 3-900051-07-0 (2008)). To avoid over parameterization of the mathematical model and thereby improve accuracy, four parameters can be constrained, while each dilution can be solved for an individual inflection point. This process can be repeated for each PMT gain setting of 45, 50 and 60. This results in nine standard curves generated per assay, from three dilutions of capture antibody and three PMT scans. The built-in redundancy in the assay allows for one or more of the dilution/scan combinations to be eliminated if the fit of the standard curve has an $R^2$ less than 0.95 and thus improves subsequent predictions.

CU Calculation (based on standard curve)—The individual predictions from each of the standard curves (e.g., 3 capture antibody dilutions and 3 PMT gain-set scanning) can be combined into a single, final prediction. For each prediction, the slope of the point on the standard curve is calculated. This slope is taken with log-units on the x-axis, i.e., the units in the denominator of the slope are log Computed Units (CU). Second, a weighted average of the predictions is calculated, where the weights are determined from the slopes. Specifically, the weights are summed, and each point is given a weight equal to its slope divided by the total slopes. Each assay can be validated against predictions for known controls.

Example 14

Selection of Treatment for Gastric Cancer Using Collaborative Proximity Immunoassay (COPIA)

HER-2 Positive Advanced Gastric Cancer

In this proposed advanced gastric cancer clinical trial, the therapeutic efficacy of a combination of a HER-2 targeting agent, such as trastuzumab combined with a HER-1 and HER-2 dual inhibitor such as lapatinib, is evaluated in patients who have failed a single treatment of one or the other. The eligibility requirement is that the individual has previously failed at least one chemotherapy regimen, i.e., trastuzumab or lapatinib. The individual has a histologically confirmed adenocarcinoma of the stomach or gastro-esophageal junction with inoperable locally advanced or recurrent and/or metastatic disease, not amenable to curative therapy.

The individual has a HER2 positive tumor (primary tumor or metastasis defined as i) 3+ on IHC and/or ii) FISH (+). The HER2 positive tumor is confirmed using COPIA. The investigators plan this phase II dual therapy trial in patients with a COPIA confirmed HER-2 positive advanced gastric cancer after failure of at least one chemotherapy regimen.

Effectiveness of First Line Treatment in Gastric Cancer

This proposed randomized phase II trial determines how well epirubicin hydrochloride or 5-fluorouracil when given together with or without lapatinib ditosylate as first-line therapy in treating patients with gastric cancer.

The objective is to determine the activity of first-line treatment comprising epirubicin hydrochloride, or 5-fluorouracil with or without lapatinib ditosylate in patients with adenocarcinoma of the stomach or esophagogastric junction that is metastatic or not amenable to curative surgery according to HER2 and EGFR status. A further objective is to explore the activity of this regimen in patients who are HER2 negative by IHC (0 and 1+), and HER-2 negative by COPIA– or ±, as well as patients who are HER2 positive by IHC (2+ and 3+), and positive by COPIA+++ or ++++. It is an object to assess the concordance of HER2 determination by IHC and COPIA. In addition, EGFR status is also assessed by IHC and COPIA.

In this proposed study, patients are stratified according to institution and the combination of HER2/EGFR status as determined by immunohistochemistry (IHC) and COPIA assays (HER2 positive by IHC 2/3+ and positive by COPIA 3/4+ and EGFR positive by IHC and positive by COPIA vs HER2 negative by IHC and negative by COPIA, EGFR positive by IHC but negative by COPIA). Patients are randomized to 1 of 2 treatment arms.

After completion of study treatment, patients are followed at 8 weeks, every 3 months for 2 years, and then every 6 months thereafter.

Lapatinib vs. Lapatinib+Capecitabine in Treatment in HER2-Overexpressing Gastric Cancer The majority of patients with metastatic gastric cancer undergo first-line combined chemotherapy (e.g., platin derivates and fluoropyrimidines, sometimes combined with a taxane), but the role of second-line chemotherapy has not yet been well-defined. Therefore, progression during or shortly after first-line chemotherapy is a medical condition where no standard medical approach exists. The overexpression of EGFR and HER2 in gastric and gastroesophageal cancer make these indications prime candidates for treatment with a dual ErbB1/2 tyrosine kinase inhibitor (TKI) such as Lapatinib.

In this proposed study, HER2 overexpression is measured by COPIA and FISH (amplification or increased gene copy number). EGFR activation and expression is measured by COPIA. In one arm, patients are given Lapatinib and in the other arm, patients are given Lapatinib with Capecitabine. Patients are randomized to 1 of 2 treatment arms.

After completion of study treatment, patients are followed at 8 weeks, every 3 months for 2 years, and then every 6 months thereafter.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for selecting a suitable anticancer drug for the treatment of a subject with gastric cancer, the method comprising:
   (a) isolating a cancer cell from a subject with gastric cancer after administration of an anticancer drug, or prior to incubation with an anticancer drug;
   (b) determining the activation level of at least each of the following analytes in a cellular extract produced from the isolated cancer cell: HER1, HER2, HER3, c-Met, IGF1R, and PI3K,
   wherein determining the activation level of each of said analytes comprises:
      (i) incubating the cellular extract with a dilution series of capture antibodies specific for each of said analytes to form a plurality of captured analytes, wherein the capture antibodies are restrained on a solid support;
      (ii) washing and then incubating the plurality of captured analytes with detection antibodies comprising activation state-independent antibodies and activation state-dependent antibodies specific for each of said analytes to form a plurality of detectable captured analytes,
      wherein the activation state-independent antibodies are labeled with glucose oxidase, wherein the glucose oxidase and the activation state-independent antibodies are conjugated to a sulfhydryl-activated dextran molecule, wherein the activation state-dependent antibodies are labeled with a first member of a signal amplification pair, and wherein the glucose oxidase generates an oxidizing agent which channels to and reacts with the first member of the signal amplification pair;
      (iii) washing and then incubating the plurality of detectable captured analytes with a second member of the signal amplification pair to generate an amplified signal; and
      (iv) detecting the amplified signal generated from the first and second members of the signal amplification pair;
   (c) comparing the activation level of each of said analytes in the cellular extract to a reference activation level of each of said analytes that is generated in the absence of the anticancer drug; and
   (d) selecting the anticancer drug as suitable for the treatment of the subject with gastric cancer when each of said analytes in the cellular extract is substantially less activated than in the absence of the anticancer drug.

2. The method of claim 1, wherein the cancer cell is a circulating tumor cell or a fine needle aspirate (FNA) cell obtained from a tumor.

3. The method of claim 1, wherein the cancer cell is isolated from a sample.

4. The method of claim 3, wherein the sample is selected from the group consisting of whole blood, serum, plasma, tumor tissue, lymph, bone marrow aspirate, urine, saliva, and combinations thereof.

5. The method of claim 1, wherein the anticancer drug is selected from the group consisting of a monoclonal antibody, tyrosine kinase inhibitor, anti-proliferative agent, chemotherapeutic agent, and combinations thereof.

6. The method of claim 5, wherein the monoclonal antibody is selected from the group consisting of trastuzumab (Herceptin®), alemtuzumab (Campath®), bevacizumab (Avastin®), cetuximab (Erbitux®), gemtuzumab (Mylotarg®), panitumumab (Vectibix™), rituximab (Rituxan®), tositumomab (BEXXAR®), and combinations thereof.

7. The method of claim 5, wherein the tyrosine kinase inhibitor is selected from the group consisting of gefitinib (Iressa®), sunitinib (Sutent®), erlotinib (Tarceva®), lapatinib (Tykerb®), canertinib (CI 1033), semaxinib (SU5416), vatalanib (PTK787/ZK222584), sorafenib (Nexavar®), imatinib mesylate (Gleevec®), leflunomide (SU101), and combinations thereof.

8. The method of claim 5, wherein the anti-proliferative agent is an mTOR inhibitor selected from the group consisting of sirolimus (rapamycin), temsirolimus (CCI-779), everolimus (RAD001), and combinations thereof.

9. The method of claim 1, wherein step (b) comprises determining both the expression level and activation level of each of said analytes.

10. The method of claim 1, further comprising determining the expression level and/or activation level of one or more additional analytes in the cellular extract.

11. The method of claim 10, wherein the one or more additional analytes comprises one or more signal transduction molecules selected from the group consisting of receptor tyrosine kinases, non-receptor tyrosine kinases, tyrosine kinase signaling cascade components, and combinations thereof.

12. The method of claim 10, wherein the one or more additional analytes is selected from the group consisting of cKit, Shc, Akt, p70S6K, VEGFR, PDGFR, HER4, MEK, PTEN, SGK3, 4E-BP1, MAPK/ERK, PDK1, GSK-3β, Raf, SRC, NFkB-IkB, mTOR, Eph-a, Eph-b, Flt-3, Tie-1, Tie-2, Ab1, RET, FGFR1, FGFR2, FGFR3, FGFR4, RON, and combinations thereof.

13. The method of claim 1, wherein the solid support is selected from the group consisting of glass, plastic, chips, pins, filters, beads, paper, membrane, fiber bundles, and combinations thereof.

14. The method of claim 1, wherein the oxidizing agent is hydrogen peroxide ($H_2O_2$).

15. The method of claim 14, wherein the first member of the signal amplification pair is a peroxidase.

16. The method of claim 15, wherein the peroxidase is horseradish peroxidase (HRP).

17. The method of claim 15, wherein the second member of the signal amplification pair is a tyramide reagent.

18. The method of claim 1, wherein the activation level is a phosphorylation level.

\* \* \* \* \*